US010138235B2

(12) United States Patent
Alcouffe et al.

(10) Patent No.: US 10,138,235 B2
(45) Date of Patent: Nov. 27, 2018

(54) PYRAZOLOPYRIDINE DERIVATIVES, PREPARATION PROCESS THEREFOR AND THERAPEUTIC USE THEREOF

(71) Applicant: SANOFI, Paris (FR)

(72) Inventors: Chantal Alcouffe, Paris (FR); Kirsten Bjegarde, Bridgewater, NJ (US); Jacques Mauger, Bridgewater, NJ (US)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 15/451,955

(22) Filed: Mar. 7, 2017

(65) Prior Publication Data

US 2017/0174681 A1 Jun. 22, 2017

Related U.S. Application Data

(63) Continuation-in-part of application No. 14/364,420, filed as application No. PCT/EP2012/075328 on Dec. 13, 2012, now abandoned.

(30) Foreign Application Priority Data

Dec. 14, 2011 (FR) ..................................... 11 61589

(51) Int. Cl.
*C07D 471/04* (2006.01)

(52) U.S. Cl.
CPC ................. *C07D 471/04* (2013.01)

(58) Field of Classification Search
CPC .................................................. C07D 471/04
See application file for complete search history.

(56) References Cited

U.S. PATENT DOCUMENTS

| 2008/0182844 A1 | 7/2008 | Bjergarde et al. |
| 2009/0030010 A1 | 1/2009 | Schwede et al. |

FOREIGN PATENT DOCUMENTS

| JP | 2015500318 | | 1/2015 |
| WO | 2006050076 | A1 | 5/2006 |
| WO | 2006124863 | A2 | 11/2006 |
| WO | 2006130673 | A1 | 12/2006 |
| WO | 2008028617 | A1 | 3/2008 |
| WO | 2009038385 | A2 | 3/2009 |
| WO | 20100078427 | A1 | 7/2010 |
| WO | 2011045344 | A1 | 4/2011 |
| WO | 2012019954 | A1 | 2/2012 |
| WO | 2013087744 | | 6/2013 |

OTHER PUBLICATIONS

RN 1280290-46-1 Registry ED Entered STN: Apr. 14, 2011 CN Methanesulfonamide, N-[3-[3-phenyl-4-(trifluoromethyl)-1H-pyrazolo[3,4-b]pyridin-6-yl]phenyl]- (CA Index Name).*

STN-Chemical database registry entry # RN 1279827-69-8 for N-(3-(3-phenyl-4-(trifluoromethyl)-1 H-pyrazolo[3,4-b] pyridin-6-yl)phenyl)methanesulfonamide, Entered STN: Apr. 14, 2011.
STN-Chemical database reg is try entry # RN 1279827-77-8 for N-(3-(3-phenyl-4-(trifluoromethyl)-1 H-pyrazolo[3,4-b ] pyridin-6-yl)phenyl)methanesulfonamide, Entered STN: Apr. 14, 2011.
Online :"http://web.archive.org/web/20070228030707/http://www.interchim.com/interchim/inter_intro_chem.htm", accessed Feb. 19, 2015.
Duca "Insights from Ab Initio Quantum Chemical Calculations into the Preferred Tautomeric Forms and Binding Affinities to CDK2 of Substituted Pyrazolopyridines" Biopolymers, 2005, 80(2 and 3), 312-318.
STN-Chemical database registry# 1 011356-11-8, 6-(4-chlorophenyl)-1-ethyl-4-(trifluoromethyl)-1 H-Pyrazolo[3,4-b] pyridine, Entered STN: Apr. 1, 2008.
Chemical Abstracts Registry No. 1279823-91-4, entered into STN on Apr. 14, 2011, at p. 25 of Chemical Abstracts Service (CAS) STN chemical substance search performed Jun. 30, 2015.
Chemical Abstracts Registry No. 1279823-93-6, entered into STN on Apr. 14, 2011, at pp. 25-26 of Chemical Abstracts Service (CAS) STN chemical substance search performed Jun. 30, 2015.
Chemical Abstracts Registry No. 1279823-96-9, entered into STN on Apr. 14, 2011, at pp. 26-27 of Chemical Abstracts Service (CAS) STN chemical substance search performed Jun. 30, 2015.
Chemical Abstracts Registry No. 1279828-12-4, entered into STN on Apr. 14, 2011, at pp. 27-28 of Chemical Abstracts Service (CAS) STN chemical substance search performed Jun. 30, 2015.
Chemical Abstracts Registry No. 1279848-93-9, entered into STN on Apr. 14, 2011, at pp. 30-31 of Chemical Abstracts Service (CAS) STN chemical substance search performed Jun. 30, 2015.
Chemical Abstracts Registry No. 1279855-51-4, entered into STN on Apr. 14, 2011, at pp. 31-32 of Chemical Abstracts Service (CAS) STN chemical substance search performed Jun. 30, 2015.
Chemical Abstracts Registry No. 1280291-11-3, entered into STN on Apr. 14, 2011, at pp. 36-37 of Chemical Abstracts Service (CAS) STN chemical substance search performed Jun. 30, 2015.
Chemical Abstracts Service (CAS) STN chemical substance search performed Jun. 30, 2015, p. 1-41.
The United States Department of Justice, "Former Research Chemist at Global Pharmaceutical Company Sentenced to 18 Months in Prison for Theft of Trade Secrets" The United States Attorney's Office, District of New Jersey, http://www.justice.gov/usao/nj/Press/files/Li,%20Yuan%20Sentencing%20News%20Release.html, pp. 1-2 (May 7, 2012).

(Continued)

*Primary Examiner* — David K O'Dell
(74) *Attorney, Agent, or Firm* — McDonnell Boehnen Hulbert & Berghoff LLP

(57) ABSTRACT

The invention relates to FGF-inhibiting pyrazolopyrimidine derivatives of general formula (I)

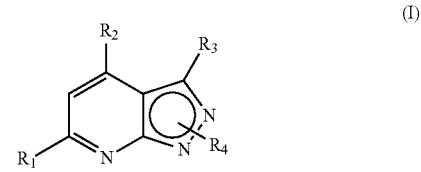

Figure 1:
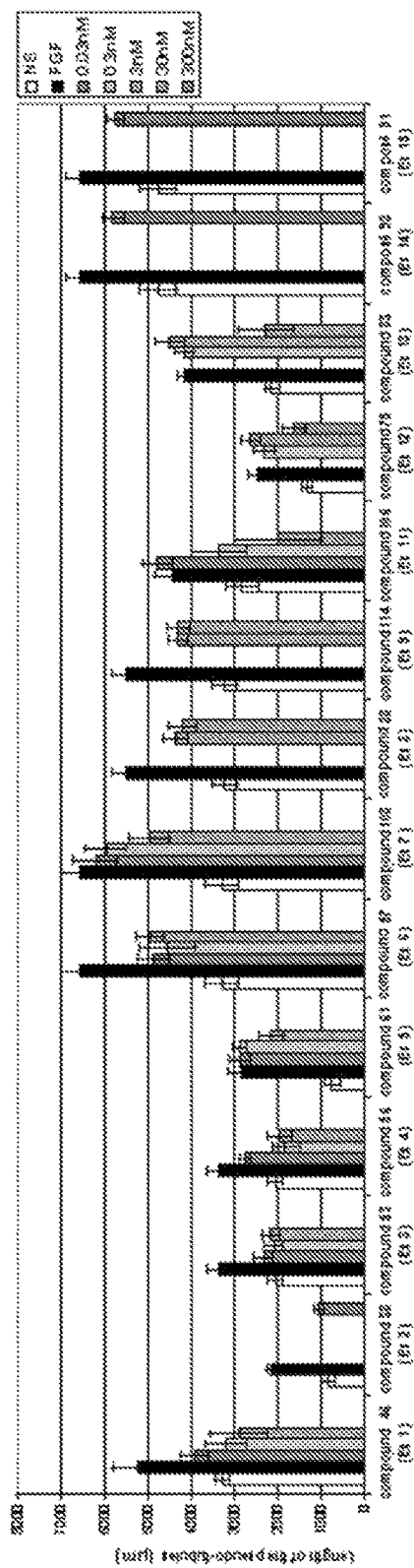

to a process for preparing them and to the therapeutic use thereof.

11 Claims, 2 Drawing Sheets

(56) References Cited

OTHER PUBLICATIONS

Chebano, V. et al., "Cyclocondensation reactions of 5-aminopyrazoles, pyruvic acids and aldehydes. Multicomponent approaches to pyrazolopyridines and related products" Tetrahedron, 63 (2007) pp. 1229-1242. (Dec. 11, 2006).
Tilton RG, Dixon RA, Brock TA "Growth factor antagonists for the treatment of diabetic vascular complications" Expert Opin Investig Drugs. Nov. 1997;6(11):1671-84.
Nicholas Turner and Richard Grose "Fibroblast growth factor signalling: from development to cancer" Nature Reviews vol. 10, Feb. 2010, 116-129.
Shuji Uematsu, Toshihiro Higashi, Kazuhiro Nouso, Kazuya Kariyama, Shin-Ichiro Nakamura, Mayumi Suzuki, Harushige Nakatsukasa, Yoshiyuki Kobayashi, Tadashi Hanafusa, Takao Tsuji and Yasushi Shiratori "Altered expression of vascular endothelial growth factor, fibroblast growth factor-2 and endostatin in patients with hepatocellular carcinoma" Journal of Gastroenterology and Hepatology (2005) 20, 583-588.
Gerold Untergassera, Stephan Madersbacherb, Peter Berger "Benign prostatic hyperplasia: age-related tissue-remodeling" Experimental Gerontology 40 (2005) 121-128 (Jan. 22, 2005).
Anne-Sophie Vercoutter-Edouart, Xavier Czeszak, Michel Crepin, Jerome Lemoine, Benoni Boilly, Xuefen Le Bourhis, Jean-Philippe Peyrat and Hubert Hondermarck "Proteomic Detection of Changes in Protein Synthesis Induced by Fibroblast Growth Factor-2 in MCF-7 Human Breast Cancer Cells" Experimental Cell Research 262, 59-68 (2001).
David A. Walsh "Angiogenesis in osteoarthritis and spondylosis: successful repair with undesirable outcomes" Current Opinion in Rheumatology 2004, 16:609-615.
Johannes Waltenberger "Modulation of Growth Factor Action Implications for the Treatment of Cardiovascular Diseases" Circulation 1997; 96: 4083-4094.
Wenbin Wang, Xiaotun Zhang, Gregory J. Mize and Thomas K. Takayama "Protease-Activated Receptor-1 Upregulates Fibroblast Growth Factor 7 in Stroma of Benign Prostatic Hyperplasia" The Prostate 68:1064-1075 (2008).
Shoko M. Yamada, Fumio Yamaguchi, Robert Brown, Mitchell S. Berger, and Richard S. Morrison "Suppression of Glioblastoma Cell Growth Following Antisense Oligonucleotide-Mediated Inhibition of Fibroblast Growth Factor Receptor Expression" GLIA 28:66-76 (1999).
Akihisa Yamashita, Yoshikazu Yonemitsu, Shinji Okano, Kazunori Nakagawa, Yutaka Nakashima, Takahiko Irisa, Yukihide Iwamoto, Yoshiyuki Nagai, Mamoru Hasegawa and Katsuo Sueishi "Fibroblast Growth Factor-2 Determines Severity of Joint Disease in Adjuvant-Induced Arthritis in Rats" J Immunol 2002; 168:450-457.
Avner Yayon, Yong-Sheng Ma, Michal Safran, Michael Klagsbrun and Ruth Halaban "Suppression of autocrine cell proliferation and tumorigenesis of human melanoma cells and fibroblast growth factor transformed fibroblasts by a kinase-deficient FGF receptor 1: evidence for the involvement of Src-family kinases" Oncogene (1997) 14, 2999 ± 3009.
Ganesh A. Thakur, Ritesh Tichkule, Shama Bajaj and Alexandros Makriyannis, "Lat.est Advances in Cannabinoid Receptor Agonists" Expert Opn. Ther. Pat. (2009) 19(12).
French Search Report for French Patent Application No. FR1161458 dated Mar. 23, 2012.
International Search Report for International Patent Application No. PCT/EP2012/075119 dated Jan. 28, 2013 (dated Feb. 5, 2013).
Volochnyuk, D. M., et at, "Approach to the Library of Fused Pyridine-4-carboxylic Acids by Combes-Type Reaction of Acyl Pyruvates and Electron-Rich Amino Heterocycles" J. Comb. Chern., 2010, 12, 510-517 (May 11, 2010).
Volochnyuk, D. M., et al., "Approach to the Library of Fused Pyridine-4-carboxylic Acids by Combes-Type Reaction of Acyl Pyruvates and Electron-Rich Amino Heterocycles" J. Comb. Chern., 2010, 12, Supporitng Information, pp. S1-S77 (May 11, 2010).

STN-Chemical database registry #1 011399-06-6, 4-(difluoromethyl)-1-methyl-6-(4-methylphenyl)-1 H-Pyrazolo[3,4-b] pyridine, Entered STN: Apr. 1, 2008.
STN-Chemical database registry #1 011392-78-1, 6-(2,3-dihydro-1,4-benzodioxin-6-yl)-1-methyl-4-(trifluoromethyl)-1 HPyrazolo[3,4-b]pyridine, Entered STN: Apr. 1, 2008.
STN-Chemical database registry #1 011392-22-5, 6-(3,4-dichlorophenyl)-1-methyl-4-(trifluoromethyl)-1 H-Pyrazolo[3,4-b]pyridine, Entered STN: Apr. 1, 2008.
Online: :"http://web.archive.org/web/2011 0704180118/http://www.abbypharmatech.com/ordercenter.htm", accessed Apr. 1, 2015.
Online: "http ://web.archive. org/web/20070630 171 81 3/http://www. enamine.net/index.php?option=com_content& task=view&id=22&menuid=5 1&PHPSESSID=64a4f248f69d671a413f487bb62c4d90" dated Jun. 30, 2007, accessed Apr. 1, 2015.
Online "http://web.archive.org/web/20031225052253/http://www.specs.net/", dated Dec. 25, 2003, accessed Apr. 1, 2015.
STN-Chemical database registry #834896-02-5, 3-cyclopropyl-6-(4-fluorophenyl)-1-methyl-4-(trifluoromethyl)-1 H-Pyrazolo[3,4-b]pyridine, Entered STN: Feb. 21, 2005.
Chemical Abstracts Registry No. 1000339-59-2, entered into STN on Jan. 20, 2008, at p. 11 of Chemical Abstracts Service (CAS) STN chemical substance search performed Jun. 30, 2015.
Chemical Abstracts Registry No. 1279829-79-6, entered into STN on Apr. 14, 2011, at p. 11 of Chemical Abstracts Service (CAS) STN chemical substance search performed Jun. 30, 2015.
Chemical Abstracts Registry No. 1312949-16-8, entered into STN on Jul. 18, 2011, at p. 11 of Chemical Abstracts Service (CAS) STN chemical substance search performed Jun. 30, 2015.
Chemical Abstracts Registry No. 1443284-09-0, entered into STN on Jul. 8, 2013, at p. 12 of Chemical Abstracts Service (CAS) STN chemical substance search performed Jun. 30, 2015.
Chemical Abstracts Registry No. 1279823-91-4, entered into STN on Apr. 14, 2011, at p. 13 of Chemical Abstracts Service (CAS) STN chemical substance search performed Jun. 30, 2015.
Chemical Abstracts Registry No. 1279855-51-4, entered into STN on Apr. 14, 2011 at p. 14 of Chemical Abstracts Service (CAS) STN chemical substance search performed Jun. 30, 2015.
Chemical Abstracts Registry No. 1279817-80-9, entered into STN on Apr. 14, 2011, at p. 24 of Chemical Abstracts Service (CAS) STN chemical substance search performed Jun. 30, 2015.
Chemical Abstracts Registry No. 1279823-93-6, entered into STN on Apr. 14, 2011, at p. 25 of Chemical Abstracts Service (CAS) STN chemical substance search performed Jun. 30, 2015.
Chemical Abstracts Registry No. 1279823-95-8, entered into STN on Apr. 14, 2011, at p. 26 of Chemical Abstracts Service (CAS) STN chemical substance search performed Jun. 30, 2015.
Chemical Abstracts Registry No. 1279823-96-9, entered into STN on Apr. 14, 2011, at p. 26 of Chemical Abstracts Service (CAS) STN chemical substance search performed Jun. 30, 2015.
Chemical Abstracts Registry No. 1279824-03-1, entered into STN on Apr. 14, 2011, at p. 27 of Chemical Abstracts Service (CAS) STN chemical substance search performed Jun. 30, 2015.
Chemical Abstracts Registry No. 1279828-12-4, entered into STN on Apr. 14, 2011, at p. 28 of Chemical Abstracts Service (CAS) STN chemical substance search performed Jun. 30, 2015.
Chemical Abstracts Registry No. 1279828-31-7, entered into STN on Apr. 14, 2011, at p. 28 of Chemical Abstracts Service (CAS) STN chemical substance search performed Jun. 30, 2015.
Chemical Abstracts Registry No. 1279838-18-4, entered into STN on Apr. 14, 2011, at p. 29 of Chemical Abstracts Service (CAS) STN chemical substance search performed Jun. 30, 2015.
Chemical Abstracts Registry No. 1279842-22-6, entered into STN on Apr. 14, 2011, at p. 29 of Chemical Abstracts Service (CAS) STN chemical substance search performed Jun. 30, 2015.
Chemical Abstracts Registry No. 1279848-90-6, entered into STN on Apr. 14, 2011, at p. 30 of Chemical Abstracts Service (CAS) STN chemical substance search performed Jun. 30, 2015.
Chemical Abstracts Registry No. 1279848-93-9, entered into STN on Apr. 14, 2011, at p. 30 of Chemical Abstracts Service (CAS) STN chemical substance search performed Jun. 30, 2015.

(56) References Cited

OTHER PUBLICATIONS

Chemical Abstracts Registry No. 1279854-63-5, entered into STN on Apr. 14, 2011, at p. 31 of Chemical Abstracts Service (CAS) STN chemical substance search performed Jun. 30, 2015.
Chemical Abstracts Registry No. 1279855-77-4, entered into STN on Apr. 14, 2011, at p. 32 of Chemical Abstracts Service (CAS) STN chemical substance search performed Jun. 30, 2015.
Chemical Abstracts Registry No. 1279856-20-0, entered into STN on Apr. 14, 2011, at p. 33 of Chemical Abstracts Service (CAS) STN chemical substance search performed Jun. 30, 2015.
Chemical Abstracts Registry No. 1279856-25-5, entered into STN on Apr. 14, 2011, at p. 33 of Chemical Abstracts Service (CAS) STN chemical substance search performed Jun. 30, 2015.
Chemical Abstracts Registry No. 1279856-62-0, entered into STN on Apr. 14, 2011, at p. 34 of Chemical Abstracts Service (CAS) STN chemical substance search performed Jun. 30, 2015.
Chemical Abstracts Registry No. 1279877-23-4, entered into STN on Apr. 14, 2011, at p. 34 of Chemical Abstracts Service (CAS) STN chemical substance search performed Jun. 30, 2015.
Chemical Abstracts Registry No. 1279877-39-2, entered into STN on Apr. 14, 2011, at p. 35 of Chemical Abstracts Service (CAS) STN chemical substance search performed Jun. 30, 2015.
Chemical Abstracts Registry No. 1279877-50-7, entered into STN on Apr. 14, 2011, at p. 35 of Chemical Abstracts Service (CAS) STN chemical substance search performed Jun. 30, 2015.
Chemical Abstracts Registry No. 1280290-06-3, entered into STN on Apr. 14, 2011, at p. 36 of Chemical Abstracts Service (CAS) STN chemical substance search performed Jun. 30, 2015.
Chemical Abstracts Registry No. 12780291-11-3, entered into STN on Apr. 14, 2011, at p. 36 of Chemical Abstracts Service (CAS) STN chemical substance search performed Jun. 30, 2015.
Chemical Abstracts Registry No. 1280291-80-6, entered into STN on Apr. 14, 2011, at p. 37 of Chemical Abstracts Service (CAS) STN chemical substance search performed Jun. 30, 2015.
Chemical Abstracts Registry No. 1279827-77-8, entered into STN on Apr. 14, 2011.
Chemical Abstracts Registry No. 1280290-46-1, entered into STN on Apr. 14, 2011.
Chemical Abstracts Registry No. 1279827-69-8, entered into STN on Apr. 14, 2011.
Chemical Abstracts Registry No. 1011356-11-8, entered into STN on Apr. 1, 2008.
Chemical Abstracts Registry No. 1011399-06-6, entered into STN on Apr. 1, 2008.
Chemical Abstracts Registry No. 1011399-78-1, entered into STN on Apr. 1, 2008.
Chemical Abstracts Registry No. 1011392-22-5, entered into STN on Apr. 1, 2008.
Chemical Abstracts Registry No. 834896-02-5, entered into STN on Feb. 21, 2005.
Patrick Auguste, Demirkan B. Gursel, Sylvie Lemiere, Diana Reimers, Pedro Cuevas, Fernando Carceller, James P. Di Santo, and Andreas Bikfalvi "Inhibition of Fibroblast Growth Factor/Fibroblast Growth Factor Receptor Activity in Glioma Cells Impedes Tumor Growth by Both Angiogenesis-dependent and -independent Mechanisms" Cancer Research 61, 1717-1726, Feb. 15, 2001.
Balicki, R. "Studies in the Field of Nitrogen Heterocyclic Compounds. Part XI*. Abnormal Cyclocondensation of Ethyl 4,4,4-Trifluoroacetoacetate With Aminopyrazoles" Polish Journal of Chemistry 57, 789 (1983).
Tracy T. Batchelor, A. Gregory Sorensen, Emmanuelle di Tomaso, Wei-Ting Zhang, Dan G. Duda, Kenneth S. Cohen, Kevin R. Kozak, Daniel P. Cahill, Poe-Jou Chen, Mingwang Zhu, Marek Ancukiewicz, Maciej M. Mrugala, Scott Plotkin, Jan Drappatz, David N. Louis, Percy Ivy, David T. Scadden, Thomas Benner, Jay S. Loeffler, Patrick Y. Wen, and Rakesh K. Jain "AZD2171, a Pan-VEGF Receptor Tyrosine Kinase Inhibitor, Normalizes Tumor Vasculature and Alleviates Edema in Glioblastoma Patients" Cancer Cell 11, 83-95, Jan. 2007.

Clotilde Billottet, Bassam Janji, Jean-Paul Thiery and Jacqueline Jouanneau "Rapid tumor development and potent vascularization are independent events in carcinoma producing FGF-1 or FGF-2" Oncogene (2002) 21, 8128-8139.
Sophie Boget, Albert Leriche, Andre' Revol "Basic fibroblast growth factor and keratinocyte growth factor over-expression in benign prostatic hyperplasia" II Farmaco 56 (2001) 467-469.
Sophie Boget, Catherine Cereser, Parviz Parvaz, Albert Leriche and Andre Revol "Fibroblast growth factor receptor 1 (FGFR1) is over-expressed in benign prostatic hyperplasia whereas FGFR2-IIIc and FGFR3 are not" European Journal of Endocrinology (2001) 145 303-310.
Oriol Casanovas, Daniel J. Hicklin, Gabriele Bergers, and Douglas Hanahan "Drug resistance by evasion of antiangiogenic targeting of VEGF signaling in late-stage pancreatic islet tumors" Cancer Cell, 2005, 8, 299-309 (Oct. 2005).
Lois A. Chandler, Barbara A. Sosnowski, Lydia Greenlees, Sharon L. Aukerman, Andrew Baird and Glenn F. Pierce "Prevalent Expression of Fibroblast Growth Factor (FGF) Receptors and FGF2 in Human Tumor Cell Lines" Int. J. Cancer: 81, 451-458 (1999).
Lin Chen, Rivka Adar, Xiao Yang, Efrat O. Monsonego, Cuiling Li, Peter V. Hauschka, Avner Yayon, and Chu-Xia Deng "Gly369Cys mutation in mouse FGFR3 causes achondroplasia by affecting both chondrogenesis and osteogenesis" J. Clin. Invest. 104:1517-1525 (1999).
Pamela Cowin, Tracey M Rowlands and Sarah J Hatsell "Cadherins and catenins in breast cancer" Current Opinion in Cell Biology 2005, 17:499-508 (Aug. 16, 2005).
Jennifer A. Doll, Frank K. Reiher, Susan E. Crawford, Michael R. Pins, Steven C. Campbell, and Noeel P. Bouck "Thrombospondin-1,Vascular Endothelial Growth Factor and FibroblastGrowth Factor-2 Are Key Functional Regulators of Angiogenesis in the Prostate" The Prostate 49:293-305 (2001).
S.E. Epstein, C..B Siegall, S. Biro, Y.M. Fu, D. FitzGerald and I. Pastan "Cytotoxic effects of a recombinant chimeric toxin on rapidly proliferating vascular smooth muscle cells" Circulation 1991, 84:778-787.
Paul W. Finch, Frank Murphy, Irma Cardinale, and James G. Krueger "Altered Expression of Keratinocyte Growth Factor and Its Receptor in Psoriasis" American Journal of Pathology, vol. 151, No. 6, Dec. 1997.
Janice L. Gabrilove "Angiogenic Growth Factors: Autocrine and Paracrine Regulation of Survival in Hematologic Malignancies" The Oncologist 2001, 6:4-7.
Dipak Giri and Michael Ittmann "Interleukin-8 is a Paracrine Inducer of Fibroblast Growth Factor 2, A Stromal and Epithelial Growth Factor in Benign Prostatic Hyperplasia" American Journal of Pathology, vol. 159, No. 1, Jul. 2001.
Dipak Giri, Frederic Ropiquet and Michael Ittmann "Alterations in Expression of Basic Fibroblast Growth Factor (FGF) 2 and its Receptor FGFR-1 in Human Prostate Cancer" Clin Cancer Res 1999;5:1063-1071.
Qingyang Gu, Dewen Wang, Xiaodan Wang, Ruiyun Peng, Jie Liu, Tao Jiang, Zhaohai Wang, Shuiming Wang and Hua Deng "Basic Fibroblast Growth Factor Inhibits Radiation-Induced Apoptosis of HUVECs. I. The PI3K|AKT Pathway and Induction of Phosphorylation of BAD" Radiation Research 161, 692-702 (2004).
Qingyang Gu, Dewen Wang, Xiaodan Wang, Ruiyun Peng, Jie Liu, Tao Jiang, Zhaohai Wang, Tao Jiang "Basic Fibroblast Growth Factor Inhibits Radiation-Induced Apoptosis of HUVECs. II. The RAS/MAPK Pathway and Phosphorylation of BAD at Serine 112" Radiation Research 161, 703-711 (2004).
Xinqiang Huang, Chundong Yu, Chengliu Jin, et al. "Ectopic Activity of Fibroblast Growth Factor Receptor 1 in Hepatocytes Accelerates Hepatocarcinogenesis by Driving Proliferation and Vascular Endothelial Growth Factor-Induced Angiogenesis" Cancer Res 2006;66:1481-1490.
Louise Hutley, Wenda Shurety, Felicity Newell, Ross McGeary, Nicole Pelton, Jennifer Grant, Adrian Herington, Donald Cameron, Jon Whitehead, and Johannes Prins "A Key Regulator of Human Adipogenesis" Diabetes, vol. 53, Dec. 2004 3097-3106.
Shigeo Kanazawa, Tsukasa Tsunoda, Eishi Onuma, Toshimitsu Majima, Mitsuyasu Kagiyama, and Kanako Kikuchi "VEGF, Basic-

(56) References Cited

OTHER PUBLICATIONS

FGF, and TGF-b in Crohn's Disease and Ulcerative Colitis: A Novel Mechanism of Chronic Intestinal Inflammation" The American Journal of Gastroenterology, vol. 96, No. 3, 2001.

M.A. Karajannis, L. Vincent, R. DiRenzo, S.V. Shmelkov, F. Zhang, E.J. Feldman, P. Bohlen, Z. Zhu, H. Sun, P. Kussie and S. Rafii "Activation of FGFR1b signaling pathway promotes survival, migration and resistance to chemotherapy in acute myeloid leukemia cells" Leukemia (2006) 20, 979-986.

Eli Keshet and Shmuel A. Ben-Sasson "Anticancer drug targets: approaching angiogenesis" The Journal of Clinical Investigation, Dec. 1999, vol. 104, No. 11.

Nasreen Khalil, Ying Dong Xu, Robert O'Connor and Vincent Duronio "Proliferation of Pulmonary Interstitial Fibroblasts is Mediated by Transforming Growth Factor-b1-induced Release of Extracellular Fibroblast Growth Factor-2 and Phosphorylation of p38 MAPK and JNK" J. Biol. Chem. 2005, 280:43000-43009.

Daniela Kovacs, Carlo Cota, Giorgia Cardinali, Nicaela Aspite, Giulia Bolasco, Ada Amantea, Maria Rosaria Torrisi and Mauro Picardo "Expression of keratinocyte growth factor and its receptor in clear cell acanthoma" Experimental Dermatology 2006: 15: 762-768.

B. Kwabi-Addo, M. Ozen and M. Ittmann "The role of fibroblast growth factors and their receptors in prostate cancer" Endocrine-Related Cancer (2004) 11 709-724.

Watcharin Loilome, Avadhut D. Joshi, Colette M. J. ap Rhys, Sara Piccirillo, Vescovi L. Angelo, Gary L. Gallia, Gregory J. Riggins "Glioblastoma cell growth is suppressed by disruption of fibroblast growth factor pathway signaling" J Neurooncol 2009 (Apr. 2, 2009).

Madiai F, Hussain SR, Goettl VM, Burry RW, Stephens RL Jr, Hackshaw KV "Upregulation of FGF-2 in reactive spinal cord astrocytes following unilateral lumbar spinal nerve ligation" Exp Brain Res. Feb. 2003;148(3):366-76.

Francesca Madiai, Virginia M. Goettl, Syed-Rehan Hussain, Alec R. Clairmont, Robert L. Stephens, Jr., and Kevin V. Hackshaw "Anti-Fibroblast Growth Factor-2 Antibodies Attenuate Mechanical Allodynia in a Rat Model of Neuropathic Pain" Journal of Molecular Neuroscience vol. 27, 2005 315-324.

Charles J. Malemud "Growth hormone, VEGF and FGF: Involvement in rheumatoid arthritis" Clinica Chimica Acta 375 (2007) 10-19 (Jul. 3, 2006).

N. Manabe, H. Oda, K. Nakamura, Y. Kuga, S. Uchida and H. Kawaguchi "Involvement of fibroblast growth factor-2 in joint destruction of rheumatoid arthritis patients" Rheumatology 1999;38:714-720.

M Manuvakhova, JV Thottassery, S Hays, Z Qu, SS Rentz, L Westbrook and FG Kern "Expression of the SNT-1/FRS2 phosphotyrosine binding domain inhibits activation of MAP kinase and PI3-kinase pathways and antiestrogen resistant growth induced by FGF-1 in human breast carcinoma cells" Oncogene (2006) 25, 6003-6014 (May 8, 2006).

Lindsay Marek, Kathryn E. Ware, Alexa Fritzsche, Paula Hercule, Wallace R. Helton, Jennifer E. Smith, Lee A. McDermott, Christopher D. Coldren, Raphael A. Nemenoff, Daniel T. Merrick, Barbara A. Helfrich, Paul A. Bunn, Jr., and Lynn E. Heasley "Fibroblast Growth Factor (FGF) and FGF Receptor-Mediated Autocrine Signaling in Non-Small Cell Lung Cancer Cells" Molecular Pharmacology Fast Forward. Published on Oct. 10, 2008 as doi:10.1124/ mol.108.049544 MOL#49544.

Hideaki Miyake, Isao Hara, Kazuo Gohji, Koji Yoshimura, Soichi Arakawa, Sadao Kamidono "Expression of basic fibroblast growth factor is associated with resistance to cisplatin in a human bladder cancer cell line" Cancer Letters 123 (1998) 121-126.

E. Cohen-Jonathan Moyal "Thérapies antiangiogéniques et radiothérapie : du concept à l'essai clinique [Angiogenic inhibitors and radiotherapy: from the concept to the clinical trial]" Cancer/Radiothérapie 13 (2009) 562-567.

Katrina Nicholes, Susan Guillet, Elizabeth Tomlinson, Kenneth Hillan, Barbara Wright, Gretchen D. Frantz, Thinh A. Pham, Lisa Dillard-Telm, Siao Ping Tsai, Jean-Philippe Stephan, Jeremy Stinson, Timothy Stewart, and Dorothy M. "French Ectopic Expression of Fibroblast Growth Factor 19 in Skeletal Muscle of Transgenic Mice" American Journal of Pathology, vol. 160, No. 6, Jun. 2002.

Olivier E Pardo, Claudia Wellbrock, Umme K Khanzada, Muriel Aubert, Imanol Arozarena, Sally Davidson, Frances Bowen, Peter J Parker, VV Filonenko, Ivan T Gout, Neil Sebire, Richard Marais, Julian Downward, and Michael J Seckl "FGF-2 protects small cell lung cancer cells from apoptosis through a complex involving PKCe, B-Raf and S6K2" The EMBO Journal (2006) 25, 3078-3088 (Jun. 29, 2006).

Olivier E. Pardo, Alexandre Arcaro, Giovanni Salerno, Selina Raguz, Julian Downward and Michael J. Seckl "Fibroblast Growth Factor-2 Induces Translational Regulation of Bcl-X L and Bcl-2 via a MEK-dependent Pathway: Correlation With Resistance to Etoposide-Induced Apoptosis" J. Biol. Chem. 2002, 277:12040-12046 (Jan. 28, 2002).

Olivier E. Pardo, Adeline Lesay, Alexandre Arcaro, Rita Lopes, Bee Ling Ng, Patricia H. Warne, Iain A. McNeish, Teresa D. Tetley, Nicholas R. Lemoine, Huseyin Mehmet, Michael J. Seckl and Julian Downward "Fibroblast Growth Factor 2-Mediated Translational Control of IAPs Blocks Mitochondrial Release of Smac/DIABLO and Apoptosis in Small Cell Lung Cancer Cells" Mol. Cell. Biol. 2003, 23(21):7600.

Marco Presta, Marco Rusnati, Patrizia Dell'Era, Elena Tanghetti, Chiara Urbinati, Roberta Giuliani, Darla Leali "Examining New Models for the Study of Autocrine and Paracrine Mechanisms of Angiogenesis Through FGF2-Transfected Endothelial and Tumour Cells" Advances in Experimental Medicine and Biology vol. 476, 2000, pp. 7-34.

Einar K. Rofstad and Ellen F. Halsør "Vascular Endothelial Growth Factor, Interleukin 8, Platelet-derived Endothelial Cell Growth Factor, and Basic Fibroblast Growth Factor Promote Angiogenesis and Metastasis in Human Melanoma Xenografts" Cancer Res 2000;60:4932-4938 (Sep. 1, 2000).

Andreas Roidl, Hans-Jurgen Berger, Sushil Kumar, Johannes Bange, Pjotr Knyazev, and Axel Ullrich "Resistance to Chemotherapy is Associated with Fibroblast Growth Factor Receptor 4 Up-Regulation" Clin Cancer Res 2059 2009;15 (6)Mar. 15, 2009.

Maria A. Rupnick, Dipak Panigrahy, Chen-Yu Zhang, Susan M. Dallabrida, Bradford B. Lowell, Robert Langer, and M. Judah Folkman "Adipose tissue mass can be regulated through the vasculature" PNAS Aug. 6, 2002 vol. 99 No. 16, 10730-10735.

K Sahadevan, S Darby, HY Leung, ME Mathers, CN Robson and VJ Gnanapragasam "Selective over-expression of fibroblast growth factor receptors 1 and 4 in clinical prostate cancer" J Pathol 2007; 213: 82-90 (Jul. 2, 2007).

Jo EI J. Schultz, Sandra A. Witt, Michelle L. Nieman, Peter J. Reiser, Sandra J. Engle, Ming Zhou, Sharon A. Pawlowski, John N. Lorenz, Thomas R. Kimball, and Thomas Doetschman "Fibroblast growth factor-2 mediates pressure-induced hypertrophic response" J. Clin. Invest. 104:709-719 (1999) (Sep. 1999).

Kathryn L. Schwertfeger "Fibroblast Growth Factors in Development and Cancer: Insights from the Mammary and Prostate Glands" Current Drug Targets, 2009, 10, 632-644.

Frank Strutz, Eric G. Neilson "New insights into mechanisms of fibrosis in immune renal injury" Springer Semin Immunopathol (2003) 24:459-476.

Shinji Tanaka, Shigeki Arii "Current status and perspective of antiangiogenic therapy for cancer: hepatocellular carcinoma" Int J Clin Oncol (2006) 11:82-89.

Thomas DA, Giles FJ, Cortes J, Albitar M, Kantarjian HM "Antiangiogenic therapy in leukemia" Acta Haematol. 2001;106(4):190-207.

M. Thorn, Y. Raab, A. Larsson, B. Gerdin & R. Hallgren "Intestinal Mucosal Secretion of Basic Fibroblast Growth Factor in Patients with Ulcerative Colitis" Scand J Gastroenterol 2000 (4) 408-412.

* cited by examiner

PYRAZOLOPYRIDINE DERIVATIVES, PREPARATION PROCESS THEREFOR AND THERAPEUTIC USE THEREOF

This application is a continuation-in-part of U.S. application Ser. No. 14/364,420, filed Jun. 11, 2014, which is a national stage application under 35 U.S.C. § 371 of International Application No. PCT/EP2012/075328, filed Dec. 13, 2012, which claims priority to France Application No. 1161589, filed on Dec. 14, 2011, the disclosures of which are explicitly incorporated by reference herein.

The present invention relates to pyrazolopyrimidine derivatives that inhibit the FGF (fibroblast growth factor) receptors, to a process for preparing them and to the therapeutic use thereof.

FGFs are a family of polypeptides synthesized by a large number of cells during embryonic development and by adult tissue cells under various pathological conditions.

The present invention relates to compounds corresponding to formula (I):

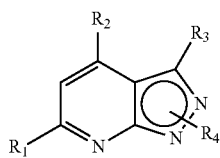

in which:
the representation of the pyrazole ring indicates that the substituent $R_4$ may be borne either by the nitrogen alpha to the pyridine ring (I') or by the nitrogen alpha to the carbon bearing a substituent $R_3$ (I") such that:

Either

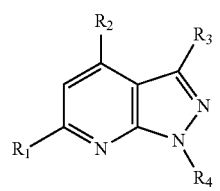

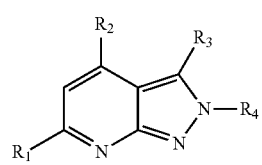

$R_1$ represents an aryl, pyridyl or pyrazolyl group optionally substituted with one or more substituents chosen from:
  a halogen atom,
  a group —$CF_3$,
  a cyano group,
  a group —$NR_6R_6'$ in which $R_6$ and $R_6'$ are as defined below,
  a group —$NR_{10}R_{11}$ such that $R_{10}$ and $R_{11}$ form, together with the nitrogen atom to which they are attached, a saturated or unsaturated heterocycle comprising one or more heteroatoms chosen from a nitrogen atom and an oxygen atom so as advantageously to form a pyrazole, morpholine, pyrrolidine or piperidine, optionally substituted with one or more substituents chosen from a halogen atom and a linear or branched alkyl group,
  a group —$CH_2NR_{10}R_{11}$ such that $R_{10}$ and $R_{11}$ form, together with the nitrogen atom to which they are attached, a saturated or unsaturated heterocycle comprising one or more heteroatoms chosen from a nitrogen atom and an oxygen atom so as advantageously to form a morpholinyl group,
  a group —$COR_{12}$ in which $R_{12}$ represents a hydroxyl group or a group —$NR_6R_6'$, in which $R_6$ and $R_6'$ are as defined below,
  a group —$CONR_7R_7'$ such that $R_7$ and $R_7'$ form, together with the nitrogen atom to which they are attached, a heterocycloalkyl comprising one or more heteroatoms chosen from a nitrogen atom and an oxygen atom so as advantageously to form a pyrrolidinyl group,
  a group —$(CH_2)_pNHSO_2CH_3$ in which p represents 0 or 1,
  a group —$OR_{13}$ in which $R_{13}$ represents a linear group $(C_1-C_3)$alkyl,
  a group $(C_1-C_3)$alkyl,
Or $R_1$ represents a bicyclic group of formula A below:

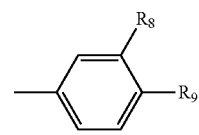

in which $R_8$ and $R_9$ form, together with the carbon atoms to which they are attached, a saturated or unsaturated heterocycle comprising one or more heteroatoms chosen from a nitrogen atom, an oxygen atom and a sulfur atom, such that the group (A) advantageously forms a dihydrobenzimidazolonyl, indolyl, dihydrobenzoxazinyl, benzothiazolyl or benzimidazolyl group, optionally substituted with one or more linear alkyl groups,
$R_2$ represents a group:
  —$CF_3$,
  —$CHF_2$,
  —COOH,
or
  —$CONHR_5$, in which $R_5$ is as defined below,
$R_3$ represents:
  a hydrogen atom,
  an aryl group, optionally substituted with an alkoxymethyl group,
  a cycloalkyl group,
or
  a heteroaryl group chosen from thienyl and pyridyl groups,
$R_4$ represents:
  a hydrogen atom,
  a linear group $(C_1-C_3)$alkyl, optionally substituted with a group —$NR_6R'_6$ in which $R_6$ and $R'_6$ are as defined below or a group —$NR_7R'_7$ such that $R_7$ and $R_{7'}$ form, together with the nitrogen atom to which they are attached, a heterocycloalkyl comprising one or more heteroatoms chosen from a nitrogen atom and an oxygen atom, $R_5$ represents:
- a hydrogen atom,
- a linear group $(C_1-C_3)$alkyl, optionally substituted with a pyridyl group, or
- an aromatic group chosen from aryl and pyridyl, $R_6$ and $R'_6$, which may be identical or different, represent a hydrogen atom or a linear alkyl group, in the form of the base or of an acid-addition or base-addition salt.

The compounds of formula (I) may exist in the form of bases or salified with acids or bases, especially pharmaceutically acceptable acids or bases. Such addition salts form part of the invention.

These salts are advantageously prepared with pharmaceutically acceptable acids, but salts of other acids that are of use, for example, for purifying or isolating the compounds of formula (I) also form part of the invention.

In the context of the present invention, and unless otherwise mentioned in the text, the following definitions apply:
a halogen atom: a fluorine, chlorine, bromine or iodine atom;
an alkyl group: a linear or branched saturated hydrocarbon-based aliphatic group, comprising from 1 to 6 carbon atoms. Examples that may be mentioned include methyl, ethyl, propyl, isopropyl, butyl, isobutyl, pentyl, etc. groups;
a cycloalkyl group: a 3- to 8-membered cyclic alkyl group, comprising between 3 and 6 carbon atoms, the said cycloalkyl group being optionally substituted with one or more halogen atoms and/or alkyl groups. Examples that may be mentioned include cyclopropyl and cyclopentyl groups;
an alkoxy group: a radical —O-alkyl in which the alkyl group is as defined previously;
an alkoxyalkyl group: a radical of formula alkyl-O-alkyl, in which the identical or different alkyl groups are as defined previously;
an aryl group: a cyclic aromatic group comprising between 5 and 10 carbon atoms, for example a phenyl group;
a heteroaryl group: a cyclic aromatic group comprising between 3 and 10 atoms including one or more heteroatoms, for example between 1 and 4 heteroatoms, such as nitrogen, oxygen or sulfur, this group comprising one or more rings, preferably one or two rings. The heteroaryls may comprise several fused rings. The heteroaryls are optionally substituted with one or more alkyl groups or an oxygen atom. Examples that may be mentioned include thienyl, pyridyl, pyrazolyl, imidazolyl, thiazolyl and triazolyl groups;
a heterocycloalkyl: a cyclic alkyl group comprising from 4 to 9 atoms forming this ring and of which one or two are heteroatoms, such as oxygen, nitrogen or sulfur. Mention may be made especially of piperidyl, pyrrolidinyl, piperazinyl, tetrahydropyranyl, morpholinyl and homopiperazinyl groups;
a heterocyclic group: a heteroaryl group or a heterocycloalkyl group as defined previously.

The present invention relates particularly to compounds corresponding to formula (I):

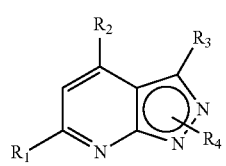

(I)

in which:
$R_1$ represents a phenyl, pyridyl or pyrazolyl group optionally substituted with one or more substituents chosen from:
- a fluorine atom,
- a group —$CF_3$,
- a cyano group,
- a group —$NR_6R_6'$ in which $R_6$ and $R_6'$ are as defined below,
- a group —$NR_{10}R_{11}$ such that $R_{10}$ and $R_{11}$ form, together with the nitrogen atom to which they are attached, a saturated or unsaturated heterocycle comprising one or more heteroatoms chosen from a nitrogen atom and an oxygen atom so as advantageously to form a pyrazolyl, morpholinyl, pyrrolidinyl or piperidyl, optionally substituted with one or more linear alkyl groups,
- a group —$CH_2NR_{10}R_{11}$ such that $R_{10}$ and $R_{11}$ form, together with the nitrogen atom to which they are attached, a saturated heterocycle comprising one or more heteroatoms chosen from a nitrogen atom and an oxygen atom so as advantageously to form a morpholinyl group,
- a group —$COR_{12}$ in which $R_{12}$ represents a hydroxyl group or a group —$NR_6R_6'$, in which $R_6$ and $R_6'$ are as defined below,
- a group —$CONR_7R_7'$ in which $R_7$ and $R_7'$ form, together with the nitrogen atom to which they are attached, a heterocycloalkyl comprising a nitrogen heteroatom,
- a group —$(CH_2)NHSO_2CH_3$ in which p represents 0 or 1,
- a group —$OR_{13}$ in which $R_{13}$ represents a linear group $(C_1-C_3)$alkyl,
- a group $(C_1-C_3)$alkyl, Or $R_1$ represents a bicyclic group of formula A below:

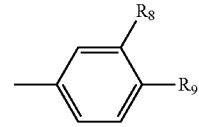

(A)

in which $R_8$ and $R_9$ form, together with the carbon atoms to which they are attached, a saturated or unsaturated heterocycle comprising one or more heteroatoms chosen from a nitrogen atom, an oxygen atom and a sulfur atom, such that A represents a dihydrobenzimidazolonyl, indolyl, dihydrobenzoxazinyl, benzothiazolyl or benzimidazolyl group, optionally substituted with one or more linear alkyl groups, $R_2$ represents a group:
- —$CF_3$,
- —$CHF_2$,
- —COOH, or
- —$CONHR_5$, in which $R_5$ is as defined below, $R_3$ represents:
- a hydrogen atom,
- a phenyl group, optionally substituted with an alkoxymethyl group,
- a cycloalkyl group comprising 3 carbon atoms, or
- a heteroaryl group chosen from thienyl and pyridyl groups, R$_4$ represents:
  a hydrogen atom,
  a linear group (C$_1$-C$_3$)alkyl, optionally substituted with a group —NR$_6$R$_6$' in which R$_6$ and R$_6$', which may be identical or different, represent a methyl group or a group —NR$_7$R$_7$' such that R$_7$ and R$_7$' form, together with the nitrogen atom to which they are attached, a heterocycloalkyl comprising one or more heteroatoms chosen from a nitrogen atom and an oxygen atom, R$_5$ represents:
  a hydrogen atom,
  a linear group (C$_1$-C$_3$)alkyl, optionally substituted with a pyridyl group,
  or
  a phenyl or pyridyl group, R$_6$ and R'$_6$, which may be identical or different, represent a hydrogen atom or a linear alkyl group, in the form of the base or of an acid-addition or base-addition salt.

Among the compounds of formula (I) according to the invention, a first group of compounds consists of the compounds corresponding to formula (I) below, with the exception of:

3-(4-Fluorobenzyl)-1-methyl-6-[1-(2-methyl-2H-pyrazol-3-yl)-imidazo[1,5-a]pyridine-3-carbonyl]-1H-quinazoline-2,4-dione;

3-(4-Fluorobenzyl)-1-methyl-6-[1-(1-methyl-1H-pyrazol-4-yl)-imidazo[1,5-a]pyridine-3-carbonyl]-1H-quinazoline-2,4-dione;

3-(4-Fluorobenzyl)-1-methyl-6-[1-(1-methyl-1H-pyrazol-4-yl)-imidazo[1,5-a]pyridine-3-carbonyl]-1H-quinazoline-2,4-dione;

3-(4-Fluorobenzyl)-6-[1-(1-methyl-1H-pyrazol-4-yl)-imidazo[1,5-a]pyridine-3-carbonyl]-1-propyl-1H-quinazoline-2,4-dione;

[6-(1-Bromo-2-methylindolizine-3-carbonyl)-2,4-dioxo-1,4-dihydro-2H-quinazolin-3-yl]acetic acid methyl ester;

[6-(1-Bromo-2-methylindolizine-3-carbonyl)-2,4-dioxo-1,4-dihydro-2H-quinazolin-3-yl]acid tert-butyl ester;

6-(4-Fluoro-3-methoxycarbonylphenyl)-3-phenyl-1H-pyrazolo[3,4-b]pyridine-4-carboxylic acid;

2-Fluoro-5-(3-phenyl-4-trifluoromethyl-1H-pyrazolo[3,4-b]pyridin-6-yl)benzoic acid;

N,N-Dimethyl-3-(1-methyl-3-phenyl-4-trifluoromethyl-1H-pyrazolo[3,4-b]pyridin-6-yl)benzamide;

N,N-Dimethyl-4-(1-methyl-3-phenyl-4-trifluoromethyl-1H-pyrazolo[3,4-b]pyridin-6-yl)benzamide;

5-(1-Methyl-3-phenyl-4-trifluoromethyl-1H-pyrazolo[3,4-b]pyridin-6-yl)nicotinonitrile;

6-Benzothiazol-5-yl-1-methyl-3-phenyl-4-trifluoromethyl-1H-pyrazolo[3,4-b]pyridine;

1-Methyl-3-phenyl-6-(6-pyrrolidin-1-ylpyridin-3-yl)-4-trifluoromethyl-1H-pyrazolo[3,4-b]pyridine;

1-Methyl-6-(6-morpholin-4-ylpyridin-3-yl)-3-phenyl-4-trifluoromethyl-1H-pyrazolo[3,4-b]pyridine;

3-(1-Methyl-3-phenyl-4-trifluoromethyl-1H-pyrazolo[3,4-b]pyridin-6-yl)benzamide;

N-[4-(1-Methyl-3-phenyl-4-trifluoromethyl-1H-pyrazolo[3,4-b]pyridin-6-yl)benzyl]methanesulfonamide;

1-Methyl-6-(1-methyl-1H-indol-6-yl)-3-phenyl-4-trifluoromethyl-1H-pyrazolo[3,4-b]pyridine;

N-[3-(1-Methyl-3-phenyl-4-trifluoromethyl-1H-pyrazolo[3,4-b]pyridin-6-yl)phenyl]methanesulfonamide;

4-Methyl-7-(1-methyl-3-phenyl-4-trifluoromethyl-1H-pyrazolo[3,4-b]pyridin-6-yl)-3,4-dihydro-2H-benzo[1,4]oxazine;

N-[3-(1-Methyl-3-phenyl-4-trifluoromethyl-1H-pyrazolo[3,4-b]pyridin-6-yl)benzyl]methanesulfonamide;

6-(4-Methoxyphenyl)-1-methyl-3-phenyl-4-trifluoromethyl-1H-pyrazolo[3,4-b]pyridine;

2-Fluoro-N-methyl-5-(1-methyl-3-phenyl-4-trifluoromethyl-1H-pyrazolo[3,4-b]pyridin-6-yl)benzamide;

Dimethyl[3-(1-methyl-3-phenyl-4-trifluoromethyl-1H-pyrazolo[3,4-b]pyridin-6-yl)phenyl]amine;

6-[4-(3,5-Dimethylpyrazol-1-yl)phenyl]-1-methyl-3-phenyl-4-trifluoromethyl-1H-pyrazolo[3,4-b]pyridine;

1-Methyl-6-(3-morpholin-4-ylmethylphenyl)-3-phenyl-4-trifluoromethyl-1H-pyrazolo[3,4-b]pyridine;

5-(1-Methyl-3-phenyl-4-trifluoromethyl-1H-pyrazolo[3,4-b]pyridin-6-yl)nicotinonitrile;

4-(1-Methyl-3-phenyl-4-trifluoromethyl-1H-pyrazolo[3,4-b]pyridin-6-yl)benzoic acid;

N,N-Dimethyl-4-(1-methyl-3-phenyl-4-trifluoromethyl-1H-pyrazolo[3,4-b]pyridin-6-yl)benzamide;

N,N-Dimethyl-3-(1-methyl-3-phenyl-4-trifluoromethyl-1H-pyrazolo[3,4-b]pyridin-6-yl)benzamide;

1-Methyl-6-(6-morpholin-4-ylpyridin-3-yl)-3-phenyl-4-trifluoromethyl-1H-pyrazolo[3,4-b]pyridine;

6-(6-Methoxypyridin-3-yl)-1-methyl-3-phenyl-4-trifluoromethyl-1H-pyrazolo[3,4-b]pyridine;

1-Methyl-3-phenyl-6-(6-pyrrolidin-1-ylpyridin-3-yl)-4-trifluoromethyl-1H-pyrazolo[3,4-b]pyridine;

1-Methyl-6-(2-methyl-5-trifluoromethyl-2H-pyrazol-3-yl)-3-phenyl-4-trifluoromethyl-1H-pyrazolo[3,4-b]pyridine;

6-Benzothiazol-5-yl-1-methyl-3-phenyl-4-trifluoromethyl-1H-pyrazolo[3,4-b]pyridine;

N,N-Dimethyl-4-(3-phenyl-4-trifluoromethyl-1H-pyrazolo[3,4-b]pyridin-6-yl)benzamide;

6-(4-Morpholin-4-ylphenyl)-3-phenyl-4-trifluoromethyl-1H-pyrazolo[3,4-b]pyridine;

6-(6-Morpholin-4-ylpyridin-3-yl)-3-phenyl-4-trifluoromethyl-1H-pyrazolo[3,4-b]pyridine;

6-(6-Methoxypyridin-3-yl)-3-phenyl-4-trifluoromethyl-1H-pyrazolo[3,4-b]pyridine;

6-(3-Morpholin-4-ylphenyl)-3-phenyl-4-trifluoromethyl-1H-pyrazolo[3,4-b]pyridine;

N-Methyl-3-(3-phenyl-4-trifluoromethyl-1H-pyrazolo[3,4-b]pyridin-6-yl)benzamide;

N-[3-(3-Phenyl-4-trifluoromethyl-1H-pyrazolo[3,4-b]pyridin-6-yl)phenyl]methanesulfonamide;

3-Phenyl-6-(3-piperidin-1-ylphenyl)-4-trifluoromethyl-1H-pyrazolo[3,4-b]pyridine;

2-Fluoro-N-methyl-5-(3-phenyl-4-trifluoromethyl-1H-pyrazolo[3,4-b]pyridin-6-yl)benzamide;

5-(3-Phenyl-4-trifluoromethyl-1H-pyrazolo[3,4-b]pyridin-6-yl)nicotinonitrile;

2-Fluoro-5-(1-methyl-3-phenyl-4-trifluoromethyl-1H-pyrazolo[3,4-b]pyridin-6-yl)benzoic acid;

2-Amino-5-(4-difluoromethyl-2-methyl-2H-pyrazolo[3,4-b]pyridin-6-yl)benzonitrile;

Dimethyl[4-(3-phenyl-4-trifluoromethyl-1H-pyrazolo[3,4-b]pyridin-6-yl)phenyl]amine;

4-(3-Phenyl-4-trifluoromethyl-1H-pyrazolo[3,4-b]pyridin-6-yl)phenylamine;

6-(4-Methoxyphenyl)-3-phenyl-4-trifluoromethyl-1H-pyrazolo[3,4-b]pyridine;

in the form of the base or of an acid-addition or base-addition salt.

A subject of the present invention is particularly compounds of formula (I) as defined above in which R$_2$ represents a group:

—CHF$_2$, except when R$_4$ located on the nitrogen alpha to R$_3$ represents a methyl group and R$_3$ represents a hydrogen atom, —COOH, or —CONHR$_5$, in which R$_5$ is as defined above, in the form of the base or of an acid-addition or base-addition salt.

A subject of the present invention is particularly compounds of formula (I) as defined above in which R$_1$ represents an aryl, pyridyl or pyrazolyl group, advantageously a phenyl group, optionally substituted with one or more substituents chosen from:

a halogen atom, advantageously a fluorine atom; and a group —COR$_{12}$, in which R$_{12}$ represents a hydroxyl group, in the form of the base or of an acid-addition or base-addition salt.

The last two subgroups defined above taken separately or in combination also form part of the invention.

Among the compounds of formula (I) that are subjects of the invention, mention may be made especially of the following compounds:

6-(4-Methoxyphenyl)-1-methyl-3-phenyl-4-trifluoromethyl-1H-pyrazolo[3,4-b]pyridine;
Dimethyl[3-(1-methyl-3-phenyl-4-trifluoromethyl-1H-pyrazolo[3,4-b]pyridin-6-yl)phenyl]amine;
N-Methy-3-(3-phenyl-4-trifluoromethyl-1H-pyrazolo[3,4-b]pyridin-6-yl)benzamide;
[4-(4-Difluoromethyl-3-phenyl-1H-pyrazolo[3,4-b]pyridin-6-yl)phenyl]pyrrolidin-1-ylmethanone;
4-Difluoromethyl-6-(1-methyl-1H-pyrazol-4-yl)-3-phenyl-1H-pyrazolo[3,4-b]pyridine;
4-Difluoromethyl-6-(3,5-dimethyl-1H-pyrazol-4-yl)-3-phenyl-1H-pyrazolo[3,4-b]pyridine;
4-Difluoromethyl-3-phenyl-6-(1H-pyrazol-4-yl)-1H-pyrazolo[3,4-b]pyridine;
4-Difluoromethyl-6-(6-methoxypyridin-3-yl)-3-phenyl-1H-pyrazolo[3,4-b]pyridine;
[3-(4-Difluoromethyl-3-phenyl-1H-pyrazolo[3,4-b]pyridin-6-yl)phenyl]pyrrolidin-1-ylmethanone;
4-Difluoromethyl-3-phenyl-6-(3-piperidin-1-ylphenyl)-1H-pyrazolo[3,4-b]pyridine;
6-(4-Amino-3-methoxyphenyl)-1H-pyrazolo[3,4-b]pyridine-4-carboxylic acid;
6-(4-Amino-3-methoxyphenyl)-1H-pyrazolo[3,4-b]pyridine-4-carboxylic acid;
6-(4-Amino-3-methoxyphenyl)-3-phenyl-1H-pyrazolo[3,4-b]pyridine-4-carboxylic acid methylamide;
6-(4-Amino-3-methoxyphenyl)-3-phenyl-1H-pyrazolo[3,4-b]pyridine-4-carboxylic acid amide; compound with trifluoroacetic acid;
6-(4-Amino-3-methoxyphenyl)-1H-pyrazolo[3,4-b]pyridine-4-carboxylic acid methylamide;
4-(4-Amino-3-methoxyphenyl)-1H-pyrazolo[3,4-b]pyridine-6-carboxylic acid methylamide;
6-(4-Amino-3-methoxyphenyl)-1H-pyrazolo[3,4-b]pyridine-4-carboxylic acid amide;
6-(4-Amino-3-methoxyphenyl)-3-phenyl-1H-pyrazolo[3,4-b]pyridine-4-carboxylic acid;
6-(4-Amino-3-methoxyphenyl)-2-methyl-2H-pyrazolo[3,4-b]pyridine-4-carboxylic acid;
6-(4-Amino-3-methoxyphenyl)-1-methyl-3-phenyl-1H-pyrazolo[3,4-b]pyridine-4-carboxylic acid;
6-(4-Amino-3-methoxyphenyl)-1-methyl-1H-pyrazolo[3,4-b]pyridine-4-carboxylic acid;
6-(4-Amino-3-methoxyphenyl)-2-methyl-2H-pyrazolo[3,4-b]pyridine-4-carboxylic acid amide;
5-(4-Carbamoyl-3-phenyl-1H-pyrazolo[3,4-b]pyridin-6-yl)-2-fluorobenzoic acid;
2-Amino-5-(4-carbamoyl-3-phenyl-1H-pyrazolo[3,4-b]pyridin-6-yl)benzoic acid;
6-(4-Amino-3-cyanophenyl)-3-phenyl-1H-pyrazolo[3,4-b]pyridine-4-carboxylic acid amide;
6-(4-Amino-3-cyanophenyl)-3-phenyl-1H-pyrazolo[3,4-b]pyridine-4-carboxylic acid amide;
6-(4-Amino-3-cyanophenyl)-2-methy-2H-pyrazolo[3,4-b]pyridine-4-carboxylic acid;
6-(4-Amino-3-cyanophenyl)-3-thiophen-2-yl-1H-pyrazolo[3,4-b]pyridine-4-carboxylic acid amide;
6-(4-Amino-3-cyanophenyl)-3-cyclopropyl-1H-pyrazolo[3,4-b]pyridine-4-carboxylic acid;
5-(4-Carbamoyl-1H-pyrazolo[3,4-b]pyridin-6-yl)-2-fluorobenzoic acid;
6-(3-Cyano-4-fluorophenyl)-3-phenyl-1H-pyrazolo[3,4-b]pyridine-4-carboxylic acid amide;
5-(4-Difluoromethyl-3-phenyl-1H-pyrazolo[3,4-b]pyridin-6-yl)-2-fluorobenzoic acid;
2-Fluoro-5-(3-phenyl-4-trifluoromethyl-1H-pyrazolo[3,4-b]pyridin-6-yl)benzonitrile;
2-Amino-5-(4-difluoromethyl-3-phenyl-1H-pyrazolo[3,4-b]pyridin-6-yl)benzonitrile;
2-Fluor-5-(3-phenyl-4-trifluoromethyl-1H-pyrazolo[3,4-b]pyridin-6-yl)benzoic acid;
2-Amino-5-(1-methyl-3-phenyl-4-trifluoromethyl-1H-pyrazolo[3,4-b]pyridin-6-yl)benzonitrile;
2-Amino-5-(1-methyl-3-phenyl-4-trifluoromethyl-1H-pyrazolo[3,4-b]pyridin-6-yl)benzonitrile;
6-(3-Carbamoyl-4-fluorophenyl)-3-pyridin-3-yl-1H-pyrazolo[3,4-b]pyridine-4-carboxylic acid amide;
5-(4-Difluoromethyl-2-methyl-2H-pyrazolo[3,4-b]pyridin-6-yl)-2-fluorobenzonitrile;
6-(1H-Indol-6-yl)-3-phenyl-4-trifluoromethyl-1H-pyrazolo[3,4-b]pyridine;
5-(3-Phenyl-4-trifluoromethyl-1H-pyrazolo[3,4-b]pyridin-6-yl)-1,3-dihydrobenzimidazol-2-one;
6-(4-Amino-3-cyanophenyl)-1H-pyrazolo[3,4-b]pyridine-4-carboxylic acid phenylamide;
6-(4-Amino-3-cyanophenyl)-1H-pyrazolo[3,4-b]pyridine-4-carboxylic acid (pyridin-2-ylmethyl)amide;
6-(4-Amino-3-cyanophenyl)-1H-pyrazolo[3,4-b]pyridine-4-carboxylic acid pyridin-2-ylamide;
6-(4-Amino-3-cyanophenyl)-1H-pyrazolo[3,4-b]pyridine-4-carboxylic acid pyridin-3-ylamide;
6-(4-Amino-3-cyanophenyl)-1H-pyrazolo[3,4-b]pyridine-4-carboxylic acid pyridin-4-ylamide;
5-(4-Difluoromethyl-2-methyl-2H-pyrazolo[3,4-b]pyridin-6-yl)-2-fluorobenzamide;
5-(4-Difluoromethyl-1-methyl-3-pyridin-4-yl-1H-pyrazolo[3,4-b]pyridin-6-yl)-2-fluorobenzonitrile;
2-Amino(2-methyl-3-phenyl-trifluoromethyl-2H-pyrazolo[3,4-b]pyridin-6-yl)benzonitrile;
6-(1H-Benzimidazol-5-yl)-1H-pyrazolo[3,4-b]pyridine-4-carboxylic acid phenylamide;
6-(1H-Benzimidazol-5-yl)-1H-pyrazolo[3,4-b]pyridine-4-carboxylic acid pyridin-2-ylamide;
6-(1H-Benzimidazol-5-yl)-1H-pyrazolo[3,4-b]pyridine-4-carboxylic acid (pyridin-3-ylmethyl)amide;
6-(2-Oxo-2,3-dihydro-1H-benzimidazol-5-yl)-1H-pyrazolo[3,4-b]pyridine-4-carboxylic acid phenylamide;
2-Amino-5-(4-difluoromethyl-1-methyl-1H-pyrazolo[3,4-b]pyridin-6-yl)benzonitrile;

3-(4-Difluoromethyl-1-methyl-1H-pyrazolo[3,4-b]pyridin-6-yl)benzonitrile;
4-(4-Difluoromethyl-1-methyl-1H-pyrazolo[3,4-b]pyridin-6-yl)phenylamine;
2-Amino-5-[2-(2-dimethylaminoethyl)-3-phenyl-4-trifluoromethyl-2H-pyrazolo[3,4-b]pyridin-6-yl]benzonitrile;
2-Amino-5-(4-difluoromethyl-1H-pyrazolo[3,4-b]pyridin-6-yl)benzonitrile;
2-Amino-5-[1-(2-dimethylaminoethyl)-3-phenyl-4-trifluoromethyl-1H-pyrazolo[3,4-b]pyridin-6-yl]benzonitrile;
2-Amino-5-[2-(2-morpholin-4-ylethyl)-3-phenyl-4-trifluoromethyl-2H-pyrazolo[3,4-b]pyridin-6-yl]benzonitrile;
2-Methoxy-5-(1-methyl-3-phenyl-4-trifluoromethyl-1H-pyrazolo[3,4-b]pyridin-6-yl)nicotinonitrile;
2-Amino-5-(4-difluoromethyl-1-methyl-3-phenyl-1H-pyrazolo[3,4-b]pyridin-6-yl)benzonitrile;
4-(4-Difluoromethyl-1-methyl-3-phenyl-1H-pyrazolo[3,4-b]pyridin-6-yl)phenylamine;
[3-(4-Difluoromethyl-1-methyl-3-phenyl-1H-pyrazolo[3,4-b]pyridin-6-yl)phenyl]dimethylamine;
2-Amino-5-[3-phenyl-1-(2-piperidin-1-ylethyl)-4-trifluoromethyl-1H-pyrazolo[3,4-b]pyridin-6-yl]benzonitrile;
Dimethyl{3-[3-phenyl-1-(2-piperidin-1-ylethyl)-4-trifluoromethyl-1H-pyrazolo[3,4-b]pyridin-6-yl]phenyl}amine;
2-Amino-5-[4-difluoromethyl-2-(2-dimethylaminoethyl)-2H-pyrazolo[3,4-b]pyridin-6-yl]benzonitrile;
2-Amino-5-[4-difluoromethyl-2-(2-morpholin-4-ylethyl)-2H-pyrazolo[3,4-b]pyridin-6-yl]benzonitrile;
2-Amino-5-[4-difluoromethyl-1-(2-dimethylaminoethyl)-3-phenyl-1H-pyrazolo[3,4-b]pyridin-6-yl]benzonitrile;
2-(2-Morpholin-4-ylethyl)-6-(3-morpholin-4-ylmethylphenyl)-4-trifluoromethyl-2H-pyrazolo[3,4-b]pyridine;
Dimethyl{3-[1-(2-morpholin-4-ylethyl)-4-trifluoromethyl-1H-pyrazolo[3,4-b]pyridin-6-yl]phenyl}amine;
5-[1-(2-Morpholin-4-ylethyl)-4-trifluoromethyl-1H-pyrazolo[3,4-b]pyridin-6-yl]nicotinonitrile;
5-[1-(2-Morpholin-4-ylethyl)-4-trifluoromethyl-1H-pyrazolo[3,4-b]pyridin-6-yl]nicotinamide;
2-Amino-5-(2-methyl-4-trifluoromethyl-2H-pyrazolo[3,4-b]pyridin-6-yl)benzonitrile;
1-Methyl-6-(3-morpholin-4-ylmethylphenyl)-4-trifluoromethyl-1H-pyrazolo[3,4-b]pyridine;
2-Amino-5-(1-methyl-4-trifluoromethyl-1H-pyrazolo[3,4-b]pyridin-6-yl)benzonitrile;
Dimethyl[3-(1-methyl-4-trifluoromethyl-1H-pyrazolo[3,4-b]pyridin-6-yl)phenyl]amine;
Dimethyl[3-(3-phenyl-2-propyl-4-trifluoromethyl-2H-pyrazolo[3,4-b]pyridin-6-yl)phenyl]amine;
2-Amino-5-[4-difluoromethyl-2-(2-piperidin-1-ylethyl)-2H-pyrazolo[3,4-b]pyridin-6-yl]benzonitrile;
2-Amino-5-(4-difluoromethyl-3-pyridin-3-yl-1H-pyrazolo[3,4-b]pyridin-6-yl)benzonitrile;
2-Amino-5-(4-difluoromethyl-2-propyl-2H-pyrazolo[3,4-b]pyridin-6-yl)benzonitrile;
2-Amino-5-(4-difluoromethyl-3-pyridin-4-yl-1H-pyrazolo[3,4-b]pyridin-6-yl)benzonitrile;
1-Methyl-6-(3-morpholin-4-ylmethylphenyl)-3-pyridin-3-yl-4-trifluoromethyl-1H-pyrazolo[3,4-b]pyridine;
2-Amino-5-[4-difluoromethyl-3-(3-methoxyphenyl)-1H-pyrazolo[3,4-b]pyridin-6-yl]benzonitrile;
2-Amino-5-(2-propyl-4-trifluoromethyl-2H-pyrazolo[3,4-b]pyridin-6-yl)benzonitrile;
6-(3-Morpholin-4-ylmethylphenyl)-2-propyl-4-trifluoromethyl-2H-pyrazolo[3,4-b]pyridine;
Dimethyl[3-(2-propyl-4-trifluoromethyl-2H-pyrazolo[3,4-b]pyridin-6-yl)phenyl]amine;
6-(3-Morpholin-4-ylmethylphenyl)-1-propyl-4-trifluoromethyl-1H-pyrazolo[3,4-b]pyridine;
6-(4-Methoxyphenyl)-1-propyl-4-trifluoromethyl-1H-pyrazolo[3,4-b]pyridine;
5-[3-(3-Methoxyphenyl)-1-methyl-4-trifluoromethyl-1H-pyrazolo[3,4-b]pyridin-6-yl]nicotinonitrile;
3-(3-Methoxyphenyl)-1-methyl-6-(3-morpholin-4-ylmethylphenyl)-4-trifluoromethyl-1H-pyrazolo[3,4-b]pyridine;
{3-[3-(3-Methoxyphenyl)-1-methyl-4-trifluoromethyl-1H-pyrazolo[3,4-b]pyridin-6-yl]phenyl}dimethylamine;
3-(3-Methoxyphenyl)-6-(4-methoxyphenyl)-1-methyl-4-trifluoromethyl-1H-pyrazolo[3,4-b]pyridine.

It should be noted that the above compounds have been named according to the IUPAC nomenclature, by means of the ACDLABS 10.0 ACD/name software (Advanced Chemistry development) or the AutoNom software (Beilstein Informations system).

In the text hereinbelow, the term "protecting group (P)" means a group that can, firstly, protect a reactive function such as a hydroxyl or an amine during a synthesis and, secondly, regenerate the intact reactive function at the end of the synthesis. Examples of protecting groups and also of protection and deprotection methods are given in *Protective Groups in Organic Synthesis*, Greene et al., 3rd Edition (John Wiley & Sons, Inc., New York).

In accordance with the invention, the compounds of general formula (I) may be prepared according to the process that follows.

The compound of formula (IV) when $R_2$ represents a group —$CF_3$ is obtained via methods known in the literature from the 2-aminopyrazole (III) and the 4,4,4-trifluoroacetoacetate (II), according to the following reaction scheme described in the *Polish Journal of Chemistry*, 1983, 57, 789.

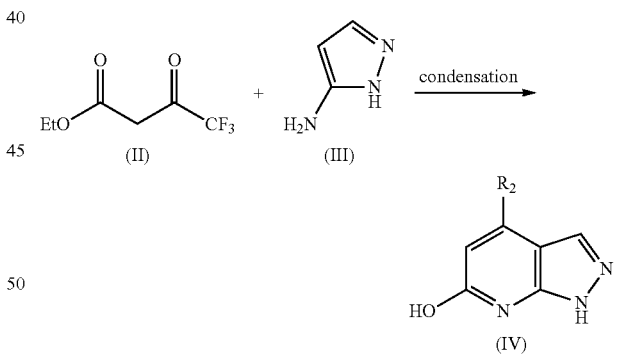

The compound of formula (IV) when $R_2$ represents a —$CHF_2$ group is obtained via a method similar to that described previously by condensation of the 2-aminopyrazole (III) and 4,4-difluoroacetoacetate.

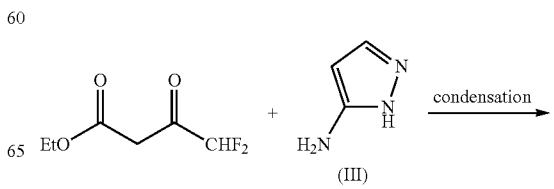

-continued

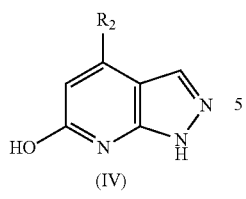

The compound of formula (XII) in which $R_2$ represents a group —$CHF_2$ or —$CF_3$ is obtained by chlorination in the presence of $POCl_3$ of the compound of formula (IV) in which $R_2$ represents a group —$CHF_2$ or —$CF_3$.

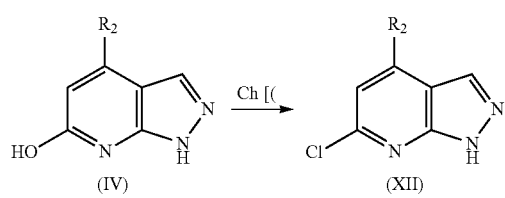

The compound of formula (VI) in which $R_2$ represents a group —$CF_3$ and $R_3$ is a phenyl is obtained via methods known in the literature from 3-phenyl-1H-pyrazol-5-amine (V) and ethyl 4,4,4-trifluoro-3-oxobutanoate, according to the following reaction scheme described in the *Polish Journal of Chemistry*, 1983, 57, 789.

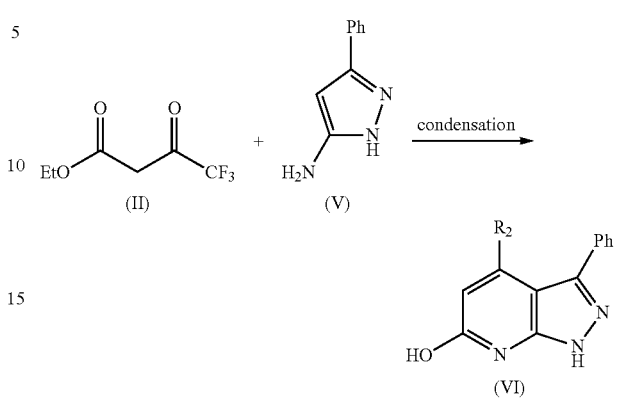

The compound of formula (VI) in which $R_2$ represents a —$CHF_2$ group is obtained via a method similar to that described previously from 3-phenyl-1H-pyrazol-5-amine (V) and ethyl 4,4-difluoro-3-oxobutanoate.

Scheme 1 presents a route for obtaining compounds of formula (I) in which $R_1$ is as defined previously, and $R_2$ represents a group —$CF_3$ or —$CHF_2$.

Scheme 1 (Method 1):

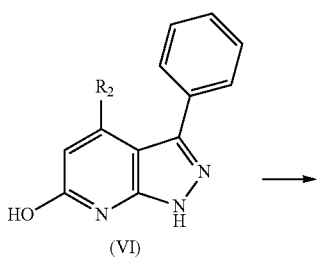

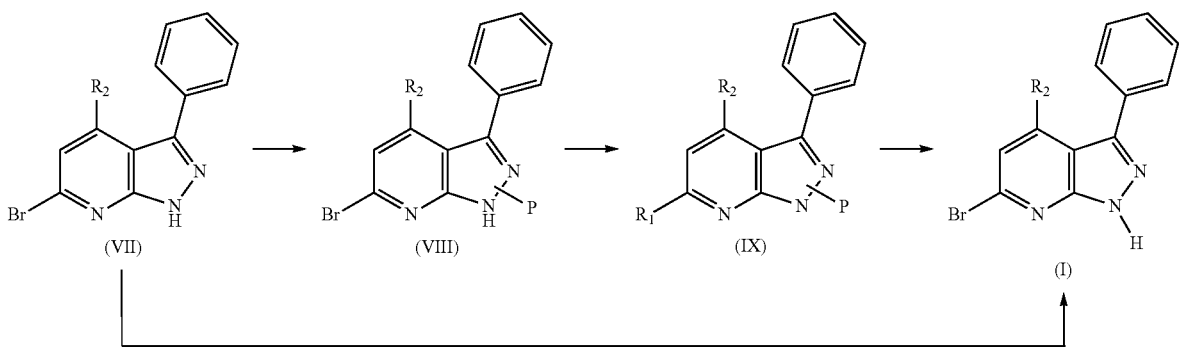

The compound of formula (VI) is subjected to a bromination reaction in the presence of POBr$_3$ in order to obtain the compound of formula (VII). The compound of formula (VII) is subjected to an alkylation reaction in the presence of a protecting group P in order to obtain the compound of formula (VIII). The compound of formula (VIII) is subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (IX). The compound of formula (IX) is subjected to a deprotection reaction in order to obtain the compounds of formula (I) in which $R_1$ is as defined previously, and $R_2$ represents a group —CF$_3$ or —CHF$_2$.

The compound of formula (VII) may optionally be subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (I) in which $R_1$ is as defined previously, and $R_2$ represents a group —CF$_3$ or —CHF$_2$.

Scheme 2 presents a route for obtaining compounds of formula (I) in which $R_1$ and $R_4$ are as defined previously with the exception of a hydrogen atom.

Scheme 2 (Method 2):

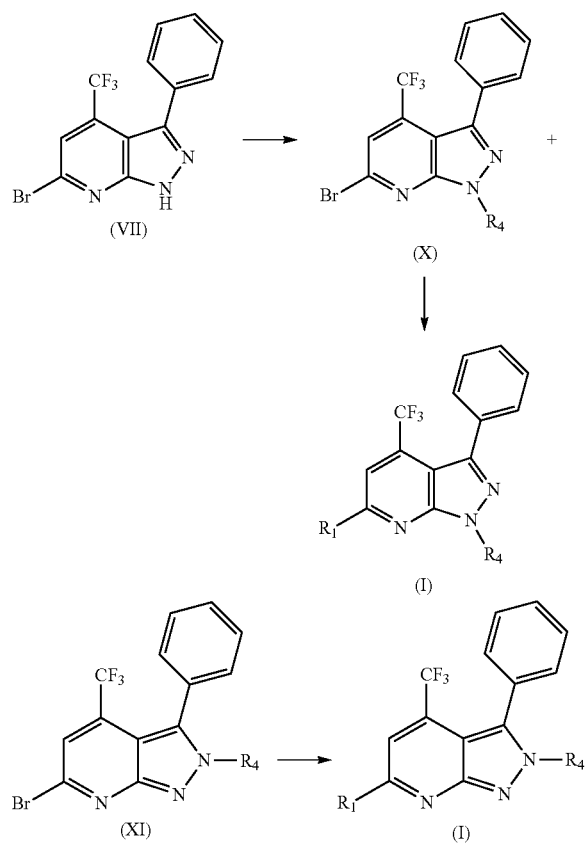

The compound of formula (VII) is subjected to an alkylation reaction in the presence of a base and a halogenated derivative of formula $R_4$—X in order to obtain the compounds of formulae (X) and (XI). The compounds of formulae (X) and (XI) are subjected separately, in the presence of a palladium catalyst, a ligand and a base, to a reaction with phenylboronic or heteroarylboronic derivatives or phenylboronate esters or heteroarylboronate esters according to a Suzuki coupling, in order to obtain the compounds of formula (I) in which $R_1$ and $R_4$ are as defined previously.

Scheme 3 presents a route for obtaining compounds of formula (I) in which $R_2$ represents a group —CHF$_2$ or —CF$_3$ and $R_1$ and $R_4$ are as defined previously, with the exception that $R_4$ represents a hydrogen atom.

Scheme 3 (Method 3):

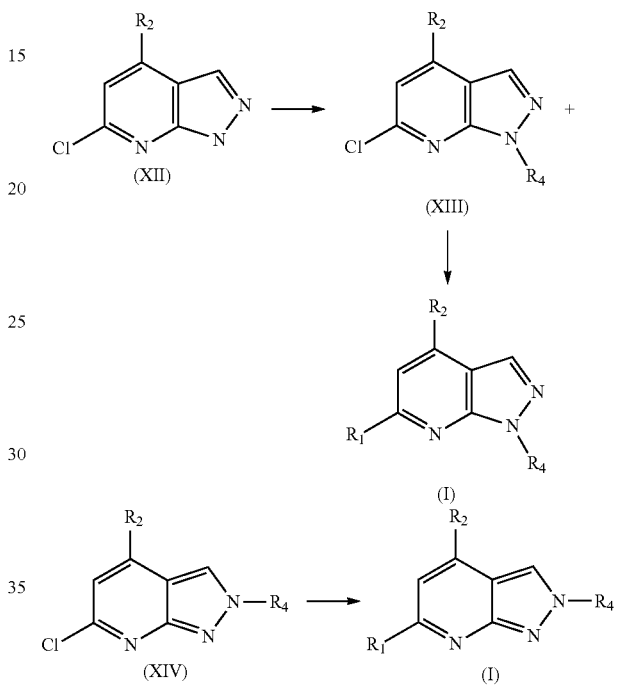

The compound of formula (XII) is subjected to an alkylation reaction in the presence of a halogenated derivative of formula $R_4$—X in order to obtain the compounds of formulae (XIII) and (XIV). The compounds of formulae (XIII) and (XIV) are separately subjected, in the presence of a palladium catalyst, a ligand and a base such as caesium carbonate, to a reaction with phenylboronic or heteroarylboronic derivatives or phenylboronate esters or heteroarylboronate esters according to a Suzuki coupling, in order to obtain the compound of formula (I) in which $R_2$ represents a group —CHF$_2$ or —CF$_3$ and $R_1$ and $R_4$ are as defined previously.

Scheme 4 presents a route for obtaining compounds of formula (I) in which $R_2$ represents a group —CHF$_2$ or —CF$_3$, $R_3$ and $R_4$ represent a hydrogen atom and $R_1$ is as defined previously.

Scheme 4 (Method 4):

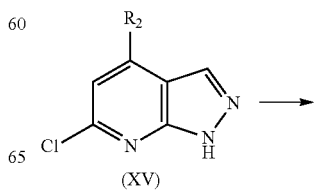

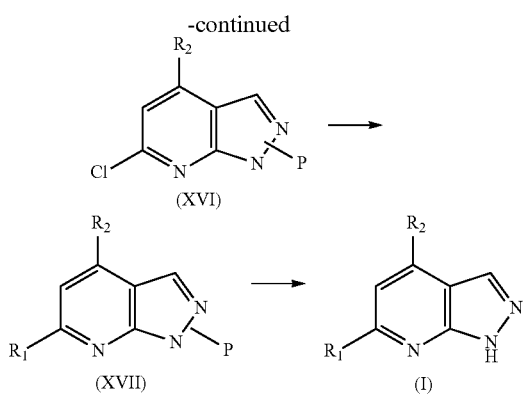

The compound of formula (XV) is subjected to an alkylation reaction in the presence of a protecting group P in order to obtain the compound of formula (XVI). The compound of formula (XVI) is subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (XVII). The compound of formula (XVII) is then subjected to a deprotection reaction in order to obtain the compound of formula (I) in which $R_2$ represents a group —$CHF_2$ or —$CF_3$ and $R_1$ is as defined previously.

Scheme 5 presents a route for obtaining compounds of formula (I) in which $R_2$ represents a group —$CHF_2$ or —$CF_3$ and $R_1$, $R_3$ and $R_4$ are as defined previously, with the exception that $R_3$ and $R_4$ represent a hydrogen atom.

Scheme 5 (Method 5):

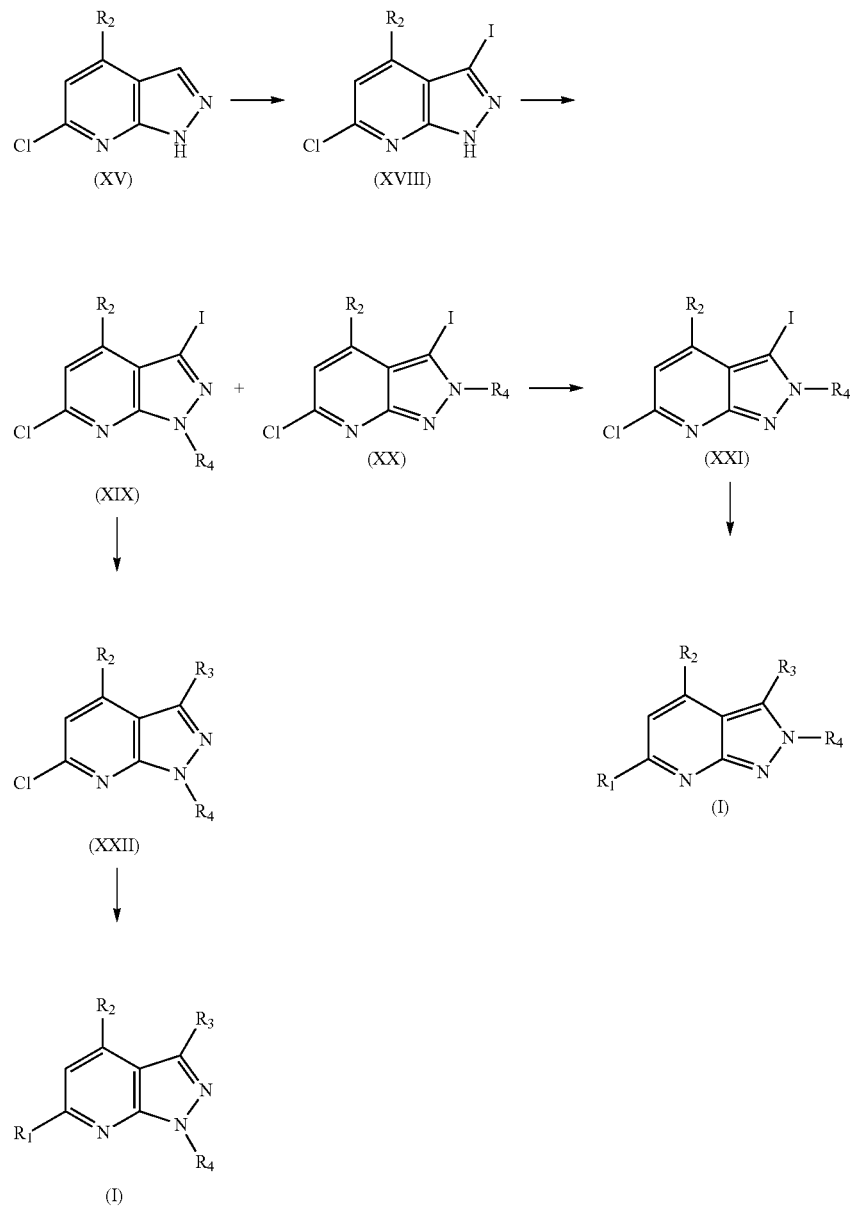

The compound of formula (XV) is subjected to an iodination reaction in the presence of N-iodosuccinimide in order to obtain the compound of formula (XVIII). The compound of formula (XVIII) is then subjected to an alkylation reaction in the presence of a halogenated derivative of formula $R_4$—X in order to obtain the compounds of formulae (XIX) and (XX). The compounds of formulae (XIX) and (XX) are subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compounds of formulae (XXI) and (XXII). The compounds of formulae (XXI) and (XXII) are subjected separately, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (I) in which $R_2$ represents a group —$CHF_2$ or —$CF_3$ and $R_1$, $R_3$ and $R_4$ are as defined previously, with the exception of a hydrogen atom.

Scheme 6 presents a route for obtaining compounds of formula (I) in which $R_2$ represents a group —$CHF_2$ or —$CF_3$ and $R_1$ and $R_3$ are as defined previously, with the exception of a hydrogen atom.

Scheme 6 (Method 6):

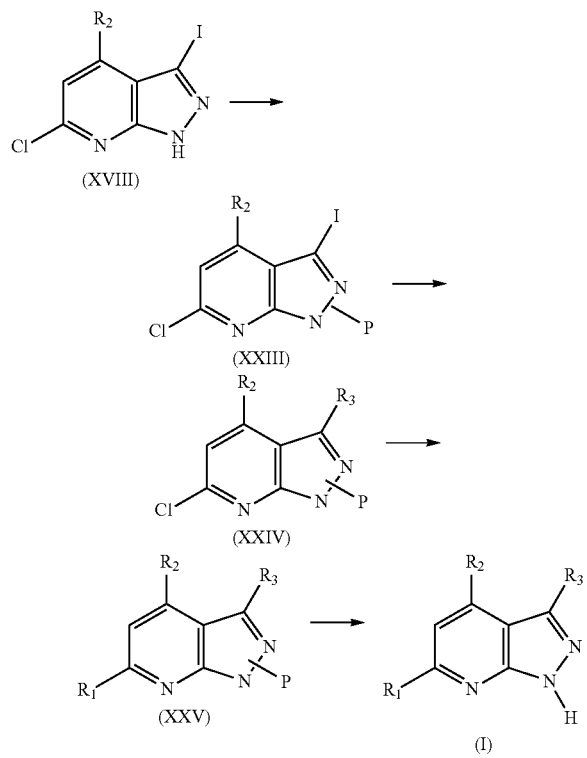

The compound of formula (XVIII) is subjected to an alkylation reaction in the presence of a protecting group P in order to obtain the compound of formula (XXIII). The compound of formula (XXIII) is subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (XXIV). The compound of formula (XXIV) is subjected, in the presence of a palladium catalyst, a ligand and a base, to a reaction with phenylboronic or heteroarylboronic derivatives or phenylboronate esters or heteroarylboronate esters according to a Suzuki coupling, in order to obtain the compound of formula (XXV). The compound of formula (XXV) is then subjected to a protection reaction in order to obtain the compound of formula (I) in which $R_2$ represents a group —$CHF_2$ or —$CF_3$ and $R_1$ and $R_3$ are as defined previously, with the exception that $R_3$ and $R_4$ represent a hydrogen atom.

Scheme 7 presents a route for obtaining compounds of formula (I) in which $R_2$ is as defined previously, with the exception of a group —$CHF_2$ or —$CF_3$, and $R_1$, $R_3$ and $R_4$ are as defined previously.

Scheme 7 (Method 7):

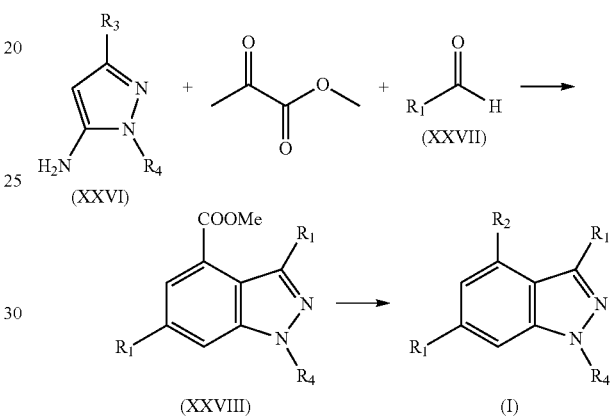

The compound of formula (XXVI) is subjected to a condensation reaction with the compound of formula (XXVII) and methyl 2-oxopropanoate in order to obtain the compound of formula (XXVIII). The compound of formula (XXVIII) is subjected to a saponification reaction or to substitution with an amine in order to obtain the compound of formula (I) in which $R_2$ is as defined previously, except for a group —$CHF_2$ or —$CF_3$, and $R_1$, $R_3$ and $R_4$ are as defined previously.

In the preceding schemes, the starting compounds, the reagents and the intermediates, when their preparation method is not described, are commercially available or described in the literature, or alternatively may be prepared according to methods that are described therein or that are known to those skilled in the art.

According to another of its aspects, a subject of the invention is also the compounds of formulae (II) to (XXVIII) defined above. These compounds are useful as intermediates for synthesizing the compounds of formula (I).

The examples that follow describe the preparation of certain compounds in accordance with the invention. These examples are not limiting and serve merely to illustrate the present invention. The numbers of the compounds exemplified refer to those given in the table below, which illustrates the chemical structures and physical properties of a number of compounds according to the invention.

The present invention is also illustrated below in two figures such that:

FIG. 1: in vitro angiogenesis (length of pseudotubules) of HUVEC cells stimulated with FGF-2 in the absence or presence of FGF-R antagonists.

Figure 2:
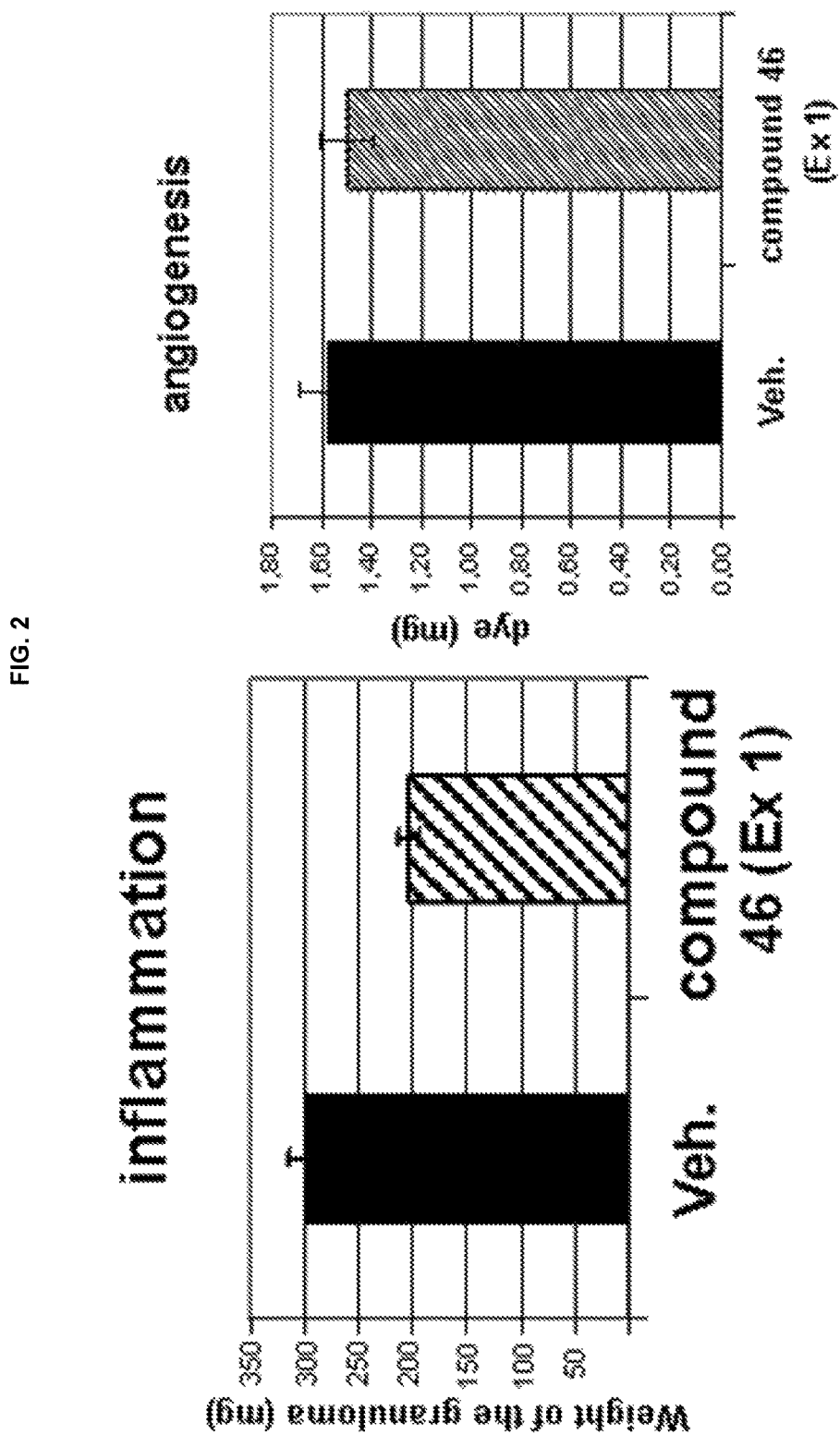

FIG. 2: Effect of FGF-R antagonists in a model of inflammatory angiogenesis on the dry weight of skin (weight of the granuloma) or on their content of carmine red dye (dye).

The following abbreviations and empirical formulae are used:

AcOH: acetic acid
PTSA: para-toluenesulfonic acid
DME: ethylene glycol dimethyl ether
DMF: N,N-dimethylformamide
DMSO: dimethyl sulfoxide
g: gram
(M)Hz: (mega)Hertz
mL: milliliter
POBr$_3$: dibromophosphanyl hypobromite
TBAF: tetrabutylammonium fluoride
TFA: trifluoroacetic acid
THF: tetrahydrofuran In the examples that follow:
the NMR analyses were performed on Brüker Avance 250 MHz, 300 MHz, 400 MHz and 600 MHz machines. The proton magnetic resonance spectrum ($^1$H NMR), as described below, are recorded at 400 MHz or 600 MHz in DMSO-d$_6$, using the DMSO-d$_6$ peak as reference. The chemical shifts □ are expressed in parts per million (ppm). The signals observed are expressed as follows: s=singlet; d=doublet; t=triplet; m=mass or broad singlet; H=proton (for the rotamers, H$_M$ and H$_m$ are noted with reference to the major or minor isomers M and m, respectively).

the melting points were measured on a Büchi B-545 machine.

the mass spectrometry analyses were performed on an Alliance 2695 machine (UV: PDA 996, MS: ZQ (simple Quad) ZQ2), Waters UPLC Acquity (UV: Acquity PDA, MS: SQD (simple Quad) SQW)

Example 1: (Compound 46)

5-(4-Carbamoyl-3-phenyl-1H-pyrazolo[3,4-b]pyridin-6-yl)-2-fluorobenzoic acid

To 5 ml of a 0.3 M solution in ethanol of 3-phenyl-1H-pyrazol-5-amine in a sealed tube are added 5 ml of a 0.3 M solution in ethanol of 2-fluoro-5-formylbenzoic acid and 1.5 mmol of ethyl 2-oxopropanoate at room temperature under an inert atmosphere of nitrogen. The tube is sealed and maintained at a temperature of 75° C. for 18 hours. The capsule is removed and heating is continued for 4 hours at 60° C. The reaction medium is then concentrated under reduced pressure. The residue is taken up in a sealed tube with a 7 N solution of ammonia in methanol. The medium is then heated for 3 days at 80° C. and then concentrated under reduced pressure. After purification by column chromatography on C-18 reverse-phase silica gel, eluting with an acetonitrile/H$_2$O/0.1% TFA mixture, 23.7 mg of a lyophilizate are obtained.

MH$^+$: 377

$^1$H NMR (600 MHz, DMSO-d$_6$): □□□□14.10 (s, 1H), 13.43 (s (broad), 1H), 8.79 (dd, J$_A$=7.2 Hz, J$_B$=2.3 Hz, 1H), 8.50 (m, 1H), 8.14 (s, 1H), 7.87 (s, 1H), 7.80 (s, 1H), 7.70 (dd, J$_A$=7.8 Hz, J$_B$=1.6 Hz, 1H), 7.51 (m, 1H), 7.46 (m, 2H), 7.41 (m, 1H)

Example 2: (Compound 38)

6-(4-Amino-3-methoxyphenyl)-1H-pyrazolo[3,4-b]pyridine-4-carboxylic acid 6-(4-Amino-3-methoxyphenyl)-1H-pyrazolo[3,4-b]pyridine-4-carboxylic acid To 20 g (0.12 mol) of 3-hydroxy-4-nitrobenzaldehyde in 200 ml of anhydrous DMF are added 42 g (0.13 mol) of caesium carbonate. The solution obtained is ultrasonicated for 5 minutes, and 9.4 ml (0.29 mol) of methyl iodide are then added. The reaction medium is heated at 80° C. for 18 hours and then diluted with ethyl acetate. The organic phase is washed with saturated aqueous sodium chloride solution, dried over magnesium sulfate and then concentrated under reduced pressure. The residue is recrystallized from 300 ml of a hot ½ DMF/ethanol mixture. The crystals formed are filtered off, rinsed with cold ethanol and with hexane, and then dried under reduced pressure. 12.1 g of a solid are obtained.

To 2 g (11 mmol) of 3-methoxy-4-nitrobenzaldehyde in 150 ml of anhydrous ethanol in a sealed tube are added 1.17 g (13.3 mmol) of pyruvic acid and 1.1 g (15.5 mmol) of 1H-pyrazol-5-amine. The reaction medium is heated at 80° C. for 18 hours and then concentrated under reduced pressure. The residue is dissolved in 160 ml of a 3/1 DMSO/methanol mixture, to which are added 80 g of Dowex 1×8-400 resin. The reaction medium is stirred at room temperature for 1 hour and then filtered. The resin is rinsed several times with DMSO and then with methanol, and finally treated for 30 minutes in a 10% solution of TFA in methanol. After filtration, the organic phase is concentrated under reduced pressure. The residue obtained is taken up in 100 ml of ethanol and 40 ml of acetic acid. 300 mg of zinc powder are added. The reaction medium is stirred at room temperature. 1 g of zinc powder are added after 15 minutes. The reaction medium is filtered and then concentrated under reduced pressure. After purification by column chromatography on C-18 reverse-phase silica gel, eluting with an acetonitrile/H$_2$O/0.1% TFA mixture, 23.7 mg of a lyophilizate are obtained.

MH$^+$: 285

$^1$H NMR (600 MHz, DMSO-d$_6$): □ 8.28 (s, 1H), 8.08 (s, 1H), 7.67 (d, J=2.1 Hz, 1H), 7.59 (dd, J$_A$=8.4 Hz, J$_B$=1.9 Hz, 1H), 6.77 (d, J=8.2 Hz, 1H), 3.91 (s, 3H)

Example 3: (Compound 53)

5-[4-(Difluoromethyl)-3-phenyl-1H-pyrazolo[3,4-b]pyridin-6-yl)-2-fluorobenzoic acid 4-(difluoromethyl)-3-phenyl-1H-indazol-6-ol To 2.1 g (12.7 mmol) of ethyl 4,4-difluoro-3-oxobutanoate in 16 ml of a 1/1 AcOH/H$_2$O mixture are added 2 g (12.5 mmol) of 3-phenyl-1H-pyrazol-5-amine. The reaction medium is heated at 90° C. for 18 hours. The medium is cooled and the precipitate obtained is filtered off, washed with aqueous 20% acetic acid solution and then dried under reduced pressure. 2.5 g of a solid are obtained.

MH$^+$: 262

6-bromo-4-(difluoromethyl)-3-phenyl-1H-pyrazolo[3,4-b]pyridine

To 1 g (3.8 mmol) of 4-(difluoromethyl)-3-phenyl-1H-indazol-6-ol in 20 ml of toluene are added 3.1 g (10.8 mmol) of POBr$_3$. The reaction medium is heated at 90° C. for 18 hours. The reaction medium is concentrated under reduced pressure. The residue obtained is purified by column chromatography on silica gel, eluting with a 4/1 hexane/ethyl acetate mixture. 620 mg of a solid are obtained.

MH$^+$: 324

5-[4-(Difluoromethyl)-3-phenyl-1H-pyrazolo[3,4-b]pyridin-6-yl]-2-fluorobenzoic acid To 78 mg (0.24 mmol) of 6-bromo-4-(difluoromethyl)-3-phenyl-1H-pyrazolo[3,4-b]pyridine in 4 ml of a 4/1 THF/water mixture are added 92 mg (0.43 mmol) of [3-(ethoxycarbonyl)-4-fluorophenyl]boronic acid, 35 mg (0.03 mmol) of tetrakis(triphenylphosphine)palladium and 261 mg (0.8 mmol) of caesium carbonate, under an inert atmosphere of argon. The reaction medium is heated at 150° C. for 60 minutes by microwave. The organic phase is separated out by settling of the phases, diluted with THF, washed with saturated aqueous sodium chloride solution and concentrated under reduced pressure. After purification by column chromatography on C-18 reverse-phase silica gel, eluting with an acetonitrile/H$_2$O/0.1% TFA mixture, 12.3 mg of a lyophilizate are obtained.

MH$^+$: 384

$^1$H NMR (600 MHz, DMSO-d$_6$): □ 14.31 (s, 1H), 8.76 (dd, J$_A$=7.2 Hz, J$_B$=2.3 Hz, 1H), 8.47 (m, 1H), 8.04 (s, 1H), 7.67 (d, J$_A$=7.9 Hz, 2H), 7.51 (m, 4H), 7.33 (t, J$_A$=54.6 Hz, 1H)

Example 4: (Compound 56)

2-Fluoro-5-[3-phenyl-4-(trifluoromethyl)-1H-pyrazolo[3,4-b]pyridin-6-yl]benzoic acid

3-phenyl-4-(trifluoromethyl)-1H-pyrazolo[3,4-b]pyridin-6-ol

To 2.1 g (11.4 mmol) of ethyl 4,4,4-trifluoro-3-oxobutanoate in 16 ml of a 1/1 AcOH/H$_2$O mixture are added 2 g (12.5 mmol) of 3-phenyl-1H-pyrazol-5-amine. The reaction medium is heated at 90° C. for 18 hours. The medium is cooled and the precipitate obtained is filtered off, washed with aqueous 20% acetic acid solution and then dried under reduced pressure. 2.5 g of a solid are obtained.

MH$^+$: 280

6-bromo-3-phenyl-4-(trifluoromethyl)-1H-pyrazolo[3,4-b]pyridine

To 1 g (3.8 mmol) of 3-phenyl-4-(trifluoromethyl)-1H-pyrazolo[3,4-b]pyridin-6-ol in 20 ml of toluene are added 3.1 g (10.8 mmol) of POBr$_3$. The reaction medium is heated at 90° C. for 18 hours. The reaction medium is concentrated under reduced pressure and then purified by column chromatography on silica gel, eluting with a 4/1 hexane/ethyl acetate mixture. 338 mg of a solid are obtained.

MH$^+$: 306

2-Fluoro-5-[3-phenyl-4-(trifluoromethyl)-1H-pyrazolo[3,4-b]pyridin-6-yl]benzoic acid To 103 mg (0.33 mmol) of 6-bromo-3-phenyl-4-(trifluoromethyl)-1H-pyrazolo[3,4-b]pyridine in 4 ml of a 4/1 THF/water mixture are added 187 mg (0.88 mmol) of [3-(ethoxycarbonyl)-4-fluorophenyl]boronic acid, 41 mg (0.035 mmol) of tetrakis(triphenylphosphine)palladium and 293 mg (0.9 mmol) of caesium carbonate, under an inert atmosphere of argon. The reaction medium is heated at 150° C. for 60 minutes by microwave. The organic phase is separated out by settling of the phases, diluted with THF, washed with saturated aqueous sodium chloride solution and concentrated under reduced pressure. The residue obtained is purified by column chromatography on C-18 reverse-phase silica gel, eluting with an acetonitrile/H$_2$O/0.1% TFA mixture. The solid obtained is taken up in a 1/1 DMF/NaOH (1N) mixture and stirred for 1 hour at room temperature. After purification by column chromatography on C-18 reverse-phase silica gel, eluting with an acetonitrile/H$_2$O/0.1% TFA mixture, 34 mg of a lyophilizate are obtained.

MH$^+$: 402

$^1$H NMR (600 MHz, DMSO-d$_6$): □ 14.51 (s, 1H), 13.51 (s (broad), 1H), 8.80 (dd, J$_A$=7.1 Hz, J$_B$=2.4 Hz, 1H), 8.51 (m, 1H), 8.17 (s, 1H), 7.51 (m, 6H)

Example 5: (Compound 61)

N,N-Dimethyl-4-[3-phenyl-4-(trifluoromethyl)-1H-pyrazolo[3,4-b]pyridin-6-yl]aniline

6-bromo-3-phenyl-4-(trifluoromethyl)-1-{[2-(trimethylsilyl)ethoxy]methyl}-1H-pyrazolo[3,4-b]pyridine To 10 g (29 mmol) of 6-bromo-3-phenyl-4-(trifluoromethyl)-1H-pyrazolo[3,4-b]pyridine in 100 ml of anhydrous DMF, under an inert atmosphere of nitrogen, are added 7.3 g (43.8 mmol) of [2-(chloromethoxy)ethyl](trimethyl)silane and 6.11 ml (43.8 mmol) of triethylamine, at room temperature. The reaction medium is stirred for 2 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/ethyl acetate mixture. 13.3 g of a colourless oil are obtained.

MH$^+$: 472

N,N-dimethyl-4-[3-phenyl-4-(trifluoromethyl)-1-([2-(trimethylsilyl)ethoxy]methyl-1H-pyrazolo[3,4-b]pyridin-6-yl]aniline To 0.4 g (0.85 mmol) of 6-bromo-3-phenyl-4-(trifluoromethyl)-1-{[2-(trimethylsilyl)ethoxy]methyl}-1H-pyrazolo[3,4-b]pyridine in 4 ml of a 1/1 DME/H$_2$O mixture under an inert atmosphere of argon are added 0.168 g (1.02 mmol) of [4-(dimethylamino)phenyl]boronic acid, 0.63 g (2.54 mmol) of potassium phosphate dihydrate and 19.6 mg (0.02 mmol) of tetrakis(triphenylphosphine)palladium. The reaction medium is heated at 150° C. for 15 minutes by microwave. The reaction medium is hydrolysed with water and then extracted with ethyl acetate. The organic phase is dried over sodium sulfate and then concentrated under reduced pressure. The residue obtained is purified by column chromatography on silica gel, eluting with a heptane/dichloromethane mixture. 380 mg of a yellow solid are obtained.
MH+: 513
Melting point: 98° C.

N,N-dimethyl-4-[3-phenyl-4-(trifluoromethyl)-1H-pyrazolo[3,4-b]pyridin-6-yl]aniline To 0.38 g (0.74 mmol) of N,N-dimethyl-4-[3-phenyl-4-(trifluoromethyl)-1-{[2-(trimethylsilyl)ethoxy]methyl}-1H-pyrazolo[3,4-b]pyridin-6-yl]aniline are added 3.56 ml (3.56 mmol) of a 1N solution of TBAF in THF at room temperature under an inert atmosphere. The reaction medium is refluxed for 8 hours, a further 1 ml of the 1N solution of TBAF in THF is added, and heating is continued for 8 hours. This step is repeated three times and the reaction medium is then hydrolysed with water and concentrated under reduced pressure. The residue is taken up in an H$_2$O/methanol mixture. The precipitate obtained is filtered off, rinsed with water and dried at 50° C. under reduced pressure for 18 hours. 260 mg of a yellow solid are obtained.
MH+: 383
Melting point: 227° C.
$^1$H NMR (400 MHz, DMSO-d$_6$): □□□14.16 (br. s., 1H) 8.14 (d, J=9.1 Hz, 2H) 7.96 (s, 1H) 7.44-7.54 (m, 5H) 6.85 (d, J=9.1 Hz, 2H) 3.03 (s, 6H)

Example 6: (Compound 57)

2-Amino-5-[1-methyl-3-phenyl-4-(trifluoromethyl)-1H-pyrazolo[3,4-b]pyridin-6-yl]benzonitrile 6-bromo-1-methyl-3-phenyl-4-trifluoromethyl)-1H-pyrazolo[3,4-b]pyridine To 10 g (29 mmol) of 6-bromo-3-phenyl-4-(trifluoromethyl)-1H-pyrazolo[3,4-b]pyridine in 200 ml of anhydrous DMF, under an inert atmosphere of nitrogen, are added 2.18 ml (35 mmol) of methyl iodide and 4.8 g (35.08 mmol) of potassium carbonate, at room temperature. The reaction medium is stirred for 2 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 7.03 g of a colourless oil are obtained.
MH+: 356

2-amino-5-(4,4,5,5-tetramethyl-1,3,2-dioxaborolan-2-yl)benzonitrile

To 3 g (19.7 mmol) of 2-amino-5-chlorobenzonitrile in 95 ml of dioxane under an inert atmosphere of argon are added 6 g (23.6 mmol) of 4,4,4',4',5,5,5',5'-octamethyl-2,2'-bi-1,3,2-dioxaborolane, 2.4 g (29.5 mmol) of sodium acetate, 540 mg (0.59 mmol) of tris(dibenzylideneacetone)dipalladium and 386 mg (1.38 mmol) of tricyclohexylphosphine. The reaction medium is heated at 90° C. for 30 hours and is then hydrolysed with water and extracted with ethyl acetate. The organic phase is dried over sodium sulfate and then concentrated under reduced pressure. The residue obtained is taken up in petroleum ether. The precipitate obtained is filtered off and then dried under reduced pressure at 50° C. for 18 hours. 2.81 g of a white solid are obtained.
MH+: 245

2-amino-5-[1-methyl-3-phenyl-4-(trifluoromethyl)-1H-pyrazolo[3,4-b]pyridin-6-yl]benzonitrile To 250 mg (0.7 mmol) of 6-bromo-1-methyl-3-phenyl-4-(trifluoromethyl)-1H-pyrazolo[3,4-b]pyridine in 4 ml of DMF under an inert atmosphere of argon are added 0.205 g (0.84 mmol) of 2-amino-5-(4,4,5,5-tetramethyl-1,3,2-dioxaborolan-2-yl)benzonitrile, 0.556 g (2.11 mmol) of potassium phosphate dihydrate and 16 mg (0.01 mmol) of tetrakis(triphenylphosphine)palladium. The reaction medium is heated at 150° C. for 15 minutes by microwave. The reaction medium is hydrolysed with water and then extracted with ethyl acetate. The organic phase is dried over sodium sulfate and then concentrated under reduced pressure. The residue obtained is purified by column chromatography on silica gel, eluting with a heptane/dichloromethane mixture. 170 mg of a white solid are obtained.
MH+: 394
Melting point: 269° C.
$^1$H NMR (400 MHz, DMSO-d$_6$): □□□8.50 (d, J=2.2 Hz, 1H) 8.36 (dd, J=8.9, 2.2 Hz, 1H) 8.10 (s, 1H) 7.45-7.53 (m, 5H) 6.96 (d, J=8.9 Hz, 1H) 6.65 (s, 2H) 4.20 (s, 3H)

Example 7: (Compound 108)

2-Amino-5-[2-methyl-3-phenyl-4-(trifluoromethyl)-2H-pyrazolo[3,4-b]pyridin-6-yl]benzonitrile 6-bromo-2-methyl-3-phenyl-4-(trifluoromethyl)-2H-pyrazolo[3,4-b]pyridine To 10 g (29 mmol) of 6-bromo-3-phenyl-4-(trifluoromethyl)-1H-pyrazolo[3,4-b]pyridine in 200 ml of anhydrous DMF, under an inert atmosphere of nitrogen, are added 2.18 ml (35 mmol) of methyl iodide and 4.8 g (35.08 mmol) of potassium carbonate, at room temperature. The reaction medium is stirred for 2 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 2.11 g of a colourless oil are obtained.
MH+: 356

2-amino-5-[2-methyl-3-phenyl-4-(trifluoromethyl)-2H-pyrazolo[3,4-b]pyridin-6-yl]benzonitrile To 200 mg (0.56 mmol) of 6-bromo-2-methyl-3-phenyl-4-(trifluoromethyl)-2H-pyrazolo[3,4-b]pyridine in 3 ml of a 1/1 DME/H$_2$O mixture under an inert atmosphere of argon are added 0.164 g (0.67 mmol) of 2-amino-5-(4,4,5,5-tetramethyl-1,3,2-dioxaborolan-2-yl)benzonitrile, 0.418 g (1.68 mmol) of potassium phosphate dihydrate and 13 mg (0.01 mmol) of tetrakis(triphenylphosphine)palladium. The reaction medium is heated at 150° C. for 15 minutes by microwave. The reaction medium is hydrolysed with water and then extracted with ethyl acetate. The organic phase is dried over sodium sulfate and then stirred for 2 hours in the presence of mercaptopropyl silica gel. After filtration, the organic phase is concentrated under reduced pressure. The residue obtained is taken up in methanol. The precipitate obtained is filtered off and then dried under reduced pressure at 50° C. for 18 hours. 196 mg of a yellow solid are obtained.

MH+: 394

Melting point: 295° C.

$^1$H NMR (400 MHz, DMSO-d$_6$): ▢▢▢▢▢8.39 (d, J=2.2 Hz, 1H) 8.29 (dd, J=8.9, 2.2 Hz, 1H) 8.01 (s, 1H) 7.46-7.65 (m, 5H) 6.94 (d, J=8.9 Hz, 1H) 6.59 (s, 2H) 3.92 (s, 3H)

Example 8: (Compound 88)

2-Amino-5-[1-methyl-4-(trifluoromethyl)-1H-pyrazolo[3,4-b]pyridin-6-yl]benzonitrile 6-chloro-4-(trifluoromethyl)-1H-pyrazolo[3,4-b]pyridine 5 g (24.6 mmol) of 4-(trifluoromethyl)-1H-pyrazolo[3,4-b]pyridin-6-ol are dissolved in 50 ml of POCl$_3$ under an inert atmosphere of nitrogen. The reaction medium is heated at 80° C. for 5 hours and then concentrated under reduced pressure. The residue is taken up in ethyl acetate and then hydrolysed with saturated aqueous sodium hydrogen carbonate solution. The reaction medium is extracted with ethyl acetate. The organic phase is washed with water, dried over sodium sulfate and then concentrated under reduced pressure. 5 g of a beige-coloured solid are obtained.

MH+: 222

Melting point: 112° C.

6-chloro-1-methyl-4-(trifluoromethyl)-1H-pyrazolo[3,4-b]pyridine

To 2 g (9 mmol) of 6-chloro-4-(trifluoromethyl)-1H-pyrazolo[3,4-b]pyridine in 30 ml of anhydrous DMF, under an inert atmosphere of nitrogen, are added 0.67 ml (10.8 mmol) of methyl iodide and 3.5 g (10.83 mmol) of caesium carbonate, at room temperature. The reaction medium is stirred for 20 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 1.42 g of a white solid are obtained.

MH+: 236

Melting point: 123° C.

2-amino-5-[1-methyl-4-(trifluoromethyl)-1H-pyrazolo[3,4-b]pyridin-6-yl]benzonitrile To 200 mg (0.85 mmol) of 6-chloro-1-methyl-4-(trifluoromethyl)-1H-pyrazolo[3,4-b]pyridine in 3 ml of a 1/1 DME/H$_2$O mixture under an inert atmosphere of argon are added 0.248 g (1.02 mmol) of 2-amino-5-(4,4,5,5-tetramethyl-1,3,2-dioxaborolan-2-yl)benzonitrile, 0.632 g (2.55 mmol) of potassium phosphate dihydrate and 19.6 mg (0.02 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is taken up in THF. The solution obtained is stirred for 2 hours in the presence of mercaptopropyl silica gel (Sigma-Aldrich). After filtration, the medium is concentrated under reduced pressure. The residue obtained is taken up in methanol. The precipitate obtained is filtered off and then dried under reduced pressure at 50° C. for 18 hours. 216 mg of a yellow solid are obtained.

MH+: 318

Melting point: 276° C.

$^1$H NMR (400 MHz, DMSO-d$_6$) ▢▢▢▢▢▢8.49 (d, J=2.2 Hz, 1H) 8.34 (dd, J=8.9, 2.2 Hz, 1H) 8.21-8.23 (m, 1H) 8.14 (s, 1H) 6.94 (d, J=9.0 Hz, 1H) 6.64 (s, 2H) 4.16 (s, 3H)

Example 9: (Compound 114)

2-Amino-5-[2-methyl-4-(trifluoromethyl)-2H-pyrazolo[3,4-b]pyridin-6-yl]benzonitrile 6-chloro-2-methyl-4-trifluoromethyl)-2H-pyrazolo[3,4-b]pyridine To 2 g (9 mmol) of 6-chloro-4-(trifluoromethyl)-1H-pyrazolo[3,4-b]pyridine in 30 ml of anhydrous DMF, under an inert atmosphere of nitrogen, are added 0.67 ml (10.8 mmol) of methyl iodide and 3.5 g (10.83 mmol) of caesium carbonate, at room temperature. The reaction medium is stirred for 20 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 0.425 g of a yellow solid is obtained.

MH+: 236

Melting point: 124° C.

2-amino-5-[2-methyl-4-(trifluoromethyl)-2H-pyrazolo[3,4-b]pyridin-6-yl]benzonitrile To 425 mg (1.8 mmol) of 6-chloro-2-methyl-4-(trifluoromethyl)-2H-pyrazolo[3,4-b]pyridine in 10 ml of a 1/1 DME/H$_2$O mixture under an inert atmosphere of argon are added 0.528 g (2.16 mmol) of 2-amino-5-(4,4,5,5-tetramethyl-1,3,2-dioxaborolan-2-yl)benzonitrile, 1.34 g (5.41 mmol) of potassium phosphate dihydrate and 42 mg (0.04 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is purified by column chromatography on silica gel, eluting with a heptane/dichloromethane mixture. The solid obtained is taken up in a dichloromethane/pentane mixture. The precipitate obtained is filtered off and then dried under reduced pressure at 50° C. for 18 hours. 267 mg of a yellow solid are obtained.

MH+: 318

Melting point: 249° C.

$^1$H NMR (400 MHz, DMSO-d$_6$) ▢▢▢▢▢8.62 (s, 1H) 8.39 (d, J=2.2 Hz, 1H) 8.27 (dd, J=8.9, 2.2 Hz, 1H) 8.08 (s, 1H) 6.93 (d, J=8.9 Hz, 1H) 6.58 (s, 2H) 4.24 (s, 3H)

Example 10: (Compound 72)

2-Amino-5-[4-(difluoromethyl)-1-methyl-1H-pyrazolo[3,4-b]pyridin-6-yl]benzonitrile 6-chloro-4-(difluoromethyl)-1H-pyrazolo[3,4-b]pyridine To 5 g (60.2 mmol) of 3-aminopyrazole in an acetic acid/H$_2$O mixture are added 10 g (60.2 mmol) of ethyl 4,4-difluoro-3-oxobutanoate. The reaction medium is heated at 85° C. for 8 hours. After cooling to room temperature, the precipitate obtained is filtered off, washed with water and then dried under reduced pressure. 7.2 g of a solid are obtained, and are taken up in 28.7 g (187.1 mmol) of $POCl_3$. The reaction medium is heated at 85° C. for 4 hours and then concentrated under reduced pressure. After purification by chromatography on silica gel, eluting with an ethyl acetate/cyclohexane mixture, 2.56 g of a white solid are obtained.

$MH^+$: 204

6-chloro-4-(difluoromethyl)-1-methyl-1H-pyrazolo[3,4-b]pyridine

To 1 g (4.91 mmol) of 6-chloro-4-(difluoromethyl)-1H-pyrazolo[3,4-b]pyridine in 20 ml of anhydrous DMF, under an inert atmosphere of nitrogen, are added 0.37 ml (5.89 mmol) of methyl iodide and 0.814 g (5.89 mmol) of potassium carbonate, at room temperature. The reaction medium is stirred for 20 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 0.715 g of a white solid are obtained.

$MH^+$: 218

Melting point: 105° C.

2-amino-5-[4-(difluoromethyl)-1-methyl-1H-pyrazolo[3,4-b]pyridin-6-yl]benzonitrile To 200 mg (0.92 mmol) of 6-chloro-4-(difluoromethyl)-1-methyl-1H-pyrazolo[3,4-b]pyridine in 4 ml of a 1/1 DME/$H_2O$ mixture under an inert atmosphere of argon are added 0.269 g (1.10 mmol) of 2-amino-5-(4,4,5,5-tetramethyl-1,3,2-dioxaborolan-2-yl)benzonitrile, 0684 g (2.76 mmol) of potassium phosphate dihydrate and 21 mg (0.02 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is taken up in THF. The solution obtained is stirred for 2 hours in the presence of mercaptopropyl silica gel (Sigma-Aldrich). After filtration, the medium is concentrated under reduced pressure. The residue obtained is taken up in methanol. The precipitate obtained is filtered off and then dried under reduced pressure at 50° C. for 18 hours. 134 mg of a beige-coloured solid are obtained.

$MH^+$: 300

Melting point: 251° C.

$^1H$ NMR (400 MHz, DMSO-$d_6$): □□□8.36 (d, J=2.2 Hz, 1H), 8.28 (dd, J=8.9, 2.2 Hz, 1H), 8.16 (t, J=1.1 Hz, 1H), 7.97 (t, J=1.3 Hz, 1H), 7.38 (t, J=54.6 Hz, 1H), 6.94 (d, J=8.9 Hz, 1H), 6.60 (s, 2H), 4.13 (s, 3H)

Example 11: (Compound 106)

2-Amino-5-[4-(difluoromethyl)-2-methyl-2H-pyrazolo[3,4-b]pyridin-6-yl]benzonitrile 6-chloro-4-(difluoromethyl)-2-methyl-2H-pyrazolo[3,4-b]pyridine To 1 g (4.91 mmol) of 6-chloro-4-(difluoromethyl)-1H-pyrazolo[3,4-b]pyridine in 20 ml of anhydrous DMF, under an inert atmosphere of nitrogen, are added 0.37 ml (5.89 mmol) of methyl iodide and 0.814 g (5.89 mmol) of potassium carbonate, at room temperature. The reaction medium is stirred for 20 hours and then hydrolysed with water. The aqueous phase is extracted with ethyl acetate. The organic phase obtained is washed with water, dried over sodium sulfate and then concentrated under reduced pressure. The colourless oil obtained is purified by column chromatography on silica gel, eluting with a heptane/dichloromethane mixture. 0.145 g of a white solid are obtained.

$MH^+$: 218

Melting point: 152° C.

2-amino-5-[4-(difluoromethyl)-2-methyl-2H-pyrazolo[3,4-b]pyridin-6-yl]benzonitrile To 145 mg (0.67 mmol) of 6-chloro-4-(difluoromethyl)-2-methyl-2H-pyrazolo[3,4-b]pyridine in 3 ml of a 1/1 DME/$H_2O$ mixture under an inert atmosphere of argon are added 0.195 g (0.8 mmol) of 2-amino-5-(4,4,5,5-tetramethyl-1,3,2-dioxaborolan-2-yl)benzonitrile, 0.469 g (2 mmol) of potassium phosphate dihydrate and 15 mg (0.01 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is taken up in THF. The solution obtained is stirred for 2 hours in the presence of mercaptopropyl silica gel. After filtration, the medium is concentrated under reduced pressure. The residue obtained is taken up in dichloromethane. The precipitate obtained is filtered off and then dried under reduced pressure at 50° C. for 18 hours. The solid obtained is purified by column chromatography on silica gel, eluting with a toluene/acetone mixture. 0.015 g of a yellow solid is obtained.

$MH^+$: 300

$^1H$ NMR (400 MHz, DMSO-$d_6$) □□□□ 8.51 (s, 1H), 8.26 (d, J=2.2 Hz, 1H), 8.22 (dd, J=8.9, 2.2 Hz, 1H), 7.91 (s, 1H), 7.28 (t, J=54.9 Hz, 1H), 6.93 (d, J=8.9 Hz, 1H), 6.55 (s, 2H), 4.22 (s, 3H)

Example 12: (Compound 75)

2-Amino-5-[4-(difluoromethyl)-1H-pyrazolo[3,4-b]pyridin-6-yl]benzonitrile 6-chloro-4-(difluoromethyl)-1-(tetrahydro-2H-pyran-2-yl)-1H-pyrazolo[3,4-b]pyridine To 10 g (49.12 mmol) of 6-chloro-4-(difluoromethyl)-1H-pyrazolo[3,4-b]pyridine in 200 ml of anhydrous dichloromethane, under an inert atmosphere of nitrogen, are added 5.38 ml (58.95 mmol) of 3,4-dihydro-2H-pyran and 0.934 g (4.91 mmol) of PTSA, at 0° C. The reaction medium is stirred for 3 hours at room temperature and then hydrolysed with water. The aqueous phase is extracted with dichloromethane. The organic phase obtained is washed with water, dried over sodium sulfate and then concentrated under reduced pressure. The residue obtained is taken up in a dichloromethane/pentane mixture. The precipitate obtained is filtered off, rinsed with pentane and then dried under reduced pressure at 50° C. for 18 hours. 3.3 g of a beige-coloured powder are obtained after recrystallization from dichloromethane.

$MH^+$: 288

Melting point: 93° C.

2-amino-5-[4-(difluoromethyl)-1-(tetrahydro-2H-pyran-2-yl)-1H-pyrazolo[3,4-b]pyridin-6-yl]benzonitrile To 700 mg (2.43 mmol) of 6-chloro-4-(difluoromethyl)-1(tetrahydro-2H-pyran-2-yl)-1H-pyrazolo[3,4-b]pyridine in 12 ml of a 1/1 DME/H$_2$O mixture under an inert atmosphere of argon are added 0.831 g (3.41 mmol) of 2-amino-5-(4,4,5,5-tetramethyl-1,3,2-dioxaborolan-2-yl)benzonitrile, 1.81 g (7.30 mmol) of potassium phosphate dihydrate and 53 mg (0.05 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is purified by column chromatography on silica gel, eluting with a toluene/acetone mixture. The residue obtained is taken up in a dichloromethane/heptane mixture. The precipitate obtained is filtered off and then dried under reduced pressure at 50° C. for 18 hours. The solid obtained is purified by column chromatography on silica gel, eluting with a toluene/acetone mixture. 0.6 g of a white solid is obtained.

MH$^+$: 370

Melting point: 192° C.

2-amino-5-[4-(difluoromethyl)-1H-pyrazolo[3,4-b]pyridin-6-yl]benzonitrile

To 339 mg (0.92 mmol) of 2-amino-5-[4-(difluoromethyl)-1-(tetrahydro-2H-pyran-2-yl)-1H-pyrazolo[3,4-b]pyridin-6-yl]benzonitrile in 4 ml of methanol is added 0.34 ml of a 4N solution of hydrogen chloride in dioxane at room temperature, under an inert atmosphere of nitrogen. The reaction medium is stirred for 4 hours and then hydrolysed with saturated aqueous sodium hydrogen carbonate solution. The precipitate obtained is filtered off, rinsed with water and then dried under reduced pressure at 50° C. for 18 hours. 196 mg of a yellow powder are obtained.

MH$^+$: 286

Melting point: 263° C.

$^1$H NMR (400 MHz, DMSO-d$_6$) □□□□ 13.90 (br. s., 1H), 8.27 (d, J=2.2 Hz, 1H), 8.16-8.22 (m, 2H), 7.94 (s, 1H), 7.37 (t, J=54.7 Hz, 1H), 6.93 (d, J=9.0 Hz, 1H), 6.58 (s, 2H)

Example 13: (Compound 83)

2-Amino-5-{4-difluoromethyl)-1-[2-(dimethylamino)ethyl]-1H-pyrazolo[3,4-b]pyridin-6-yl}benzonitrile

6-chloro-4-difluoromethyl)-3-iodo-1H-pyrazolo[3,4-b]pyridine

To 10 g (49.12 mmol) of 6-chloro-4-(difluoromethyl)-1H-pyrazolo[3,4-b]pyridine in 200 ml of dichloroethane are added 12.1 g (54.03 mmol) of N-iodosuccinimide at room temperature under an inert atmosphere of nitrogen. The reaction medium is refluxed for 9 hours and then hydrolysed with saturated aqueous sodium hydrogen carbonate solution. The reaction medium is extracted with dichloromethane. The organic phase is washed with water, dried over sodium sulfate and then concentrated under reduced pressure. The solid obtained is taken up in a minimum amount of dichloromethane, filtered off and then dried under reduced pressure at 50° C. for 18 hours.

12.63 g of a beige-coloured solid are obtained.

MH$^+$: 330

Melting point: 175° C.

2-[6-chloro-4-(difluoromethyl)-3-iodo-1H-pyrazolo[3,4-b]pyridin-1-yl]-N,N-dimethylethanamine To 2 g (6.07 mmol) of 6-chloro-4-(difluoromethyl)-3-iodo-1H-pyrazolo[3,4-b]pyridine in 30 ml of anhydrous DMF, under an inert atmosphere of nitrogen, are added 1 g (7.28 mmol) of 2-chloro-N,N-dimethylethanamine hydrochloride and 4.74 g (14.57 mmol) of caesium carbonate, at room temperature. The reaction medium is stirred for 6 hours, followed by addition of 0.5 g of 2-chloro-N,N-dimethylethanamine hydrochloride and 2.4 g of caesium carbonate. The reaction medium is stirred for 18 hours at room temperature and then hydrolysed with water. The aqueous phase is extracted with ethyl acetate. The organic phase obtained is washed with water, dried over sodium sulfate and then concentrated under reduced pressure. The brown oil obtained is purified by column chromatography on silica gel, eluting with a dichloromethane/methanol mixture. 1.51 g of a beige-coloured solid are obtained.

MH$^+$: 401

2-[6-chloro-4-(difluoromethyl)-3-phenyl-1H-pyrazolo[3,4-b]pyridin-1-yl]-N,N-dimethylethanamine To 200 mg (0.5 mmol) of 2-[6-chloro-4-(difluoromethyl)-3-iodo-1H-pyrazolo[3,4-b]pyridin-1-yl]-N,N-dimethylethanamine in 3 ml of a 1/1 DME/H$_2$O mixture under an inert atmosphere of argon are added 0.06 g (0.5 mmol) of phenylboronic acid, 0.371 g (1.5 mmol) of potassium phosphate dihydrate and 11 mg (0.01 mmol) of tetrakis(triphenylphosphine)palladium. The reaction medium is heated at 90° C. in a sealed tube for 24 hours. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. 0.07 g of a yellow oil is obtained.

MH$^+$: 351

2-amino-5-{4-(difluoromethyl)-1-[2-(dimethylamino)ethyl]-1H-pyrazolo[3,4-b]pyridin-6-yl}benzonitrile To 213 mg (0.61 mmol) of 2-[6-chloro-4-(difluoromethyl)-3-phenyl-1H-pyrazolo[3,4-b]pyridin-1-yl]-N,N-dimethylethanamine in 3 ml of a 1/1 DME/H$_2$O mixture under an inert atmosphere of argon are added 0.178 g (0.73 mmol) of 2-amino-5-(4,4,5,5-tetramethyl-1,3,2-dioxaborolan-2-yl)benzonitrile, 0.452 g (1.82 mmol) of potassium phosphate dihydrate and 14 mg (0.01 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. The residue obtained is taken up in a dichloromethane/pentane mixture. The precipitate obtained is filtered off and then dried under reduced pressure at 50° C. for 18 hours. 0.161 g of a white solid is obtained.

MH+: 433

Melting point: 163° C.

¹H NMR (400 MHz, DMSO-d₆) ☐☐☐☐ 8.40 (d, J=2.2 Hz, 1H), 8.30 (dd, J=9.0, 2.2 Hz, 1H), 7.96 (s, 1H), 7.65 (dd, J=7.7, 1.7 Hz, 2H), 7.46-7.55 (m, 3H), 7.28 (t, J=54.6 Hz, 1H), 6.96 (d, J=9.0 Hz, 1H), 6.62 (s, 2H), 4.69 (t, J=6.3 Hz, 2H), 2.85 (t, J=6.3 Hz, 2H), 2.21 (s, 6H)

Example 14: (Compound 93)

1-Methyl-6-[3-(morpholin-4-ylmethyl)phenyl]-3-pyridin-3-yl)-4-(trifluoromethyl)-1H-pyrazolo[3,4-b]pyridine 6-chloro-3-iodo-4-trifluoromethyl-1H-pyrazolo[3,4-b]pyridine To 3 g (13.54 mmol) of 6-chloro-4-(trifluoromethyl)-1H-pyrazolo[3,4-b]pyridine in 50 ml of dichloroethane are added 3.35 g (14.89 mmol) of N-iodosuccinimide at room temperature under an inert atmosphere of nitrogen. The reaction medium is refluxed for 9 hours, followed by addition of 600 mg of N-iodosuccinimide. The reaction medium is refluxed for 9 hours and then hydrolysed with saturated aqueous sodium hydrogen carbonate solution. The reaction medium is extracted with dichloromethane. The organic phase is washed with water, dried over sodium sulfate and then concentrated under reduced pressure. The solid obtained is taken up in a minimum amount of dichloromethane, filtered off and then dried under reduced pressure at 50° C. for 18 hours. 3.8 g of a beige-coloured solid are obtained.

MH+: 347

Melting point: 204° C.

6-chloro-3-iodo-1-methyl-4-(trifluoromethyl)-1H-pyrazolo[3,4-b]pyridine

To 3.8 g (10.94 mmol) of 6-chloro-3-iodo-4-(trifluoromethyl)-1H-pyrazolo[3,4-b]pyridine in 40 ml of anhydrous DMF, under an inert atmosphere of nitrogen, are added 0.82 ml (13.12 mmol) of methyl iodide and 4.27 g (13.12 mmol) of caesium carbonate, at room temperature. The reaction medium is stirred for 6 hours and then hydrolysed with water. The aqueous phase is extracted with ethyl acetate. The organic phase obtained is washed with water, dried over sodium sulfate and then concentrated under reduced pressure. The solid obtained is purified by column chromatography on silica gel, eluting with a heptane/dichloromethane mixture. 2.94 g of a beige-coloured solid are obtained.

MH+: 362

6-chloro-1-methyl-3-(pyridin-3-yl)-4-(trifluoromethyl)-1H-pyrazolo[3,4-b]pyridine To 1.2 g (3.32 mmol) of 6-chloro-3-iodo-1-methyl-4-(trifluoromethyl)-1H-pyrazolo[3,4-b]pyridine in 16 ml of a 1/1 DME/H₂O mixture under an inert atmosphere of argon are added 0.490 g (3.98 mmol) of 3-pyridylboronic acid, 2.47 g (9.96 mmol) of potassium phosphate dihydrate and 77 mg (0.07 mmol) of tetrakis(triphenylphosphine)palladium. The reaction medium is heated at 90° C. in a sealed tube for 24 hours. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. The residue obtained is taken up in a dichloromethane/pentane mixture. The precipitate obtained is filtered off and then dried under reduced pressure at 50° C. for 18 hours. 0.298 g of a brown solid is obtained.

MH+: 313

Melting point: 147° C.

1-methyl-6-[3-(morpholin-4-ylmethyl)phenyl]-3-(pyridin-3-yl)-4-(trifluoromethyl)-1H-pyrazolo[3,4-b]pyridine To 149 mg (0.48 mmol) of 6-chloro-1-methyl-3-(3-pyridyl)-4-(trifluoromethyl)-1H-pyrazolo[3,4-b]pyridine in 4.8 ml of a 1/1 DME/H₂O mixture under an inert atmosphere of argon are added 0.173 g (0.57 mmol) of 4-[3-(4,4,5,5-tetramethyl-1,3,2-dioxaborolan-2-yl)benzyl]morpholine, 0.355 g (1.43 mmol) of potassium phosphate dihydrate and 11 mg (0.01 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. After recrystallization from diisopropyl ether, 0.106 g of a white solid is obtained.

MH+: 454

Melting point: 155° C.

¹H NMR (400 MHz, DMSO-d₆) ☐☐☐☐ 8.68-8.74 (m, 2H), 8.22-8.29 (m, 2H), 8.19 (s, 1H), 7.96 (dt, J=7.9 Hz, 1.7 Hz, 1H), 7.50-7.61 (m, 3H), 4.28 (s, 3H), 3.55-3.69 (m, 6H), 2.43 (m, 4H)

Example 15: (Compound 91)

2-Amino-5-[4-(difluoromethyl)-3-(pyridin-3-yl)-1H-pyrazolo[3,4-b]pyridin-6-yl]benzonitrile 6-chloro-4-(difluoromethyl)-3-iodo-1-(tetrahydro-2H-pyran-2-yl)-1H-pyrazolo[3,4-b]pyridine To 11.3 g (34.45 mmol) of 6-chloro-4-(difluoromethyl)-3-iodo-1H-pyrazolo[3,4-b]pyridine in 150 ml of anhydrous dichloromethane, under an inert atmosphere of nitrogen, are added 3.77 ml (41.34 mmol) of dihydropyran and 0.655 g (3.44 mmol) of PTSA, at 0° C. The reaction medium is stirred for 3 hours at room temperature and then hydrolysed with water. The aqueous phase is extracted with dichloromethane. The organic phase obtained is washed with water, dried over sodium sulfate and then concentrated under reduced pressure. The residue obtained is taken up in a dichloromethane/pentane mixture. The precipitate obtained is filtered off, rinsed with pentane and then dried under reduced pressure at 50° C. for 18 hours. 11.93 g of a beige-coloured powder are obtained.

MH+: 413

Melting point: 157° C.

6-chloro-4-(difluoromethyl)-3-(pyridin-3-yl)-1-(tetrahydro-2H-pyran-2-yl)-1H-pyrazolo[3,4-b]pyridine To 0.8 g (1.93 mmol) of 6-chloro-4-(difluoromethyl)-3-iodo-1-(tetrahydro-2H-pyran-2-yl)-1H-pyrazolo[3,4-b]pyridine in 10 ml of a 1/1 DME/H₂O mixture under an inert atmosphere of argon are added 0.237 g (1.93 mmol) of 3-pyridylboronic acid, 1.44 g (9.96 mmol) of potassium phosphate dihydrate and 45 mg (0.04 mmol) of tetrakis (triphenylphosphine)palladium. The reaction medium is heated at 90° C. in a sealed tube for 24 hours. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. The residue obtained is taken up in a dichloromethane/pentane mixture. The precipitate obtained is filtered off and then dried under reduced pressure at 50° C. for 18 hours. 0.517 g of a yellow solid is obtained.

MH$^+$: 365

2-amino-5-[4-(difluoromethyl)-3-(pyridin-3-yl)-1-(tetrahydro-2H-pyran-2-yl)-1H-pyrazolo[3,4-b]pyridin-6-yl]benzonitrile To 200 mg (0.55 mmol) of 6-chloro-4-(difluoromethyl)-3-(pyridin-3-yl)-1-(tetrahydro-2H-pyran-2-yl)-1H-pyrazolo[3,4-b]pyridine in 4 ml of a 1/1 DME/H$_2$O mixture under an inert atmosphere of argon are added 0.160 g (0.66 mmol) of 2-amino-5-(4,4,5,5-tetramethyl-1,3,2-dioxaborolan-2-yl) benzonitrile, 0.408 g (1.64 mmol) of potassium phosphate dihydrate and 13 mg (0.01 mmol) of tetrakis(triphenylphosphine)palladium. The reaction medium is heated at 150° C. for 15 minutes by microwave. The reaction medium is hydrolysed with water and then extracted with dichloromethane. The organic phase is dried over sodium sulfate and then concentrated under reduced pressure. The residue obtained is purified by column chromatography on silica gel, eluting with a dichloromethane/methanol mixture. The residue obtained is taken up in a dichloromethane/pentane mixture. The precipitate obtained is filtered off and then dried under reduced pressure at 50° C. for 18 hours. 0.204 g of a yellow solid is obtained.

MH$^+$: 447

Melting point: 140° C.

2-amino-5-[4-(difluoromethyl)-3-(pyridin-3-yl)-1H-pyrazolo[3,4-b]pyridin-6-yl]benzonitrile To 204 mg (0.46 mmol) of 2-amino-5-[4-(difluoromethyl)-3-(pyridin-3-yl)-1-(tetrahydro-2H-pyran-2-yl)-1H-pyrazolo[3,4-b]pyridin-6-yl]benzonitrile in 5 ml of an 8/2 dioxane/acetone mixture is added 0.57 ml of a 4N solution of hydrogen chloride in dioxane at room temperature, under an inert atmosphere of nitrogen. The reaction medium is stirred for 24 hours, followed by addition of methanol and 0.6 ml of a 4N solution of hydrogen chloride in dioxane. The reaction medium is stirred for 24 hours and then hydrolysed with saturated aqueous sodium hydrogen carbonate solution. The precipitate obtained is filtered off, rinsed with water and then dried under reduced pressure at 50° C. for 18 hours. 131 mg of a yellow powder are obtained.

MH$^+$: 363

Melting point: 296° C.

$^1$H NMR (400 MHz, DMSO-d$_6$): ☐ 14.26 (br. s., 1H), 8.82 (d, J=1.6 Hz, 1H), 8.68 (dd, J=4.8, 1.6 Hz, 1H), 8.33 (d, J=2.1 Hz, 1H), 8.24 (dd, J=8.9, 2.1 Hz, 1H), 8.05 (dt, J=7.9, 1.8 Hz, 1H), 7.98 (s, 1H), 7.54 (dd, J=7.9, 4.8 Hz, 1H), 7.28 (t, J=54.7 Hz, 1H), 6.95 (d, J=8.9 Hz, 1H), 6.62 (s, 2H)

The table that follows illustrates the chemical structures and physical properties of a number of examples of compounds according to the invention. In this table:

Me and Et represent, respectively, methyl and ethyl groups;
Ph represents a phenyl group;
"m.p." represents the melting point of the compound, expressed in degrees Celsius;
"M+H$^+$" represents the mass of the compound, obtained by LC-MS (Liquid Chromatography-Mass Spectroscopy). The high-performance liquid chromatography analytical method used is detailed below:

Column: Kromasil, 50×2.1 mm, 3.5 ☐m
Solvent A: H$_2$O/ACN/TFA (1000/30/0.5); solvent B: ACN/TFA (1000/0.5); flow rate=0.5 mL/min
Gradient: 100/0 (0 min) to 0/100 (12 min) to 0/100 (15 min)
Detection: 220 nM
Ionization: ESI+
in the "salt" column, "/" represents a compound in free base form, whereas "HCl" represents a compound in hydrochloride form and TFA represents a compound in the form of the trifluoroacetic acid salt.

TABLE

| No. | R$_2$ | R$_3$ | R$_1$ | R$_4$ | Salt | m.p. (° C.) | M + H$^+$ |
|---|---|---|---|---|---|---|---|
| | | | | | | | (I') |
| | | | 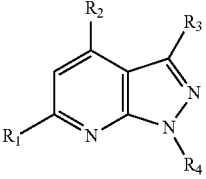 | | | | |
| 1 | CF$_3$ | Ph | 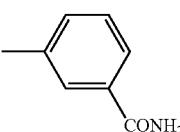 | Me | / | / | 397 |
| 2 | CF$_3$ | Ph | 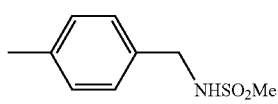 | Me | / | / | 461 |

TABLE-continued
| No. | R₂ | R₃ | R₁ | R₄ | Salt | m.p. (° C.) | M + H⁺ |
|---|---|---|---|---|---|---|---|
| 3 | CF₃ | Ph | 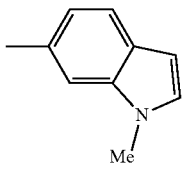 | Me | / | / | 407 |
| 4 | CF₃ | Ph | 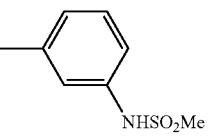 | Me | / | / | 447 |
| 5 | CF₃ | Ph | 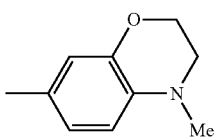 | Me | / | / | 426 |
| 6 | CF₃ | Ph | 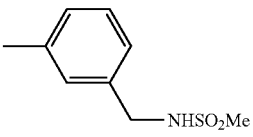 | Me | / | / | 461 |
| 7 | CF₃ | Ph | 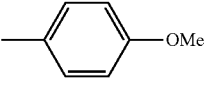 | Me | / | / | 384 |
| 8 | CF₃ | Ph | 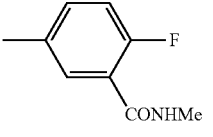 | Me | / | / | 429 |
| 9 | CF₃ | Ph | 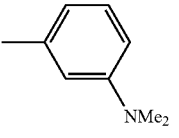 | Me | / | / | 397 |
| 10 | CF₃ | Ph | 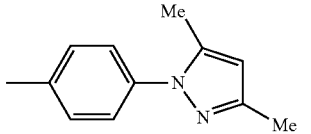 | Me | / | / | 448 |
| 11 | CF₃ | Ph | 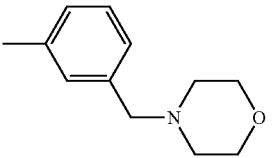 | Me | / | / | 453 |
| 12 | CF₃ | Ph | 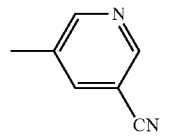 | Me | / | / | 380 |
| 13 | CF₃ | Ph | 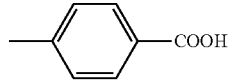 | Me | / | / | 398 |

TABLE-continued

| No. | R₂ | R₃ | R₁ | R₄ | Salt | m.p. (° C.) | M + H⁺ |
|---|---|---|---|---|---|---|---|
| 14 | CF₃ | Ph | 4-CONMe₂-phenyl | Me | / | / | 425 |
| 15 | CF₃ | Ph | 3-CONMe₂-phenyl | Me | / | / | 425 |
| 16 | CF₃ | Ph | 5-(morpholin-4-yl)pyridin-2-yl (linked at 5-position) | Me | / | / | 440 |
| 17 | CF₃ | Ph | 2-methoxypyridin-5-yl | Me | / | / | 385 |
| 18 | CF₃ | Ph | 6-(pyrrolidin-1-yl)pyridin-3-yl | Me | / | / | 424 |
| 19 | CF₃ | Ph | 1,5-dimethyl-3-(trifluoromethyl)-1H-pyrazol-4-yl | Me | / | / | 426 |
| 20 | CF₃ | Ph | benzothiazol-6-yl | Me | / | / | 411 |
| 21 | CF₃ | Ph | 4-CONMe₂-phenyl | H | HCl | / | 411 |
| 22 | CF₃ | Ph | 4-(morpholin-4-yl)phenyl | H | HCl | / | 425 |
| 23 | CF₃ | Ph | 6-(morpholin-4-yl)pyridin-3-yl | H | HCl | / | 426 |
| 24 | CF₃ | Ph | 6-methoxypyridin-3-yl | H | HCl | / | 371 |
| 25 | CF₃ | Ph | 3-(morpholin-4-yl)phenyl | H | HCl | / | 425 |

TABLE-continued

| No. | R₂ | R₃ | R₁ | R₄ | Salt | m.p. (° C.) | M + H⁺ |
|---|---|---|---|---|---|---|---|
| 26 | CF$_3$ | Ph | 3-(CONHMe)phenyl | H | HCl | / | 397 |
| 27 | CF$_3$ | Ph | 3-(NHSO$_2$Me)phenyl | H | HCl | / | 433 |
| 28 | CF$_3$ | Ph | 3-(piperidin-1-yl)phenyl | H | HCl | / | 423 |
| 29 | CF$_3$ | Ph | 2-fluoro-5-(CONHMe)phenyl | H | HCl | / | 415 |
| 30 | CF$_3$ | Ph | 5-cyanopyridin-3-yl | H | HCl | / | 366 |
| 31 | CHF$_2$ | Ph | 4-(pyrrolidin-1-ylcarbonyl)phenyl | H | HCl | 248 | 455 |
| 32 | CHF$_2$ | Ph | 1-methyl-1H-pyrazol-4-yl | H | HCl | / | 362 |
| 33 | CHF$_2$ | Ph | 3,4,5-trimethyl-1H-pyrazol-yl | H | HCl | / | 376 |
| 34 | CHF$_2$ | Ph | 1H-pyrazol-4-yl | H | HCl | / | 348 |
| 35 | CHF$_2$ | Ph | 6-methoxypyridin-3-yl | H | HCl | / | 389 |

TABLE-continued
| No. | R₂ | R₃ | R₁ | R₄ | Salt | m.p. (° C.) | M + H⁺ |
|---|---|---|---|---|---|---|---|
| 36 | CHF₂ | Ph | 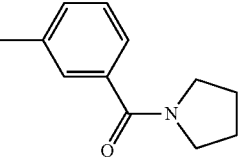 | H | HCl | / | 455 |
| 37 | CHF₂ | Ph | 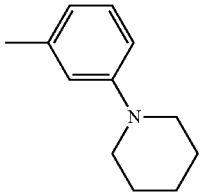 | H | HCl | / | 441 |
| 38 Ex. 2 | COOH | H | 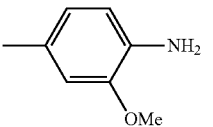 | H | / | / | 285 |
| 39 | CONHMe | Ph | 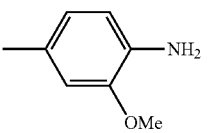 | H | TFA | / | 458 |
| 40 | CONH₂ | Ph | 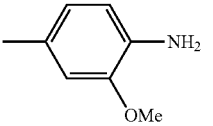 | H | TFA | / | 474 |
| 41 | CONHMe | H | 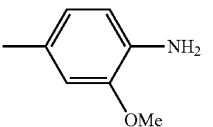 | H | TFA | / | 412 |
| 42 | CONH₂ | H | 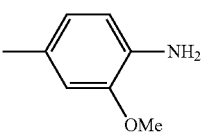 | H | TFA | / | 398 |
| 43 | COOH | Ph | 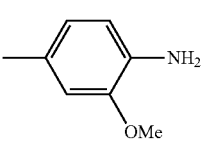 | H | / | / | 361 |
| 44 | COOH | Ph | 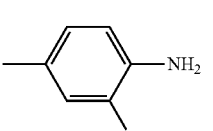 | Me | / | / | 375 |
| 45 | COOH | H | 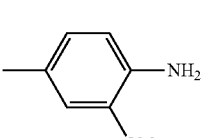 | Me | / | / | 299 |

TABLE-continued

| No. | R$_2$ | R$_3$ | R$_1$ | R$_4$ | Salt | m.p. (° C.) | M + H$^+$ |
|---|---|---|---|---|---|---|---|
| 46 Ex. 1 | CONH$_2$ | Ph | 2-F, 3-COOH phenyl | H | TFA | / | 377 |
| 47 | CONH$_2$ | Ph | 2-NH$_2$, 3-COOH phenyl | H | / | / | 374 |
| 48 | CONH$_2$ | Ph | 2-NH$_2$, 3-CN phenyl | H | TFA | / | 355 |
| 49 | CONH$_2$ | 2-thienyl | 2-NH$_2$, 3-CN phenyl | H | / | / | 361 |
| 50 | COOH | cPr | 2-NH$_2$, 3-CN phenyl | H | / | / | 320 |
| 51 | CONH$_2$ | H | 2-F, 3-COOH phenyl | H | / | / | 301 |
| 52 | CONH$_2$ | Ph | 2-F, 3-CN phenyl | H | / | / | 358 |
| 53 Ex. 3 | CHF$_2$ | Ph | 2-F, 3-COOH phenyl | H | / | / | 384 |
| 54 | CF$_3$ | Ph | 2-F, 3-CN phenyl | H | / | / | 383 |
| 55 | CHF$_2$ | Ph | 2-NH$_2$, 3-CN phenyl | H | HCl | 282 | 362 |
| 56 Ex. 4 | CF$_3$ | Ph | 2-F, 3-COOH phenyl | H | / | / | 402 |

TABLE-continued

| No. | R₂ | R₃ | R₁ | R₄ | Salt | m.p. (°C.) | M + H⁺ |
|---|---|---|---|---|---|---|---|
| 57 Ex. 6 | CF₃ | Ph | 4-methyl-2-amino-3-cyanophenyl (2-NH₂, 3-CN) | Me | / | 269 | 394 |
| 58 | CF₃ | Ph | 5-methyl-2-fluoro-benzoic acid (2-F, COOH) | Me | / | / | 416 |
| 59 | CF₃ | Ph | 5-methyl-1H-indol-yl | H | / | / | 379 |
| 60 | CF₃ | Ph | 5-methyl-benzimidazol-2(3H)-one | H | / | 380 | 396 |
| 61 Ex. 5 | CF₃ | Ph | 4-methyl-N,N-dimethylaminophenyl (NMe₂) | H | / | 227 | 383 |
| 62 | CONHPh | H | 4-methyl-2-amino-3-cyanophenyl | H | HCl | / | 355 |
| 63 | CH₂C(O)NH-(pyridin-2-ylmethyl) | H | 4-methyl-2-amino-3-cyanophenyl | H | HCl | / | 370 |
| 64 | C(O)NH-(pyridin-2-yl) | H | 4-methyl-2-amino-3-cyanophenyl | H | HCl | / | 356 |
| 65 | C(O)NH-(pyridin-3-yl) | H | 4-methyl-2-amino-3-cyanophenyl | H | HCl | / | 356 |
| 66 | C(O)NH-(pyridin-4-yl) | H | 4-methyl-2-amino-3-cyanophenyl | H | HCl | / | 356 |
| 67 | CHF₂ | 4-Py | 5-methyl-2-fluoro-3-cyanophenyl (2-F, CN) | Me | / | / | 380 |

TABLE-continued

| No. | R₂ | R₃ | R₁ | R₄ | Salt | m.p. (° C.) | M + H⁺ |
|---|---|---|---|---|---|---|---|
| 68 | CONHPh | H | 5-methyl-1H-benzimidazol-2-yl | H | HCl | / | 355 |
| 69 | CH₂C(O)NH-(pyridin-2-yl) | H | 5-methyl-1H-benzimidazol-2-yl | H | HCl | / | 356 |
| 70 | CH₂C(O)NH-CH₂-(pyridin-3-yl) | H | 5-methyl-1H-benzimidazol-2-yl | H | HCl | / | 370 |
| 71 | CONHPh | H | 5-methyl-2-oxo-2,3-dihydro-1H-benzimidazol-1-yl | H | / | / | 371 |
| 72 Ex. 10 | CHF₂ | H | 4-methyl-2-amino-3-cyanophenyl | Me | / | 251 | 300 |
| 73 | CHF₂ | H | 3-methyl-5-cyanophenyl | Me | / | 162 | 285 |
| 74 | CHF₂ | H | 4-methyl-2-aminophenyl | Me | / | 149 | 275 |
| 75 Ex. 12 | CHF₂ | H | 4-methyl-2-amino-3-cyanophenyl | H | / | 263 | 286 |
| 76 | CF₃ | Ph | 4-methyl-2-amino-3-cyanophenyl | CH₂CH₂CH₂NMe₂ | / | 183 | 451 |
| 77 | CF₃ | Ph | 5-methyl-2-methoxy-3-cyanopyridin-6-yl | Me | / | 250 | 410 |
| 78 | CHF₂ | Ph | 4-methyl-2-amino-3-cyanophenyl | Me | / | 246 | 376 |

TABLE-continued

| No. | $R_2$ | $R_3$ | $R_1$ | $R_4$ | Salt | m.p. (°C.) | M + H[+] |
|---|---|---|---|---|---|---|---|
| 79 | $CHF_2$ | Ph | 4-aminophenyl | Me | / | 176 | 351 |
| 80 | $CHF_2$ | Ph | 3-(dimethylamino)phenyl | Me | / | 154 | 379 |
| 81 | $CF_3$ | Ph | 2-amino-3-cyanophenyl | N-propylpiperidine | / | 192 | 491 |
| 82 | $CF_3$ | Ph | 3-(dimethylamino)phenyl | N-propylpiperidine | HCl | 227 | 494 |
| 83 Ex. 13 | $CHF_2$ | Ph | 2-amino-3-cyanophenyl | propyl-NMe | / | 163 | 433 |
| 84 | $CF_3$ | H | 3-(dimethylamino)phenyl | N-propylmorpholine | / | 110 | 420 |
| 85 | $CF_3$ | H | 5-cyanopyridin-3-yl | N-propylmorpholine | / | / | 403 |
| 86 | $CF_3$ | H | 5-carbamoylpyridin-3-yl | N-propylmorpholine | / | 238 | 421 |
| 87 | $CF_3$ | H | 3-(morpholinomethyl)phenyl | Me | / | 105 | 377 |
| 88 Ex. 8 | $CF_3$ | H | 2-amino-3-cyanophenyl | Me | / | 276 | 318 |
| 89 | $CF_3$ | Ph | 4-methoxyphenyl | Me | / | 181 | 384 |

TABLE-continued

| No. | R₂ | R₃ | R₁ | R₄ | Salt | m.p. (° C.) | M + H⁺ |
|---|---|---|---|---|---|---|---|
| 90 | CF₃ | H | 3-NMe₂-phenyl | Me | / | 91 | 321 |
| 91 Ex. 15 | CHF₂ | 3-Py | 2-NH₂-5-substituted-benzonitrile | H | / | 296 | 363 |
| 92 | CHF₂ | 4-Py | 2-NH₂-5-substituted-benzonitrile | H | / | 325 | 363 |
| 93 Ex. 14 | CF₃ | 3-Py | 3-(morpholinomethyl)phenyl | Me | / | 155 | 454 |
| 94 | CHF₂ | 3MeO—Ph | 2-NH₂-5-substituted-benzonitrile | Me | / | 233 | 392 |
| 95 | CF₃ | H | 3-(morpholinomethyl)phenyl | Pr | HCl | 271 | 405 |
| 96 | CF₃ | H | 4-OMe-phenyl | Pr | / | 72 | 336 |
| 97 | CF₃ | 3MeO—Ph | 5-CN-pyridin-3-yl | Me | / | 194 | 410 |
| 98 | CF₃ | 3MeO—Ph | 3-(morpholinomethyl)phenyl | Me | / | 114 | 483 |
| 99 | CF₃ | 3MeO—Ph | 3-NMe₂-phenyl | Me | / | 138 | 427 |

TABLE-continued

| No. | R$_2$ | R$_3$ | R$_1$ | R$_4$ | Salt | m.p. (° C.) | M + H$^+$ |
|---|---|---|---|---|---|---|---|
| 100 | CF$_3$ | 3MeO—Ph | 3-MeO-phenyl | Me | / | 133 | 414 |
| 101 | CONH$_2$ | 3-Py | 4-F-3-CN-phenyl | H | / | / | 377 |
| 121 | CHF$_2$ | Ph | 4-NH$_2$-phenyl | H | / | 216 | 337 |
| 122 | CHF$_2$ | Ph | phenyl | H | HCl/ | / | 322 |

(I")

pyrazolo[3,4-b]pyridine core with R$_2$, R$_3$, R$_4$, R$_1$ substituents

| No. | R$_2$ | R$_3$ | R$_1$ | R$_4$ | Salt | m.p. (° C.) | M + H$^+$ |
|---|---|---|---|---|---|---|---|
| 102 | COOH | H | 4-NH$_2$-3-OMe-phenyl | Me | / | / | 299 |
| 103 | CONH$_2$ | H | 4-NH$_2$-3-OMe-phenyl | Me | TFA | / | 412 |
| 104 | COOH | H | 4-NH$_2$-3-CN-phenyl | Me | / | / | 294 |
| 105 | CHF$_2$ | H | 4-F-3-CN-phenyl | Me | / | / | 303 |
| 106 Ex. 11 | CHF$_2$ | H | 4-NH$_2$-3-CN-phenyl | Me | / | / | 300 |
| 107 | CHF$_2$ | H | 4-F-3-CONH$_2$-phenyl | Me | / | / | 321 |

TABLE-continued

| No. | R₂ | R₃ | R₁ | R₄ | Salt | m.p. (° C.) | M + H⁺ |
|---|---|---|---|---|---|---|---|
| 108 Ex. 7 | CF₃ | Ph | 4-methyl-2-amino-benzonitrile | Me | / | 295 | 394 |
| 109 | CF₃ | Ph | 4-methyl-2-amino-benzonitrile | propyl-NMe₂ | / | 237 | 451 |
| 110 | CF₃ | Ph | 4-methyl-2-amino-benzonitrile | propyl-morpholine | / | 249 | 493 |
| 111 | CHF₂ | H | 4-methyl-2-amino-benzonitrile | propyl-NMe₂ | / | 182 | 357 |
| 112 | CHF₂ | H | 4-methyl-2-amino-benzonitrile | propyl-morpholine | / | 242 | 399 |
| 113 | CF₃ | H | 3-methylbenzyl-morpholine | propyl-morpholine | / | 101 | 476 |
| 114 Ex. 9 | CF₃ | H | 4-methyl-2-amino-benzonitrile | Me | / | 249 | 318 |
| 115 | CF₃ | H | 3-methyl-phenyl-NMe₂ | Pr | HCl | 181 | 425 |
| 116 | CHF₂ | H | 4-methyl-2-amino-benzonitrile | propyl-piperidine | / | 230 | 397 |
| 117 | CHF₂ | H | 4-methyl-2-amino-benzonitrile | Pr | / | 214 | 328 |
| 118 | CF₃ | H | 4-methyl-2-amino-benzonitrile | Pr | / | 239 | 346 |

TABLE-continued

| No. | $R_2$ | $R_3$ | $R_1$ | $R_4$ | Salt | m.p. (° C.) | M + H⁺ |
|---|---|---|---|---|---|---|---|
| 119 | $CF_3$ | H | 3-(morpholinomethyl)phenyl | Pr | / | 288 | 405 |
| 120 | $CF_3$ | H | 3-(dimethylamino)phenyl (NMe₂) | Pr | / | 89 | 349 |

The compounds according to the invention underwent pharmacological trials to determine their inhibitory effect on the FGF receptors.

Example 16: In Vitro Angiogenesis of HUVEC Cells Induced with FGF-2

In order to demonstrate the capacity of the FGF-R antagonists of the present invention to inhibit FGF-induced angiogenesis, in vitro angiogenesis experiments were performed with human endothelial cells of HUVEC type, stimulated with FGF-2 or b-FGF.

To do this, matrices composed of matrigel (growth factor reduced matrigel, Becton Dickinson 356230) and of collagen (rat tail collagen type I, Becton Dickinson 354236) are deposited in an amount of 160 μl into each chamberslide well (Biocoat Cellware collagen, Type I, 8-well culturesides: Becton dickinson 354630), or 60 μl per well of 96-plate wells (Biocoat collagenl cellware, Becton Dickinson 354407). The matrix is prepared by mixing ⅓ of matrigel, 1 mg/ml final of collagen, 0.1N NaOH (0.026× the volume of collagen in μl), PBS 1×, and the volume is then adjusted with water. The gels are kept for 1 hour at 37° C. to allow their polymerization. Next, the human venous endothelial cells (HUVEC ref.: C-12200—Promocell) were seeded at $15 \times 10^3$ or $6 \times 10^3$ cells/well in 400 or 120 μl (for the 8-well or 96-well plates, respectively) of EBM medium (Clonetics C3121)+2% FBS+hEGF 10 μg/ml. They are stimulated with 1 or 3 ng/ml of FGF-2 (R&D system, 133-FB-025; Invitrogen, PHG0026) for 24 hours at 37° C. in the presence of 5% $CO_2$. After 24 hours, the length of the network of microtubules formed is measured by means of the computer-assisted image analysis system (Imagenia Biocom, Courtaboeuf, France) and the total length of the pseudotubules in each well is determined. The mean total length of the microcapillary network is calculated in μm for each condition corresponding to the mean on 6 replicates Stimulation with FGF-2 allows induction of the formation of new tubules. An FGF-R antagonist is considered as being active in this test if it is capable of partially inhibiting this angiogenesis at a dose of less than or equal to 300 nM.

Example of Screening of FGF-R Antagonists

In this experiment, the molecules are evaluated from 0.03 nM to 300 nM depending on the molecule with regard to induction of the angiogenesis of human HUVEC cells with FGF-2. Compounds 38 (Example 2), 46 (Example 1), 53 (Example 3), 56 (Example 4), 57 (Example 6), 61 (Example 5), 75 (Example 12), 83 (Example 13), 88 (Example 8), 91 (Example 15), 93 (Example 14), 106 (Example 11), 108 (Example 7) and 114 (Example 9) are active since they have inhibitory activity on the formation of pseudotubules of greater than or equal to 20% at a dose of less than or equal to 300 nM (FIG. 1). In the following table, A=active for a concentration<1 nM, B=active at a concentration of 1 nM, C=active at a concentration of 3 nM, D=active at a concentration of 10 nM, E=active at a concentration of 30 nM, and F=active at a concentration of 300 nM.

| No. | $R_2$ | $R_3$ | $R_1$ | $R_4$ | Salt | Activity |
|---|---|---|---|---|---|---|
| 1 | $CF_3$ | Ph | 3-carbamoylphenyl ($CONH_2$) | Me | / | C |

(I')

-continued

| No. | R₂ | R₃ | R₁ | R₄ | Salt | Activity |
|---|---|---|---|---|---|---|
| 7 | CF₃ | Ph | 4-methoxyphenyl | Me | / | C |
| 8 | CF₃ | Ph | 2-fluoro-4-(N-methylcarbamoyl)phenyl | Me | / | C |
| 9 | CF₃ | Ph | 3-(dimethylamino)phenyl | Me | / | C |
| 11 | CF₃ | Ph | 3-(morpholinomethyl)phenyl | Me | / | C |
| 12 | CF₃ | Ph | 5-cyanopyridin-3-yl | Me | / | C |
| 15 | CF₃ | Ph | 3-(N,N-dimethylcarbamoyl)phenyl | Me | / | C |
| 19 | CF₃ | Ph | 1-methyl-3-(trifluoromethyl)-1H-pyrazol-5-yl | Me | / | C |
| 22 | CF₃ | Ph | 4-morpholinophenyl | H | HCl | D |
| 24 | CF₃ | Ph | 6-methoxypyridin-3-yl | H | HCl | C |
| 26 | CF₃ | Ph | 3-(N-methylcarbamoyl)phenyl | H | HCl | F |
| 29 | CF₃ | Ph | 2-fluoro-4-(N-methylcarbamoyl)phenyl | H | HCl | C |

-continued
| No. | R₂ | R₃ | R₁ | R₄ | Salt | Activity |
|---|---|---|---|---|---|---|
| 30 | CF₃ | Ph | 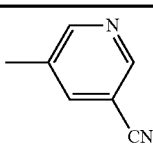 | H | HCl | C |
| 31 | CHF₂ | Ph | 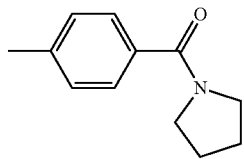 | H | HCl | E |
| 32 | CHF₂ | Ph | 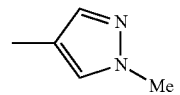 | H | HCl | C |
| 33 | CHF₂ | Ph | 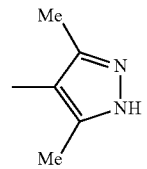 | H | HCl | C |
| 34 | CHF₂ | Ph | 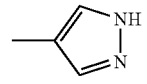 | H | HCl | E |
| 35 | CHF₂ | Ph | 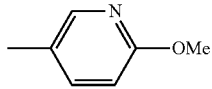 | H | HCl | C |
| 37 | CHF₂ | Ph | 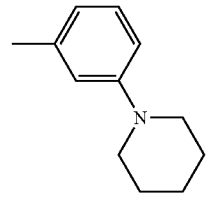 | H | HCl | C |
| 38 Ex. 2 | COOH | H | 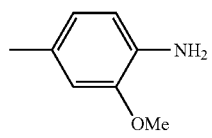 | H | / | C |
| 39 | CONHMe | Ph | 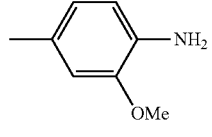 | H | TFA | D |
| 40 | CONH₂ | Ph | 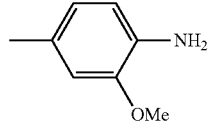 | H | TFA | C |
| 41 | CONHMe | H | 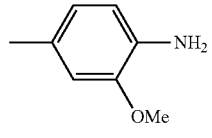 | H | TFA | F |

-continued

| No. | R₂ | R₃ | R₁ | R₄ | Salt | Activity |
|---|---|---|---|---|---|---|
| 42 | CONH₂ | H | 4-methyl-2-amino-3-methoxyphenyl | H | TFA | F |
| 43 | COOH | Ph | 4-methyl-2-amino-3-methoxyphenyl | H | / | F |
| 44 | COOH | Ph | 4-methyl-2-amino-3-methoxyphenyl | Me | / | D |
| 45 | COOH | H | 4-methyl-2-amino-3-methoxyphenyl | Me | / | B |
| 46 Ex. 1 | CONH₂ | Ph | 4-methyl-2-fluoro-3-carboxyphenyl | H | TFA | A |
| 47 | CONH₂ | Ph | 4-methyl-2-amino-3-carboxyphenyl | H | / | E |
| 48 | CONH₂ | Ph | 4-methyl-2-amino-3-cyanophenyl | H | TFA | A |
| 49 | CONH₂ | 2-thienyl | 4-methyl-2-amino-3-cyanophenyl | H | / | B |
| 50 | COOH | cPr | 4-methyl-2-amino-3-cyanophenyl | H | / | A |
| 51 | CONH₂ | H | 4-methyl-2-fluoro-3-carboxyphenyl | H | / | C |
| 52 | CONH₂ | Ph | 4-methyl-2-fluoro-3-cyanophenyl | H | / | B |

-continued

| No. | R$_2$ | R$_3$ | R$_1$ | R$_4$ | Salt | Activity |
|---|---|---|---|---|---|---|
| 53 Ex. 3 | CHF$_2$ | Ph | 5-methyl-2-fluoro-benzoic acid | H | / | A |
| 54 | CF$_3$ | Ph | 5-methyl-2-fluoro-benzonitrile | H | / | A |
| 55 | CHF$_2$ | Ph | 2-amino-5-methyl-benzonitrile | H | HCl | A |
| 56 Ex. 4 | CF$_3$ | Ph | 5-methyl-2-fluoro-benzoic acid | H | / | A |
| 57 Ex. 6 | CF$_3$ | Ph | 2-amino-5-methyl-benzonitrile | Me | / | C |
| 59 | CF$_3$ | Ph | 5-methyl-1H-indole | H | / | B |
| 60 | CF$_3$ | Ph | 5-methyl-1,3-dihydro-benzimidazol-2-one | H | / | A |
| 61 Ex. 5 | CF$_3$ | Ph | 4-methyl-N,N-dimethylaniline | H | / | B |
| 72 Ex. 10 | CHF$_2$ | H | 2-amino-5-methyl-benzonitrile | Me | / | D |
| 73 | CHF$_2$ | H | 3-methyl-benzonitrile | Me | / | A |
| 75 Ex. 12 | CHF$_2$ | H | 2-amino-5-methyl-benzonitrile | H | / | D |

-continued

| No. | $R_2$ | $R_3$ | $R_1$ | $R_4$ | Salt | Activity |
|---|---|---|---|---|---|---|
| 76 | $CF_3$ | Ph | 4-methyl-2-amino-3-cyanophenyl | propyl-$NMe_2$ | / | C |
| 77 | $CF_3$ | Ph | 5-methyl-2-methoxy-3-cyanopyridyl | Me | / | C |
| 78 | $CHF_2$ | Ph | 4-methyl-2-amino-3-cyanophenyl | Me | / | D |
| 79 | $CHF_2$ | Ph | 4-methylaminophenyl | Me | / | C |
| 80 | $CHF_2$ | Ph | 3-methyl-$NMe_2$-phenyl | Me | / | A |
| 81 | $CF_3$ | Ph | 4-methyl-2-amino-3-cyanophenyl | propyl-piperidinyl | / | A |
| 82 | $CF_3$ | Ph | 3-methyl-$NMe_2$-phenyl | propyl-piperidinyl | HCl | D |
| 83 Ex. 13 | $CHF_2$ | Ph | 4-methyl-2-amino-3-cyanophenyl | propyl-$NMe_2$ | / | D |
| 84 | $CF_3$ | H | 3-methyl-$NMe_2$-phenyl | propyl-morpholinyl | / | C |
| 85 | $CF_3$ | H | 5-methyl-3-cyanopyridyl | propyl-morpholinyl | / | C |
| 86 | $CF_3$ | H | 5-methyl-3-$CONH_2$-pyridyl | propyl-morpholinyl | / | C |

-continued
| No. | R₂ | R₃ | R₁ | R₄ | Salt | Activity |
|---|---|---|---|---|---|---|
| 87 | CF₃ | H | 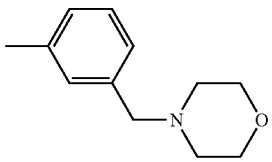 | Me | / | C |
| 88 Ex. 8 | CF₃ | H |  | Me | / | C |
| 89 | CF₃ | Ph | 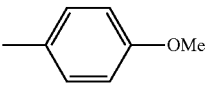 | Me | / | C |
| 90 | CF₃ | H | 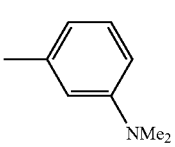 | Me | / | C |
| 91 Ex. 15 | CHF₂ | 3-py | 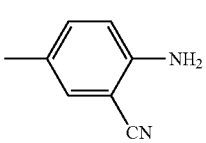 | H | / | F |
| 92 | CHF₂ | 4-py | 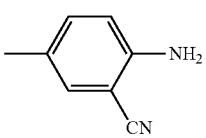 | H | / | F |
| 93 Ex. 14 | CF₃ | 3-py | 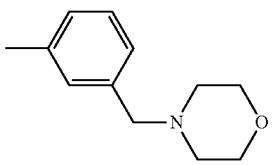 | Me | / | F |
| 94 | CHF₂ | 3MeO—Ph | 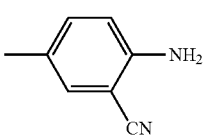 | Me | / | F |
| 95 | CF₃ | H | 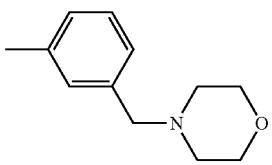 | Pr | HCl | F |
| 96 | CF₃ | H | 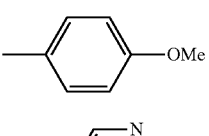 | / |  | F |
| 97 | CF₃ | 3MeO—Ph | 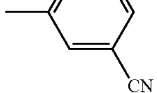 | Me | / | F |

-continued
| No. | R₂ | R₃ | R₁ | R₄ | Salt | Activity |
|---|---|---|---|---|---|---|
| 98 | CF₃ | 3MeO—Ph | 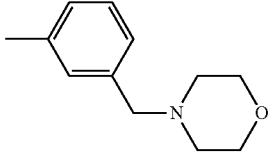 | Me | / | E |
| 99 | CF₃ | 3MeO—Ph | 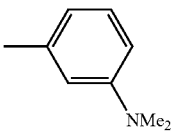 | Me | / | F |
| 100 | CF₃ | 3MeO—Ph | 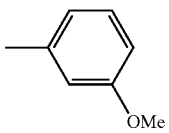 | Me | / | E |
| 101 | CONH₂ | 3-Py | 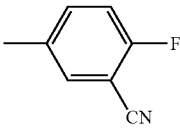 | H | / | B |
| 121 | CHF₂ | Ph | 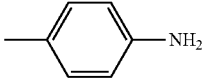 | H | / | |
| 122 | CHF₂ | Ph | 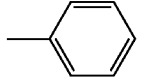 | H | HCl | |
(I″)
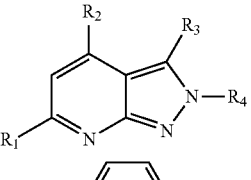
| No. | R₂ | R₃ | R₁ | R₄ | Salt | Activity |
|---|---|---|---|---|---|---|
| 102 | COOH | H | 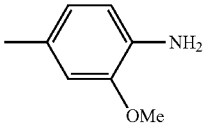 | Me | / | B |
| 103 | CONH₂ | H | 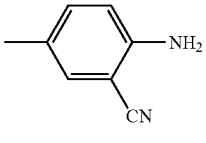 | Me | TFA | D |
| 104 | COOH | H | 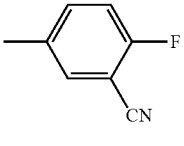 | Me | / | B |
| 105 | CHF₂ | H | | Me | / | B |

-continued

| No. | R₂ | R₃ | R₁ | R₄ | Salt | Activity |
|---|---|---|---|---|---|---|
| 106 Ex 11 | CHF₂ | H | 2-amino-5-methyl-benzonitrile | Me | / | A |
| 108 Ex. 7 | CF₃ | Ph | 2-amino-5-methyl-benzonitrile | Me | / | C |
| 110 | CF₃ | Ph | 2-amino-5-methyl-benzonitrile | propyl-morpholine | / | B |
| 111 | CHF₂ | H | 2-amino-5-methyl-benzonitrile | propyl-NMe₂ | / | D |
| 112 | CHF₂ | H | 2-amino-5-methyl-benzonitrile | propyl-morpholine | / | B |
| 113 | CF₃ | H | 3-(morpholinomethyl)-methylphenyl | propyl-morpholine | / | C |
| 114 Ex. 9 | CF₃ | H | 2-amino-5-methyl-benzonitrile | Me | / | C |
| 115 | CF₃ | H | 3-(dimethylamino)-methylphenyl | Pr | HCl | F |
| 116 | CHF₂ | H | 2-amino-5-methyl-benzonitrile | propyl-piperidine | / | F |
| 117 | CHF₂ | H | 2-amino-5-methyl-benzonitrile | Pr | / | F |
| 118 | CF₃ | H | 2-amino-5-methyl-benzonitrile | Pr | / | F |

-continued

| No. | R₂ | R₃ | R₁ | R₄ | Salt | Activity |
|---|---|---|---|---|---|---|
| 119 | $CF_3$ | H | (phenyl-CH₂-N-morpholine) | Pr | / | F |
| 120 | $CF_3$ | H | (phenyl-$NMe_2$) | Pr | / | F |

Example 17: Model of Inflammatory Angiogenesis in Mice

Angiogenesis is required for the development of chronic inflammatory diseases such as rheumatoid arthritis. The formation of new blood vessels allows not only the perfusion of the pathological tissues but also the transportation of cytokines which are responsible for establishing the chronic state of the disease.

The model described by Colville-N H et al. in 1995 makes it possible to study pharmacological agents that are capable of modulating the appearance of angiogenesis in an inflammatory context. The model is developed on female OF1 mice (Charles River laboratories) weighing about 25 g, and per group of 12. The animals are anaesthetized intraperitoneally with pentobarbital sodium (60 mg/kg; Sanofi Nutrition Santé Animale). An air pocket is created on the mouse's back by injecting 3 ml of air subcutaneously. After waking up, the animals receive a treatment in general by gavage and receive an injection of 0.5 ml of Freud's adjuvant (Sigma) with 0.1% croton oil (Sigma) into the pocket. Seven days later, the mice are again anaesthetized and placed on a hotplate at 40° C. 1 ml of carmine red (Aldrich Chemicals, 5% in 10% of gelatin) is injected into the caudal vein. The animals are then placed at 4° C. for 2-3 hours. The skins are then removed and dried for 24 hours in an oven at 56° C. The dry tissues are weighed and placed in 1.8 ml of digestion solution (dithiothreitol 2 mM, $Na_2HPO_4$ 20 mM, EDTA 1 mM, papain 12 U/ml) for 24 hours. The dye is then dissolved in 0.2 ml of 5M NaOH. The skins are centrifuged at 2000 rpm for 10 minutes at room temperature. The supernatants are filtered through 0.2 μm cellulose acetate membranes. The filtrates are read in a spectrophotometer at 492 nm against a calibration range of carmine red. Two parameters are studied: the dry weight of the granuloma and the amount of dye after digestion of the tissues. The results are expressed as mean values (±sem). The differences between the groups are tested with an ANOVA followed by a Dunnett test, in which the reference group is the "solvent control" group.

The FGF-R antagonists are evaluated between 1 and 50 mg/kg using methylcellulose/Tween (0.6% v/v) as vehicle or any other vehicle that enables dissolution of the active principle. The molecules are daily administered orally (once or twice a day) by gavage. The antagonists of the present invention are considered as active if they enable either a significant reduction in the mass of the granuloma by measuring the mass of the dried skin, or a significant reduction in the angiogenic parameter by measuring the amount of carmine red dye in the skins of the treated animals.

Example of evaluation of FGF-R antagonists in the model of inflammatory angiogenesis in mice. Compound 46 (Example 1) at 30 mg/kg, after one week of the treatment, significantly reduces the weight of granuloma (dry weight of the skin; FIG. 2).

In general, the FGFs and their receptors are significantly involved, via autocrine, paracrine or juxtacrine secretions, in the phenomena of deregulation of stimulation of the growth of cancer cells. Furthermore, FGFs and the receptors thereof affect tumour angiogenesis, which plays a predominant role both on the growth of tumour and also on the metastatic phenomena.

Angiogenesis is a process of generation of new capillaries from pre-existing blood vessels or by mobilization and differentiation of bone marrow cells. Thus, both uncontrolled proliferation of endothelial cells and mobilization of angioblasts from bone marrow are observed in the processes of tumour neovascularization. It has been shown in vitro and in vivo that several growth factors stimulate endothelial proliferation, and especially FGF-1 or a-FGF and FGF-2 or b-FGF. These two factors induce proliferation, migration and the production of proteases by the endothelial cells in culture and neovascularization in vivo. a-FGF and b-FGF interact with the epithelial cells via two classes of receptor, the high-affinity receptors with tyrosine kinase activity (FGF-R) and the low-affinity receptors of heparan sulfate proteoglycan (HSPG) type located at the surface of the cells and in the extracellular matrices. While the paracrine role of these two factors on endothelial cells is widely described, these FGFs might also intervene on these cells by means of an autocrine process. Thus, FGFs and their receptors represent very pertinent targets for therapies directed towards inhibiting angiogenesis processes (Keshet E., Ben-Sasson S. A., J. Clin. Invest, (1999), vol. 501, pp. 104-1497; Presta M., Rusnati M., Dell'Era P., Tanghetti E., Urbinati C., Giuliani R. et al., New York: Plenum Publishers, (2000), pp. 7-34, Billottet C., Janji B., Thiery J. P., Jouanneau J., Oncogene, (2002) vol. 21, pp. 8128-8139).

Moreover, systematic studies aimed at determining the expression due to FGFs and their receptors (FGF-R) on various tumour cell types reveal that a cellular response to these factors is functional in a large majority of studied human tumour lines. These results support the hypothesis that an FGF receptor antagonist might also inhibit the proliferation of tumour cells (Chandler L. A., Sosnowski B.

A., Greenlees L., Aukerman S. L., Baird A., Pierce G. F., *Int. J. Cancer*, (1999), vol. 58, pp. 81-451).

FGFs play an important role in the growth and maintenance of prostate cells. It has been shown both in animal models and in man that an impairment of the cellular response to these factors plays a fundamental role in the progress of prostate cancer. Specifically, in these pathologies, an increase in the production of a-FGF, b-FGF, FGF-6, FGF-8, etc. by the fibroblasts, stromal cells, residual basal cells and endothelial cells present in the tumour and an increase in the expression of the FGF receptors and of the ligands by the tumour cells are recorded. Thus, paracrine stimulation of the cancer cells of the prostate operates, and this process is considered to be a major component of this pathology. A compound with FGF receptor antagonist activity such as the compounds of the present invention might represent a therapy of choice in these pathologies (Giri D., Ropiquet F., *Clin. Cancer Res.*, (1999), vol. 71, pp. 5-1063; Doll J. A., Reiher F. K., Crawford S. E., Pins M. R., Campbell S. C., Bouck N. P., *Prostate*, (2001), vol. 305, pp. 49-293) (Sahadevan et al., 2007) (Kwabi-Addo et al., 2004).

Several studies show the presence of FGFs and of their FGF-R receptors both in human mammary tumour lines (especially MCF7) and in tumour biopsies. These factors are thought to be responsible in this pathology for the appearance of a very aggressive phenotype that induces strong metastasization. Thus, a compound with FGF-R receptor antagonist activity, such as the compounds of formula I, may represent a therapy of choice in these pathologies (Vercoutter-Edouart A-S, Czeszak X, Crépin M, Lemoine J, Boilly B, Le Bourhis X et al., *Exp. Cell Res.*, (2001), vol. 262, pp. 59-68) (Schwertfeger, 2009).

Cancerous melanomas are tumours that induce metastases in high frequency and that are highly resistant to the various chemotherapy treatments. Angiogenesis processes play a predominant role in the progress of a cancerous melanoma. Furthermore, it has been shown that the probability of appearance of metastases increases very greatly as the vascularization of the primary tumour increases. Melanoma cells produce and secrete various angiogenic factors including a-FGF and b-FGF. Moreover, it has been shown that inhibition of the cellular effect of these two factors by the soluble FGF-R1 receptor blocks the proliferation and survival of tumoral melanoma cells in vitro and blocks the tumour progress in vivo. Thus, a compound with FGF receptor antagonist activity, such as the compounds of the present invention, may represent a therapy of choice in these pathologies (Rofstad E. K., Halsor E. F., *Cancer Res.*, (2000); Yayon A., Ma Y-S, Safran M., Klagsbrun M., Halaban R., *Oncogene*, (1997), vol. 14, pp. 2999-3009).

Glioma cells produce a-FGF and b-FGF in vitro and in vivo and have various FGF receptors at their surface. This therefore suggests that these two factors via an autocrine and paracrine effect play a pivotal role in the progress of this type of tumour. Furthermore, as for the majority of solid tumours, the progress of gliomas and their capacity to induce metastases is very much dependent on the angiogenesis processes in the primary tumour. It has also been shown that FGF-R1 receptor antisense factors block the proliferation of human astrocytomas. Furthermore, naphthalenesulfonates are described for inhibiting the cellular effects of a-FGF and b-FGF in vitro and the angiogenesis induced by these growth factors in vivo. Intracerebral injection of these compounds induces a very significant increase in apoptosis and a substantial decrease in angiogenesis, reflected by considerable regression of gliomas in rats. Thus, a compound with a-FGF and/or b-FGF and/or FGF receptor antagonist activity, such as the compounds of the present invention, may represent a therapy of choice in these pathologies (Yamada S. M., Yamaguchi F., Brown R., Berger M. S., Morrison R. S., *Glia*, (1999), vol. 76, pp. 28-66; Auguste P., Gürsel D. B., Lemière S., Reimers D., Cuevas P., Carceller F. et al., *Cancer Res.*, (2001), vol. 26, pp. 61-1717) (Loilome et al., 2008).

Active angiogenesis is also described for hepatocarcinomas or hepatocellular carcinoma (HCC). in vivo, the tumour progress of HCC necessitates a substantial supply of oxygen and nutrients. Hepatocarcinomas are typically angiogenic tumours, since drastic impairment is observed in the arterial vascularization, and that this leads to the acquisition of an invasive and metastatic potential (Tanaka et al., 2006). FGFs actively participate in the development of tumoral angiogenesis in HCCs and are frequently associated with the inflammatory process. They are also overexpressed in the case of chronic hepatitis and cirrhosis of the liver (Uematsu et al., 2005), and the level of FGF in the serum has been correlated with the clinico-pathological progress of HCCs. Furthermore, the FGF-R4 and FGF-R1 receptors have been described as actively participating in the tumour genesis of HCCs (Huang et al., 2006) (Nicholes et al., 2002). The antagonists of the present invention may thus be a treatment of choice for hepatocellular carcinomas or hepatocarcinomas.

In lung cancers of NSCLC type (non-small-cell lung cancer), recent studies show that b-FGF, FGF-9, FGF-R1 and FGF-R2 are regularly co-expressed in the NSCLC cancer lines and especially in those resistant to the anti-EGFR treatment such as gefitinib. These expressions are in relation with the capacity for proliferation by autocrine cellular signalling and for independent growth of an anchoring of tumours of NSCLC type and mainly that which is insensitive to treatment with gefitinib (Marek et al., 2008). Furthermore, b-FGF has been suggested as playing an important role in the survival of NSCLC cells during chemotherapy treatment by inducing the overexpression of the anti-apoptosis proteins BCL-2, BCL-X, XIAP or BIRC3 (PArdo et al., 2002, 2003 and 2006). Thus, an FGF receptor antagonist such as those of the present invention may represent a therapy of choice for lung cancers of NSCLC type, alone or in combination with EGF receptor inhibitors or chemotherapies.

In about 10% of stomach cancers, a gene amplification of FGF-R2 is observed. This amplification is associated with a poor vital prognosis for cancers of diffuse type. The proliferation of the tumour cells may be independent of the ligand or dependent on paracrine activation with FGF-7 (Turner et al., 2010). The antagonists of the present invention may thus be a treatment of choice for stomach cancers.

More recently, the potential role of pro-angiogenic agents in leukaemias and lymphomas has been documented. Specifically, in general, it has been reported that cellular clones in these pathologies either may be naturally destroyed by the immune system or may transform into an angiogenic phenotype that favours their survival and then their proliferation. This change of phenotype is induced by an overexpression of angiogenic factors especially by the macrophages and/or mobilization of these factors from the extracellular matrix (Thomas D. A., Giles F. J., Cortes J., Albitar M., Kantarjian H. M., *Acta Haematol.*, (2001), vol. 207, pp. 106-190). Among the angiogenic factors, b-FGF has been detected in numerous lymphoblastic and haematopoietic tumoral cell lines. FGF receptors are also present on the majority of these lines, suggesting a possible autocrine cellular effect of a-FGF and b-FGF inducing the proliferation of these cells. Moreover, it has been reported that the angiogenesis of bone marrow via paracrine effects was correlated to the progress of some of these pathologies.

More particularly, it has been shown in CLL (chronic lymphocytic leukaemia) cells that b-FGF induces an increase in the expression of anti-apoptotic protein (Bcl2) leading to an increase in the survival of these cells, and thus participates substantially in their cancerization. Furthermore, the levels of b-FGF measured in these cells are highly correlated with the degree of clinical advancement of the disease and the resistance to chemotherapy applied in this pathology (fludarabine). Thus, a compound with FGF receptor antagonist activity, such as the compounds of the present invention, may represent a therapy of choice alone or in combination with fludarabine or other products that are active in this pathology (Thomas D. A., Giles F. J., Cortes J., Albitar M., Kantarjian H. M., *Acta Haematol.*, (2001), vol. 207, pp. 106-190; Gabrilove J. L., *Oncologist*, (2001), vol. 6, pp. 4-7).

Furthermore, it has been shown in numerous recent studies that FGFs and FGF-Rs participate actively in the resistance of tumoral and/or endothelial cells to chemotherapy or radiotherapy treatments or alternatively to anti-VEGF therapies. These resistances involve different cell mechanisms such as protection against apoptosis by a positive regulation of the protein Bcl-xl by FGF-R4 in the case of resistance of breast cancer to doxorubicin (Roidl et al., 2009) or the production of FGF-2 in the case of a resistance to cisplatin of bladder tumours (Miyake et al., 1998), by activation of the Pi3K/AKT pathway by the FGF2/FGF-R1 couple in the case of the resistance to cytarabine of acute myeloid leukaemia cells (Karajannis et al., 2006), by stimulation of the RAS/MAP-K, PI3-K and mTOR pathway by FGF-1 for certain mammary tumours resistant to anti-oestrogen treatments (Manuvakhova et al., 2006). The FGFs/FGF-Rs couple is also involved in resistance to anti-VEGF treatments in the context of pancreatic carcinomas (Casanovas et al., 2005) or glioblastomas (Batchelor et al., 2007) or alternatively in radiotherapy resistance phenomena (Gu et al., 2004; Moyal et al., 2009). Thus, the compounds of the present invention could be combined with the existing therapies to limit the appearance of resistance phenomena.

Furthermore, tumour innovation, which is one of the hallmarks of malignancy, consists of the translocation of tumour cells from the initial neoplastic focus to the surrounding host tissues, enabling the tumour to penetrate into the vascular endothelial in order to circulate and to form metastatic foci remote from the primary tumour. An increasing number of recent articles suggest that changes in tissue architecture at the periphery of the tumour are the cause of the epithelial-mesenchymal transition (EMT). EMT is a cell process via which epithelial cells modulate their phenotype and acquire properties of mesenchymal cells by disrupting intercellular adhesion and increasing cell motility, thus playing a crucial role in tumour progress by imparting an invasive and metastatic phenotype to carcinomas. Growth factors such as FGFs participate in this cell process by means of their stimulatory activity on cell migration and invasion, but also, for the FGF receptors, via their capacity to interact with cadherins, thus facilitating the migration of tumour cells (Cowin et al., 2005). The FGF-R antagonists described here may be used to prevent these metastatic phases of a large number of cancers.

There is a correlation between the angiogenesis process of bone marrow and "extramedullar disease" in CML (chronic myelomonocytic leukaemia). Various studies demonstrate that the inhibition of angiogenesis, in particular by a compound with FGF receptor antagonist activity, might represent a therapy of choice in this pathology.

The proliferation and migration of vascular smooth muscle cells contributes towards intimal hypertrophy of the arteries and thus plays a predominant role in atherosclerosis and in restenosis after angioplasty and endoarterectomy.

in vivo studies show, after lesion of the carotid artery by "balloon injury", a local production of a-FGF and b-FGF. In this same model, an anti-FGF2 neutralizing antibody inhibits the proliferation of the vascular smooth muscle cells and thus decreases the intimal hypertrophy.

An FGF2 chimeric protein linked to a molecule such as saporin inhibits the proliferation of vascular smooth muscle cells in vitro and intimal hypertrophy in vivo (Epstein C. E., Siegall C. B., Biro S, Fu Y. M., FitzGerald D., *Circulation*, (1991), vol. 87, pp. 84-778; Waltenberger J., *Circulation*, (1997), pp. 96-4083).

Thus, FGF receptor antagonists, such as the compounds of the present invention, represent a therapy of choice, either alone or in combination with antagonist compounds of other growth factors involved in these pathologies such as PDGF, in the treatment of pathologies associated with the proliferation of vascular smooth muscle cells, such as atherosclerosis, post-angioplasty restenosis or restenosis following the insertion of endovascular prostheses (stents) or during aorto-coronary bypasses.

Cardiac hypertrophic arises in response to stress on the ventricular wall induced by an overload in terms of pressure or volume. This overload may be the consequence of numerous physiopathological conditions such as hypertension, AC (aortic coarctation), myocardial infarction and various vascular disorders. The consequences of this pathology are morphological, molecular and functional changes such as hypertrophy of the cardiac myocytes, the accumulation of matrix proteins and the re-expression of foetal genes. b-FGF is involved in this pathology. Specifically, the addition of b-FGF to newborn rat cardiomyocyte cultures modifies the profile of the genes corresponding to the contractile proteins, leading to a gene profile of foetal type. In a complementary manner, adult rat myocytes show a hypertrophic response under the effect of b-FGF, this response being blocked by anti-b-FGF neutralizing antibodies. Experiments performed in vivo on b-FGF "knockout" transgenic mice show that b-FGF is a major stimulating factor of the hypertrophy of cardiac myocytes in this pathology (Schultz JeJ, Witt S. A., Nieman M. L., Reiser P. J., Engle S. J., Zhou M. et al., *J. Clin. Invest.*, (1999), vol. 19, pp. 104-709). Thus, a compound with FGF receptor antagonist activity, such as the compounds of the present invention, represents a therapy of choice in the treatment of cardiac insufficiency and any other pathology associated with degeneration of cardiac tissue. This treatment could be performed alone or in combination with common treatments (beta-blockers, diuretics, angiotensin antagonists, antiarrhythmics, anti-calcium, antithrombotic etc. agents).

Diabetes-related vascular disorders are characterized by an impairment of vascular reactivity and of the blood flow, hyperpermeability, an exacerbated proliferative response and an increase in matrix protein deposits. More precisely, a-FGF and b-FGF are present in the preretinal membranes of patients with diabetic retinopathy, in membranes of the subjacent capillaries and in the vitreous humour of patients suffering from proliferative retinopathy. A soluble FGF receptor that is capable of binding both to a-FGF and b-FGF is developed in diabetes-related vascular disorders (Tilton R. G., Dixon R. A. F., Brock T. A., *Exp. Opin. Invest. Drugs*, (1997), vol. 84, pp. 6-1671). Thus, a compound with FGF receptor antagonist activity, such as the compounds of formula I, represents a therapy of choice either alone or in combination with compounds that are antagonists of other growth factors involved in these pathologies, for instance VEGF, such as the anti-VEGF therapy mentioned above.

Fibrosis is the abnormal formation of scar tissue following a tissue lesion, and leads to chronic and progressive impairment of the affected organ, which may result in serious dysfunction of the affected organ. It may arise in any tissue, but is mainly prevalent in organs exposed to chemical or biological attack, such as the lungs, the skin, the kidneys, the digestive tube, the liver, etc. FGFs participate in this cell process and promote the production and accumulation of extracellular matrices by the fibroblasts, and their proliferation and infiltration into numerous organs such as the kidneys or the lungs (Khalil et al., 2005) (Strutz et al., 2003). Antagonists of the activity of these FGFs, such as the molecules of the present invention, may be used alone or in combination in the treatment of fibrosis.

Rheumatoid arthritis (RA) is a chronic disease of unknown aetiology. Although it affects numerous organs, the most severe form of RA is gradual synovial inflammation of the joints, leading to their destruction. Angiogenesis appears to substantially affect the progress of this pathology. Thus, a-FGF and b-FGF have been detected in synovial tissue and in the articular fluid of patients suffering from RA, indicating that this growth factor intervenes in the initiation and/or progress of this pathology. In models of AIA (adjuvant-induced model of arthritis) in rats, it has been shown that the overexpression of b-FGF increases the severity of the disease, whereas an anti-b-FGF neutralizing antibody blocks the progress of RA (Malemud, 2007) (Yamashita A, Yonemitsu Y, Okano S, Nakagawa K, Nakashima Y, Irisa T et al., *J. Immunol.*, (2002), vol. 57, pp. 168-450; Manabe N, Oda H, Nakamura K, Kuga Y, Uchida S, Kawaguchi H, *Rheumatol*, (1999), vol. 20, pp. 38-714). Thus, the compounds according to the invention represent a therapy of choice in this pathology.

Recent scientific articles document the involvement of b-FGF in neuropathic pain. Specifically, an increase in the production of astroglial b-FGF is observed in astrocytes following lesion of the spinal cord (Madiai et al., 2003). This b-FGF contributes towards the neuropathic contact pain or allodynia. Treatment using an anti-FGF2 neutralizing antibody reduces this mechanical allodynia (Madiai et al., 2005). The antagonists of the present invention are treatments of choice for pain by inhibiting the effect of FGF-2 on these receptors.

It has also been described that the levels of growth factors with pro-angiogenic activity such as FGF-1 and -2 were greatly increased in the synovial fluid of patients suffering from osteoarthritis. In this type of pathology, a substantial modification is recorded in the balance between the pro- and anti-angiogenic factors inducing the formation of new blood vessels, and consequently the vascularization of non-vascularized structures such as articular cartilage or intervertebral discs. Thus, angiogenesis represents a key factor in bone formation (osteophytes), thus contributing towards the progress of the disease. In a complementary manner, the innervation of new blood vessels may also contribute towards the chronic pain associated with this pathology (Walsh D. A., Curr. Opin. Rheumatol. 2004 September; 16(5):609-15) Thus, the compounds according to the invention represents a therapy of choice in this pathology.

IBD (inflammatory bowel disease) comprises two forms of chronic inflammatory disease of the intestine: UC (ulcerative colitis) and Crohn's disease (CD). IBD is characterized by an immune dysfunction that is reflected by an inappropriate production of inflammatory cytokines, inducing the establishment of a local microvascular system. A consequence of this angiogenesis of inflammatory origin is a vasoconstriction-induced intestinal ischaemia. Substantial circulating and local levels of b-FGF have been measured in the case of patients suffering from these pathologies (Kanazawa S, Tsunoda T, Onuma E, Majima T, Kagiyama M, Kkuchi K., *American Journal of Gastroenterology*, (2001), vol. 28, pp. 96-822; Thorn M, Raab Y, Larsson A, Gerdin B, Hallgren R., *Scandinavian Journal of Gastroenterology*, (2000), vol. 12, pp. 35-408). The compounds of the invention with substantial anti-angiogenic activity in a model of inflammatory angiogenesis represent a therapy of choice in these pathologies.

Another disease with a substantial inflammatory component and for which a strong involvement of the FGFs and FGF-Rs is described is benign prostate hyperplasia (BPH). BPH is an age-related disease which is characterized by hyperplasia of the glandular tissues and of stroma around the urethra up to the point of its obstruction. At the cellular level, this pathology involves hyperplasia of the basal cells, an increase in the stromal mass, an amplified deposition of matrix or a reduction in the elasticity of the tissues (Untergasser et al., 2005). FGFs participate in the development of this disease by stimulating the proliferation of the prostate stromal and epithelial cells and especially FGF-7 or KGF, but also FGF-2 or FGF-17 (Wang 2008, Boget 2001, Giri 2001). Furthermore, the FGFs promote the transdifferentiation step by modifying the epithelial cellstromal cell interactions, in combination with TGF-$\beta$ (Untergasser 2005). Finally, certain receptors such as FGF-R1 are overexpressed in BPH, promoting induction of the pathology and potentiating the paracrine effects of FGF-2 (Boget 2001). An antagonist of the effect of these FGFs is thus a treatment of choice for benign prostate hyperplasia.

Psoriasis is a chronic skin disease caused by hyperproliferation of the epidermal keratinocytes, while clear cell acanthoma (CCA) is a benign epidermal neoplasm also involving abnormal keratinocyte proliferation. These two skin diseases have similar histological characteristics despite having different underlying causes: thickening of the epidermis, inflammatory infiltrations of lymphocytes and neutrophils, dilation and tortuosity of the papillary capillaries. In both cases, KGF or FGF-7 µlays an a predominant role in the development of the pathology (Kovacs et al., 2006) (Finch et al., 1997). The use of the antagonists of the present invention may make it possible to slow down the development of such skin diseases.

FGF-R1, -R2 and -R3 are involved in chronogenesis and osteogenesis processes. Mutations leading to the expression of FGF-Rs that are always activated have been linked to a large number of human genetic diseases reflected by skeletal malformations, such as the Pfeiffer, Crouzon, Apert, Jackson-Weiss and Bear-Stevenson cutis gyrata syndromes. Some of these mutations more particularly affecting the FGF-R3 receptor lead especially to achondroplasias (ACH), hypochondroplasias (HCH) and TD (thanatophoric dysplasia); ACH being the most common form of dwarfism. From a biochemical viewpoint, the sustained activation of these receptors takes place via dimerization of the receptor in the absence of ligand (Chen L., Adar R., Yang X. Monsonego E. O., LI C., Hauschka P. V., Yagon A. and Deng C. X., (1999), *The Journ. of Clin. Invest.*, vol. 104, No. 11, pp. 1517-1525). Thus, the compounds of the invention with antagonist activity towards the FGFs or the FGF receptors and which inhibit FGF-R-dependent intracellular signalling represent a therapy of choice in these pathologies.

Moreover, it is known that adipose tissue is one of the rare tissues that can develop or regress in adults. This tissue is highly vascularized and a very dense network of microvessels surrounds each adipocyte. These observations led to testing of the effect of anti-angiogenic agents on the development of adipose tissue in adults. Thus, it appears that in pharmacological models in ob/ob mice, the inhibition of angiogenesis is reflected by a significant loss of weight of the mice (Rupnick M. A. et al, (2002), *PNAS*, vol. 99, No. 16, pp. 10730-10735). Furthermore, FGFs appear as key regulators of adipogenesis in man (Hutley et al., 2004). Thus, an FGF receptor antagonist compound with powerful anti-angiogenic activity may represent a therapy of choice in obesity-related pathologies.

By virtue of their low toxicity and their pharmacological and biological properties, the compounds of the present invention find their use in the treatment and prevention of any carcinoma having a substantial degree of vascularization, such as lung, breast, prostate, oesophageal, pancreatic, liver, bowel or kidney carcinomas or which induce metastases, such as bowel, breast, liver and stomach carcinomas, melanomas, or which are sensitive to a-FGF or to b-FGF in an autocrine manner, or alternatively in pathologies such as glioma, lymphoma and leukaemia, or finally in any therapy-resistance phenomenon. These compounds represent a therapy of choice either alone or in combination with chemotherapy, radiotherapy or any other suitable treatment. The compounds according to the invention also find their use in the treatment and prevention of cardiovascular diseases such as atherosclerosis, post-angioplasty restenosis, in the treatment of diseases associated with complications arising after the insertion of endovascular prostheses and/or aorto-coronary bypasses or other vascular grafts and cardiac hypertrophy or vascular complications of diabetes such as diabetic retinopathy. The compounds according to the invention also find their use in the treatment and prevention of chronic inflammatory diseases such as rheumatoid arthritis, IBD or benign prostate hyperplasia. Finally, the compounds according to the invention may be used in the treatment and prevention of achondroplasias (ACH), hypochondroplasias (HCH) and TD (thanatophoric dysplasia), and also in the treatment of obesity.

The products according to the invention also find their use in the treatment and prevention of macular degeneration, especially age-related macular degeneration (AMD). A major feature of the loss of vision in adults is the consecutive neovascularization and haemorrhaging, which cause major functional disorders in the eye and which are reflected by early-onset blindness. Recently, study of the mechanisms involved in ocular neovascularization phenomena have revealed the involvement of pro-angiogenic factors in these pathologies. By using a model of laser-induced choroid neoangiogenesis, it has been possible to confirm that the products according to the invention also make it possible to modulate the neovascularization of the choroid.

Moreover, the products of the invention may be used in the treatment or prevention of thrombopenia caused especially by anticancer chemotherapy. Specifically, it has been demonstrated that the products of the invention can improve the levels of circulating platelets during chemotherapy.

Finally, the products according to the invention find a use in the treatment and prevention of skin diseases such as psoriasis or clear-cell acanthoma, in combating the progress of hepatic, renal or pulmonary fibrosis, and also in the treatment of neuropathic pain.

According to another of its aspects, a subject of the invention is medicaments comprising a compound of formula (I), or a pharmaceutically acceptable acid-addition or base-addition salt thereof.

These medicaments find their use in the treatment and prevention of any carcinoma having a substantial degree of vascularization, such as lung, breast, prostate, oesophageal, pancreatic, liver, bowel or kidney carcinomas or which induce metastases, such as bowel, breast, liver and stomach carcinomas, melanomas, or which are sensitive to a-FGF or to b-FGF in an autocrine manner, or alternatively in pathologies such as glioma, lymphoma and leukaemia, or finally in any therapy-resistance phenomenon. These medicaments also find their use in the treatment and prevention of cardiovascular diseases such as atherosclerosis, post-angioplasty restenosis, in the treatment of diseases associated with complications arising after the insertion of endovascular prostheses and/or aorto-coronary bypasses or other vascular grafts and cardiac hypertrophy or vascular complications of diabetes such as diabetic retinopathy. They also find their use in the treatment and prevention of chronic inflammatory diseases such as rheumatoid arthritis, IBD or benign prostate hyperplasia. They may be used in the treatment and prevention of achondroplasias (ACH), hypochondroplasias (HCH) and TD (thanatophoric dysplasia), and also in the treatment of obesity.

The medicaments according to the invention also find their use in the treatment and prevention of macular degeneration, especially age-related macular degeneration (AMD). They also make it possible to modulate neovascularization of the choroid.

Moreover, the medicaments according to the invention may be used in the treatment or prevention of thrombopenia caused especially by anticancer chemotherapy.

A subject of the present invention is also the use of a compound of formula (I) as defined above, for its use in the treatment and prevention of diseases necessitating a modulation of the FGFs.

A subject of the present invention is also the use of a compound of formula (I), as defined above, for its use in the treatment and prevention of cancers, especially carcinomas with a substantial degree of vascularization such as lung, breast, prostate, pancreatic, bowel, kidney and oesophageal carcinomas, cancers that induce metastases, such as bowel cancer, liver cancer and stomach cancer, melanomas, gliomas, lymphomas and leukaemias.

A compound of formula (I) according to the present invention may be administered alone or in combination with one or more compounds with anti-angiogenic activity or with one or more cytotoxic compounds (chemotherapy), or alternatively in combination with a radiotherapy. Thus, a subject of the present invention is also the use of a compound of formula (I) as defined above in combination with one or more anticancer active principles and/or with a radiotherapy.

A subject of the present invention is also the use of a compound of formula (I), as defined above, in the treatment and prevention of cardiovascular diseases such as atherosclerosis, post-angioplasty restenosis, in the treatment of diseases associated with complications arising after the insertion of endovascular prostheses and/or aorto-coronary bypasses or other vascular grafts and cardiac hypertrophy, or in the treatment of vascular complications of diabetes such as diabetic retinopathy.

A subject of the present invention is also the use of a compound of formula (I), as defined above, in the treatment or prevention of chronic inflammatory diseases such as rheumatoid arthritis or IBD.

A subject of the present invention is also the use of a compound of formula (I), as defined above, in the treatment or prevention of osteoarthritis, achondroplasias (ACH), hypochondroplasias (HCH) and TD (thanatophoric dysplasia).

A subject of the present invention is also the use of a compound of formula (I), as defined above, in the treatment or prevention of obesity.

A subject of the present invention is also the use of a compound of formula (I), as defined above, in the treatment or prevention of macular degeneration, such as age-related macular degeneration (AMD).

According to another of its aspects, the present invention relates to pharmaceutical compositions comprising, as active principle, a compound of formula (I) according to the invention. These pharmaceutical compositions contain an effective dose of at least one compound according to the invention, or a pharmaceutically acceptable salt, and also at least one pharmaceutically acceptable excipient. The said excipients are chosen, according to the pharmaceutical form and the mode of administration desired, from the usual excipients that are known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the treatment of the disorders or diseases mentioned previously.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical administration, the compounds according to the invention may be used in creams, gels, pomades or lotions.

The pharmaceutical compositions according to the present invention are preferably administered orally.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The present invention also relates to a pharmaceutical composition as defined above, as a medicament.

The compositions according to the invention, for oral administration, contain recommended doses of 0.01 to 700 mg. There may be special cases in which higher or lower dosages are appropriate; such dosages are not outside the scope of the invention. According to the usual practice, the dosage that is appropriate to each patient is determined by the doctor according to the mode of administration, the age, weight and response of the patient, and also according to the degree of progress of the disease.

According to another of its aspects, the present invention also relates to a method for treating the above pathologies, which comprises the administration, to a patient, of an effective dose of a compound according to the invention, or a pharmaceutically acceptable salt or hydrates or solvates thereof.

The invention claimed is:

1. A compound of formula (I') or (I"):

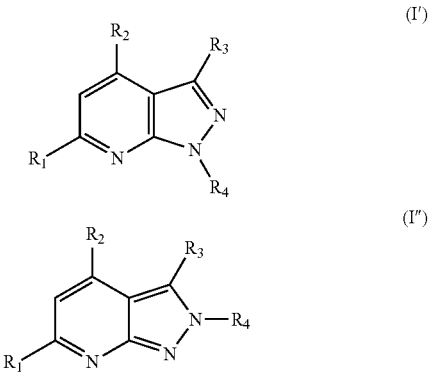

wherein $R_1$ is phenyl substituted with one or more substituents chosen from —$CF_3$, cyano, —$NR_6R_6'$, —$NR_{10}R_{11}$ wherein $R_{10}$ and $R_{11}$ form, together with the nitrogen atom to which they are attached, a saturated or unsaturated heterocycle comprising one or more heteroatoms chosen from a nitrogen atom and an oxygen atom, optionally substituted with one or more substituents chosen from halogen and linear or branched alkyl, —$CH_2NR_{10}R_{11}$ wherein $R_{10}$ and $R_{11}$ form, together with the nitrogen atom to which they are attached, a saturated or unsaturated heterocycle comprising one or more heteroatoms chosen from a nitrogen atom and an oxygen atom, —$COR_{12}$ wherein $R_{12}$ is hydroxyl or —$NR_6R_6'$, —$CONR_7R_7'$ wherein $R_7$ and $R_7'$ form, together with the nitrogen atom to which they are attached, a heterocycloalkyl comprising one or more heteroatoms chosen from a nitrogen atom and an oxygen atom, —$(CH_2)_pNHSO_2CH_3$ wherein p is 0 or 1, —$OR_{13}$ wherein $R_{13}$ is linear ($C_2$-$C_3$)alkyl, and ($C_3$) alkyl, or $R_1$ is pyridyl optionally substituted with one or more substituents chosen from fluorine, —$CF_3$, cyano, —$NR_6R_6'$, —$NR_{10}R_{11}$ wherein $R_{10}$ and $R_{11}$ form, together with the nitrogen atom to which they are attached, a saturated or unsaturated heterocycle comprising one or more heteroatoms chosen from a nitrogen atom and an oxygen atom, optionally substituted with one or more substituents chosen from halogen and linear or branched alkyl, —$CH_2NR_{10}R_{11}$ wherein $R_{10}$ and $R_{11}$ form, together with the nitrogen atom to which they are attached, a saturated or unsaturated heterocycle comprising one or more heteroatoms chosen from a nitrogen atom and an oxygen atom, —$COR_{12}$ wherein $R_{12}$ is hydroxyl or —$NR_6R_6'$, —$CONR_7R_7'$ wherein $R_7$ and $R_7'$ form, together with the nitrogen atom to which they are attached, a heterocycloalkyl comprising one or more heteroatoms chosen from a nitrogen atom and an oxygen atom, —(CH$_2$)$_p$NHSO$_2$CH$_3$ wherein p is 0 or 1, —OR$_{13}$ wherein R$_{13}$ is linear (C$_1$-C$_3$)alkyl, and (C$_2$-C$_3$)alkyl, or R$_1$ is pyrazolyl optionally substituted with one or more substituents chosen from fluorine, —CF$_3$, cyano, —NR$_6$R$_6$', —NR$_{10}$R$_{11}$ wherein R$_{10}$ and R$_{11}$ form, together with the nitrogen atom to which they are attached, a saturated or unsaturated heterocycle comprising one or more heteroatoms chosen from a nitrogen atom and an oxygen atom, optionally substituted with one or more substituents chosen from halogen and linear or branched alkyl, —CH$_2$NR$_{10}$R$_{11}$ wherein R$_{10}$ and R$_{11}$ form together with the nitrogen atom to which they are attached, a saturated or unsaturated heterocycle comprising one or more heteroatoms chosen from a nitrogen atom and an oxygen atom, —COR$_{12}$ wherein R$_{12}$ is hydroxyl or —NR$_6$R$_6$', —CONR$_7$R$_7$' wherein R$_7$ and R$_7$' form, together with the nitrogen atom to which they are attached, a heterocycloalkyl comprising one or more heteroatoms chosen from a nitrogen atom and an oxygen atom, —(CH$_2$)$_p$NHSO$_2$CH$_3$ wherein p is 0 or 1, —OR$_{13}$ wherein R$_{13}$ is linear (C$_1$-C$_3$)alkyl, and (C$_3$)alkyl, or R$_1$ is a bicyclic group of formula A:

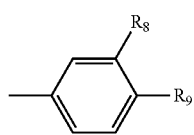

(A)

wherein R$_8$ and R$_9$ form, together with the phenyl ring to which they are attached, a dihydrobenzimidazolonyl, indolyl, dihydrobenzoxazinyl, benzothiazolyl or benzimidazolyl, optionally substituted with one or more linear alkyl groups;

R$_2$ is —CF$_3$, —CHF$_2$, or —CONHR$_5$;

R$_3$ is hydrogen, aryl optionally substituted with alkoxymethyl, or heteroaryl chosen from thienyl and pyridyl;

R$_4$ is hydrogen, (C$_1$)alkyl, linear (C$_3$)alkyl, or linear (C$_1$-C$_3$)alkyl substituted with —NR$_6$R$_6$' or —NR$_7$R$_7$' wherein R$_7$ and R$_7$' form, together with the nitrogen atom to which they are attached, a heterocycloalkyl comprising one or more heteroatoms chosen from a nitrogen atom and an oxygen atom;

R$_5$ is
hydrogen,
linear (C$_1$-C$_3$)alkyl optionally substituted with pyridyl, or
an aromatic group chosen from aryl and pyridyl; and R$_6$ and R$_6$', are independently hydrogen or a linear alkyl group, in the form of the base or of an acid-addition or base-addition salt.

2. A compound that is:
N,N-Dimethyl-4-(1-methyl-3-phenyl-4-trifluoromethyl-1H-pyrazolo[3,4-b]pyridin-6-yl)benzamide;
5-(1-Methyl-3-phenyl-4-trifluoromethyl-1H-pyrazolo[3,4-b]pyridin-6-yl)nicotinonitrile;
6-Benzothiazol-5-yl-1-methyl-3-phenyl-4-trifluoromethyl-1H-pyrazolo[3,4-b]pyridine;
1-Methyl-3-phenyl-6-(6-pyrrolidin-1-ylpyridin-3-yl)-4-trifluoromethyl-1H-pyrazolo[3,4-b]pyridine;
3-(1-Methyl-3-phenyl-4-trifluoromethyl-1H-pyrazolo[3,4-b]pyridin-6-yl)benzamide;
N-[4-(1-Methyl-3-phenyl-4-trifluoromethyl-1H-pyrazolo[3,4-b]pyridin-6-yl)benzyl]methanesulfonamide;
1-Methyl-6-(1-methyl-1H-indol-6-yl)-3-phenyl-4-trifluoromethyl-1H-pyrazolo[3,4-b]pyridine;
N-[3-(1-Methyl-3-phenyl-4-trifluoromethyl-1H-pyrazolo[3,4-b]pyridin-6-yl)phenyl]methanesulfonamide;
4-Methyl-7-(1-methyl-3-phenyl-4-trifluoromethyl-1H-pyrazolo[3,4-b]pyridin-6-yl)-3,4-dihydro-2H-benzo[1,4]oxazine;
N-[3-(1-Methyl-3-phenyl-4-trifluoromethyl-1H-pyrazolo[3,4-b]pyridin-6-yl)benzyl]methanesulfonamide;
6-(4-Methoxyphenyl)-1-methyl-3-phenyl-4-trifluoromethyl-1H-pyrazolo[3,4-b]pyridine;
2-Fluoro-N-methyl-5-(1-methyl-3-phenyl-4-trifluoromethyl-1H-pyrazolo[3,4-b]pyridin-6-yl)benzamide;
Dimethyl[3-(1-methyl-3-phenyl-4-trifluoromethyl-1H-pyrazolo[3,4-b]pyridin-6-yl)phenyl]amine;
6-[4-(3,5-Dimethylpyrazol-1-yl)phenyl]-1-methyl-3-phenyl-4-trifluoromethyl-1H-pyrazolo[3,4-b]pyridine;
1-Methyl-6-(3-morpholin-4-ylmethylphenyl)-3-phenyl-4-trifluoromethyl-1H-pyrazolo[3,4-b]pyridine;
4-(1-Methyl-3-phenyl-4-trifluoromethyl-1H-pyrazolo[3,4-b]pyridin-6-yl)benzoic acid;
N,N-Dimethyl-3-(1-methyl-3-phenyl-4-trifluoromethyl-1H-pyrazolo[3,4-b]pyridin-6-yl)benzamide;
1-Methyl-6-(6-morpholin-4-ylpyridin-3-yl)-3-phenyl-4-trifluoromethyl-1H-pyrazolo[3,4-b]pyridine;
6-(6-Methoxypyridin-3-yl)-1-methyl-3-phenyl-4-trifluoromethyl-1H-pyrazolo[3,4-b]pyridine;
N-Methyl-3-(3-phenyl-4-trifluoromethyl-1H-pyrazolo[3,4-b]pyridin-6-yl)benzamide;
2-Fluoro-5-(1-methyl-3-phenyl-4-trifluoromethyl-1H-pyrazolo[3,4-b]pyridin-6-yl)benzoic acid;
2-Amino-5-(4-difluoromethyl-2-methyl-2H-pyrazolo[3,4-b]pyridin-6-yl)benzonitrile;
N-[3-(3-Phenyl-4-trifluoromethyl-1H-pyrazolo[3,4-b]pyridin-6-yl)phenyl]methanesulfonamide;
6-(4-Amino-3-cyanophenyl)-3-cyclopropyl-1H-pyrazolo[3,4-b]pyridine-4-carboxylic acid;
2-Fluoro-5-(3-phenyl-4-trifluoromethyl-1H-pyrazolo[3,4-b]pyridin-6-yl)benzonitrile;
2-Fluoro-5-(3-phenyl-4-trifluoromethyl-1H-pyrazolo[3,4-b]pyridin-6-yl)benzoic acid;
1-Methyl-6-(2-methyl-5-trifluoromethyl-2H-pyrazol-3-yl)-3-phenyl-4-trifluoromethyl-1H-pyrazolo[3,4-b]pyridine;
N,N-Dimethyl-4-(3-phenyl-4-trifluoromethyl-1H-pyrazolo[3,4-b]pyridin-6-yl)benzamide;
6-(4-Morpholin-4-ylphenyl)-3-phenyl-4-trifluoromethyl-1H-pyrazolo[3,4-b]pyridine;
6-(6-Morpholin-4-ylpyridin-3-yl)-3-phenyl-4-trifluoromethyl-1H-pyrazolo[3,4-b]pyridine;
6-(6-Methoxypyridin-3-yl)-3-phenyl-4-trifluoromethyl-1H-pyrazolo[3,4-b]pyridine;
6-(3-Morpholin-4-ylphenyl)-3-phenyl-4-trifluoromethyl-1H-pyrazolo[3,4-b]pyridine;
3-Phenyl-6-(3-piperidin-1-ylphenyl)-4-trifluoromethyl-1H-pyrazolo[3,4-b]pyridine;
2-Fluoro-N-methyl-5-(3-phenyl-4-trifluoromethyl-1H-pyrazolo[3,4-b]pyridin-6-yl)benzamide;
5-(3-Phenyl-4-trifluoromethyl-1H-pyrazolo[3,4-b]pyridin-6-yl)nicotinonitrile;
Dimethyl[4-(3-phenyl-4-trifluoromethyl-1H-pyrazolo[3,4-b]pyridin-6-yl)phenyl]amine;
4-(3-Phenyl-4-trifluoromethyl-1H-pyrazolo[3,4-b]pyridin-6-yl)phenylamine; or 6-(4-Methoxyphenyl)-3-phenyl-4-trifluoromethyl-1H-pyrazolo[3,4-b]pyridine;
in the form of the base or of an acid-addition or base-addition salt.

3. A compound that is:
N-[3-(3-Phenyl-4-trifluoromethyl-1H-pyrazolo[3,4-b]pyridin-6-yl)-phenyl]-methanesulfonamide;
N-[3-(1-Methyl-3-phenyl-4-trifluoromethyl-1H-pyrazolo[3,4-b]pyridin-6-yl)phenyl]methanesulfonamide];
N-Methyl-3-(3-phenyl-4-trifluoromethyl-1H-pyrazolo[3,4-b]pyridin-6-yl)-benzamide;
6-(4-Methoxy-phenyl)-3-phenyl-4-trifluoromethyl-1H-pyrazolo[3,4-b]pyridine;
Dimethyl-[4-(3-phenyl-4-trifluoromethyl-1H-pyrazolo[3,4-b]pyridin-6-yl)-phenyl]-amine;
4-(1-Methyl-3-phenyl-4-trifluoromethyl-1H-pyrazolo[3,4-b]pyridin-6-yl)-benzoic acid; or
6-(4-Morpholin-4-yl-phenyl)-3-phenyl-4-trifluoromethyl-1H-pyrazolo[3,4-b]pyridine;
in the form of the base or of an acid-addition or base-addition salt.

4. A compound that is:
4-[4-(difluoromethyl)-3-phenyl-1H-pyrazolo[3,4-b]pyridin-6-yl]aniline; or
4-(difluoromethyl)-3,6-diphenyl-1H-pyrazolo[3,4-b]pyridine;
in the form of the base or of an acid-addition or base-addition salt.

5. A pharmaceutical composition comprising a compound of claim 1, in the form of the base or of an acid-addition or base-addition salt, or a pharmaceutically acceptable salt thereof, and at least one pharmaceutically acceptable excipient.

6. A pharmaceutical composition comprising a compound of claim 3, in the form of the base or of an acid-addition or base-addition salt, or a pharmaceutically acceptable salt thereof, and at least one pharmaceutically acceptable excipient.

7. A pharmaceutical composition comprising a compound of claim 4, in the form of the base or of an acid-addition or base-addition salt, or a pharmaceutically acceptable salt thereof, and at least one pharmaceutically acceptable excipient.

8. A pharmaceutical composition comprising a compound selected form the following compounds:

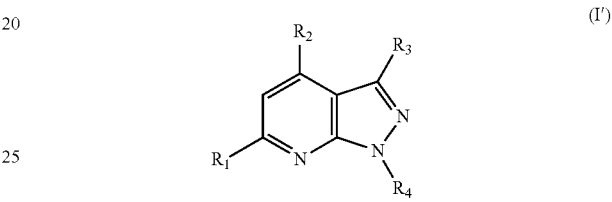

(I')

wherein $R_1$, $R_2$, $R_3$ and $R_4$ are defined as follows:

| $R_2$ | $R_3$ | $R_1$ | $R_4$ |
|---|---|---|---|
| $CF_3$ | Ph | 3-($CONH_2$)phenyl | Me |
| $CF_3$ | Ph | 4-($NHSO_2Me$)benzyl | Me |
| $CF_3$ | Ph | 1-methyl-6-indolyl | Me |
| $CF_3$ | Ph | 3-($NHSO_2Me$)phenyl | Me |
| $CF_3$ | Ph | 4-methyl-3,4-dihydro-2H-benzo[1,4]oxazin-6-yl | Me |
| $CF_3$ | Ph | 4-($NHSO_2Me$)benzyl | Me |

-continued

| R₂ | R₃ | R₁ | R₄ |
|---|---|---|---|
| CF₃ | Ph | 4-methoxyphenyl | Me |
| CF₃ | Ph | 2-fluoro-5-methyl-N-methylbenzamide | Me |
| CF₃ | Ph | 3-(dimethylamino)-5-methylphenyl | Me |
| CF₃ | Ph | 4-(3,5-dimethyl-1H-pyrazol-1-yl)phenyl | Me |
| CF₃ | Ph | 3-(morpholinomethyl)phenyl | Me |
| CF₃ | Ph | 5-cyanopyridin-3-yl | Me |
| CF₃ | Ph | 4-carboxyphenyl | Me |
| CF₃ | Ph | 4-(dimethylcarbamoyl)phenyl | me |
| CF₃ | Ph | 3-(dimethylcarbamoyl)phenyl | Me |
| CF₃ | Ph | 6-morpholinopyridin-3-yl | me |
| CF₃ | Ph | 6-methoxypyridin-3-yl | Me |
| CF₃ | Ph | 6-(pyrrolidin-1-yl)pyridin-3-yl | Me |

-continued

| R₂ | R₃ | R₁ | R₄ |
|---|---|---|---|
| CF₃ | Ph | 1,5-dimethyl-3-(trifluoromethyl)-1H-pyrazol-4-yl | Me |
| CF₃ | Ph | 6-methylbenzo[d]thiazol-5-yl | Me |
| CF₃ | Ph | 4-(dimethylcarbamoyl)phenyl | H |
| CF₃ | Ph | 4-morpholinophenyl | H |
| CF₃ | Ph | 5-morpholinopyridin-2-yl | H |
| CF₃ | Ph | 6-methoxypyridin-3-yl | H |
| CF₃ | Ph | 3-morpholinophenyl | H |
| CF₃ | Ph | 3-(N-methylcarbamoyl)phenyl | H |
| CF₃ | Ph | 3-(methylsulfonamido)phenyl | H |
| CF₃ | Ph | 3-(piperidin-1-yl)phenyl | H |
| CF₃ | Ph | 2-fluoro-4-(N-methylcarbamoyl)phenyl | H |

-continued

| R₂ | R₃ | R₁ | R₄ |
|---|---|---|---|
| CF₃ | Ph | 5-cyano-pyridin-3-yl (methyl-substituted) | H |
| CHF₂ | Ph | 4-(pyrrolidine-1-carbonyl)phenyl | H |
| CHF₂ | Ph | 1-methyl-1H-pyrazol-4-yl | H |
| CHF₂ | Ph | 3,4,5-trimethyl-1H-pyrazol-4-yl | H |
| CHF₂ | Ph | 4-methyl-1H-pyrazol-3-yl | H |
| CHF₂ | Ph | 6-methoxypyridin-3-yl | H |
| CHF₂ | Ph | 3-(pyrrolidine-1-carbonyl)phenyl | H |
| CHF₂ | Ph | 3-(piperidin-1-yl)phenyl | H |
| COOH | H | 4-amino-3-methoxyphenyl | H |
| CONHMe | Ph | 4-amino-3-methoxyphenyl | H |
| CONH₂ | Ph | 4-amino-3-methoxyphenyl | H |

-continued

| R₂ | R₃ | R₁ | R₄ |
|---|---|---|---|
| CONHMe | H | 4-methyl-2-amino-3-methoxyphenyl | H |
| CONH₂ | H | 4-methyl-2-amino-3-methoxyphenyl | H |
| COOH | Ph | 4-methyl-2-amino-3-methoxyphenyl | H |
| COOH | Ph | 4-methyl-2-amino-3-methoxyphenyl | Me |
| COOH | H | 4-methyl-2-amino-3-methoxyphenyl | Me |
| CONH₂ | Ph | 4-methyl-2-fluoro-3-carboxyphenyl | H |
| CONH₂ | Ph | 4-methyl-2-amino-3-carboxyphenyl | H |
| CONH₂ | Ph | 4-methyl-2-amino-3-cyanophenyl | H |
| CONH₂ | 2-thienyl | 4-methyl-2-amino-3-cyanophenyl | H |
| COOH | cPr | 4-methyl-2-amino-3-cyanophenyl | H |
| CONH₂ | H | 4-methyl-2-fluoro-3-carboxyphenyl | H |

-continued

| R₂ | R₃ | R₁ | R₄ |
|---|---|---|---|
| CONH₂ | Ph | 2-F, 3-CN phenyl | H |
| CHF₂ | Ph | 2-F, 3-COOH phenyl | H |
| CF₃ | Ph | 2-F, 3-CN phenyl | H |
| CHF₂ | Ph | 2-NH₂, 3-CN phenyl | H |
| CF₃ | Ph | 2-F, 3-COOH phenyl | H |
| CF₃ | Ph | 2-NH₂, 3-CN phenyl | Me |
| CF₃ | Ph | 2-F, 3-COOH phenyl | Me |
| CF₃ | Ph | 1H-indol-5-yl | H |
| CF₃ | Ph | 2-oxo-2,3-dihydro-1H-benzimidazol-5-yl | H |
| CF₃ | Ph | 4-NMe₂ phenyl | H |
| CONHPh | H | 2-NH₂, 3-CN phenyl | H |

-continued
| R₂ | R₃ | R₁ | R₄ |
|---|---|---|---|
| 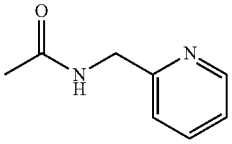 | H | 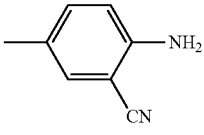 | H |
| 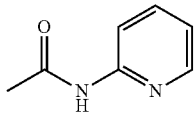 | H | 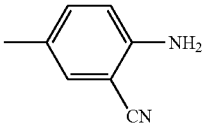 | H |
| 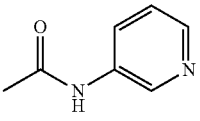 | H | 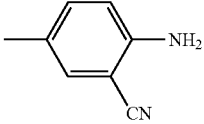 | H |
| 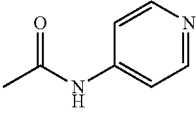 | H | 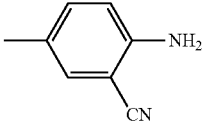 | H |
| CHF₂ | 4-Py | 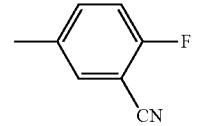 | Me |
| CONHPh | H | 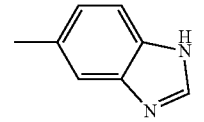 | H |
| 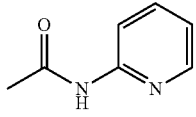 | H | 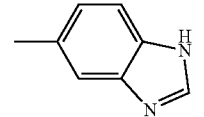 | H |
| 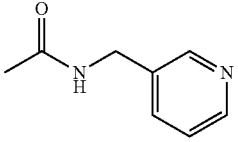 | H | 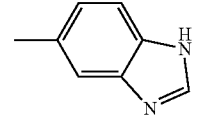 | H |
| CONHPh | H | 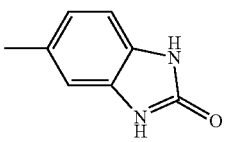 | H |
| CHF₂ | H | 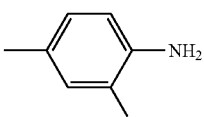 | Me |
| CHF₂ | H | 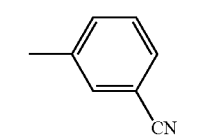 | Me |

-continued

| R₂ | R₃ | R₁ | R₄ |
|---|---|---|---|
| CHF₂ | H | 4-aminophenyl | Me |
| CHF₂ | H | 2-amino-5-methyl-3-cyanophenyl | H |
| CF₃ | Ph | 2-amino-5-methyl-3-cyanophenyl | propyl-NMe₂ |
| CF₃ | Ph | 5-methyl-2-methoxy-3-cyanopyridinyl | Me |
| CHF₂ | Ph | 2-amino-5-methyl-3-cyanophenyl | Me |
| CHF₂ | Ph | 4-aminophenyl | Me |
| CHF₂ | Ph | 3-(NMe₂)phenyl | Me |
| CF₃ | Ph | 2-amino-5-methyl-3-cyanophenyl | propyl-piperidinyl |
| CF₃ | Ph | 3-(NMe₂)phenyl | propyl-piperidinyl |
| CHF₂ | Ph | 2-amino-5-methyl-3-cyanophenyl | propyl-NMe₂ |
| CF₃ | H | 3-(NMe₂)phenyl | propyl-morpholinyl |

-continued

| R₂ | R₃ | R₁ | R₄ |
|---|---|---|---|
| CF₃ | H | 5-methyl-3-cyanopyridin-3-yl (methyl-pyridine-CN) | N-propylmorpholine |
| CF₃ | H | 5-methyl-pyridine-3-carboxamide | N-propylmorpholine |
| CF₃ | H | 3-methylbenzyl-morpholine | Me |
| CF₃ | H | 2-amino-5-methyl-benzonitrile | Me |
| CF₃ | Ph | 4-methoxy-methylphenyl | Me |
| CF₃ | H | 3-methyl-N,N-dimethylaniline | Me |
| CHF₂ | 3-Py | 2-amino-5-methyl-benzonitrile | H |
| CHF₂ | 4-Py | 2-amino-5-methyl-benzonitrile | H |
| CF₃ | 3-Py | 3-methylbenzyl-morpholine | Me |
| CHF₂ | 3MeO—Ph | 2-amino-5-methyl-benzonitrile | Me |

-continued
| R₂ | R₃ | R₁ | R₄ |
|---|---|---|---|
| CF₃ | H | 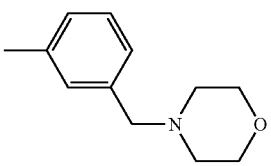 | Pr |
| CF₃ | H | 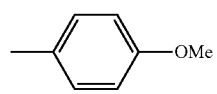 | Pr |
| CF₃ | 3MeO—Ph | 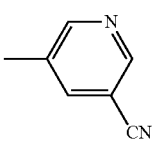 | Me |
| CF₃ | 3MeO—Ph | 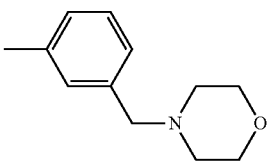 | Me |
| CF₃ | 3MeO—Ph | 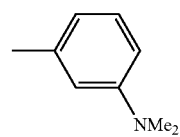 | Me |
| CF₃ | 3MeO—Ph | 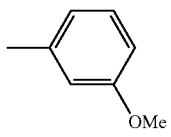 | Me |
| CONH₂ | 3-Py | 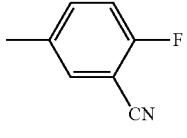 | H | in the form of the base or of an acid-addition or base-addition salt,
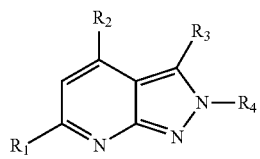
(I″)
wherein $R_1$, $R_2$, $R_3$ and $R_4$ are defined as follows:
| $R_2$ | $R_3$ | $R_1$ | $R_4$ |
|---|---|---|---|
| COOH | H | 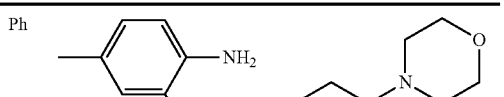 | Me |
| CONH$_2$ | H | 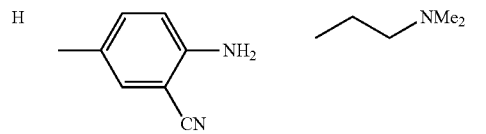 | Me |
| COOH | H | 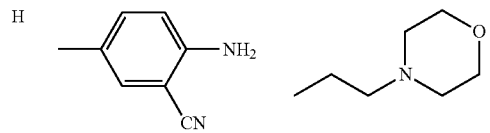 | Me |
| CHF$_2$ | H | 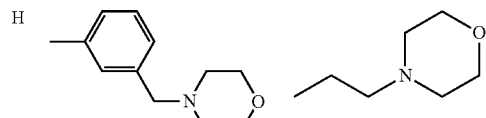 | Me |
| CHF$_2$ | H | 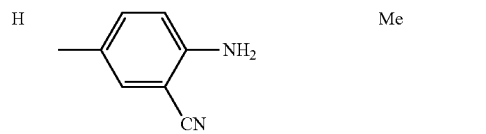 | Me |
| CHF$_2$ | H | 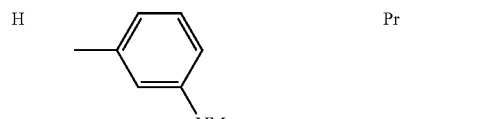 | Me |
| CF$_3$ | Ph | 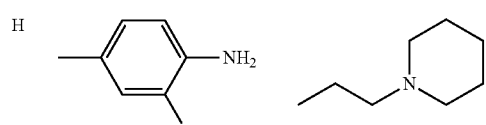 | Me |
| CF$_3$ | Ph | 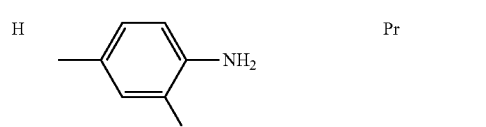 | 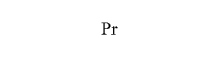 |
-continued
| $R_2$ | $R_3$ | $R_1$ | $R_4$ |
|---|---|---|---|
| CF$_3$ | Ph | 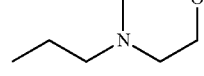 | 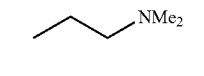 |
| CHF$_2$ | H | 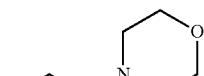 | 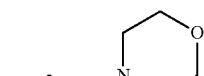 |
| CHF$_2$ | H |  | 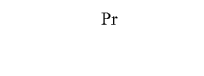 |
| CF$_3$ | H | 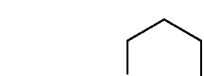 | 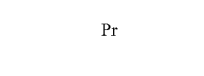 |
| CF$_3$ | H | 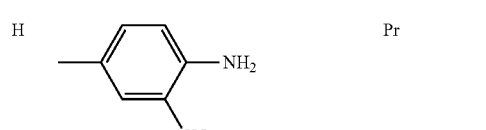 | Me |
| CF$_3$ | H | 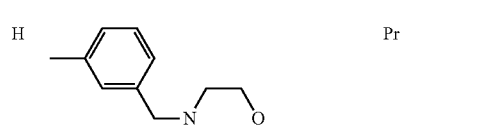 | Pr |
| CHF$_2$ | H | 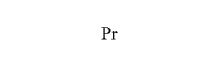 |  |
| CHF$_2$ | H | 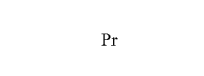 | Pr |
| CF$_3$ | H | | Pr |
| CF$_3$ | H | | Pr |
| CF$_3$ | H | | Pr | in the form of the base or of an acid-addition or base-addition salt,
and also at least one pharmaceutically acceptable excipient.

9. A pharmaceutical composition in the form of a tablet, soft or hard gel capsule, powder or granule, comprising a compound of formula (I') or (I''):

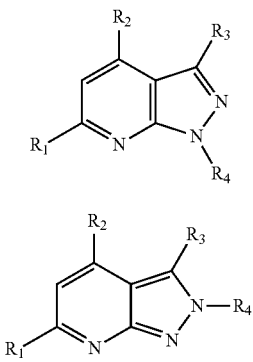

wherein
R₁ is aryl, pyridyl or pyrazolyl, each optionally substituted with one or more substituents chosen from halogen, —CF₃, cyano, —NR₆R₆', —NR₁₀R₁₁ wherein R₁₀ and R₁₁ form, together with the nitrogen atom to which they are attached, a saturated or unsaturated heterocycle comprising one or more heteroatoms chosen from a nitrogen atom and an oxygen atom, optionally substituted with one or more substituents chosen from halogen and linear or branched alkyl, —CH₂NR₁₀R₁₁ wherein R₁₀ and R₁₁ form, together with the nitrogen atom to which they are attached, a saturated or unsaturated heterocycle comprising one or more heteroatoms chosen from a nitrogen atom and an oxygen atom, —COR₁₂ wherein R₁₂ is hydroxyl or —NR₆R₆', —CONR₇R₇' wherein R₇ and R₇' form, together with the nitrogen atom to which they are attached, a heterocycloalkyl comprising one or more heteroatoms chosen from a nitrogen atom and an oxygen atom, —(CH₂)ₚNHSO₂CH₃ wherein p is 0 or 1, —OR₁₃ wherein R₁₃ linear (C₁-C₃)alkyl, (C₁-C₃)alkyl,
or R₁ is a bicyclic group of formula A:

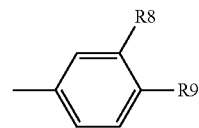

wherein R₈ and R₉ form, together with the phenyl ring to which they are attached, a saturated or unsaturated heterocycle comprising one or more heteroatoms chosen from a nitrogen atom, an oxygen atom and a sulfur atom, optionally substituted with one or more linear alkyl groups;
R₂ is —CF₃, —CHF₂, —COOH, or —CONHR₅;
R₃ is hydrogen, aryl optionally substituted with alkoxymethyl, cycloalkyl or heteroaryl chosen from thienyl and pyridyl;
R₄ is hydrogen, linear (C₁-C₃)alkyl optionally substituted with —NR₆R₆' or —NR₇R₇' wherein R₇ and R₇' form, together with the nitrogen atom to which they are attached, a heterocycloalkyl comprising one or more heteroatoms chosen from a nitrogen atom and an oxygen atom;
R₅ is hydrogen, linear (C₁-C₃)alkyl optionally substituted with pyridyl, or an aromatic group chosen from aryl and pyridyl;
R₆ and R₆', are independently hydrogen or a linear alkyl group,
in the form of the base or of an acid-addition or base-addition salt, or a pharmaceutically acceptable salt thereof,
and at least one pharmaceutically acceptable excipient.

10. The pharmaceutical composition according to claim 9, wherein the compound is of formula (I'):

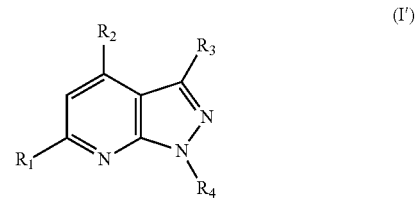

wherein R₁, R₂, R₃ and R₄ are defined as follows:

| R₂ | R₃ | R₁ | R₄ |
|---|---|---|---|
| CF₃ | Ph | ![phenyl-CONH₂] | Me |
| CF₃ | Ph | ![phenyl-CH₂NHSO₂Me] | Me |
| CF₃ | Ph | ![N-methylindole] | Me |

-continued

| R₂ | R₃ | R₁ | R₄ |
|---|---|---|---|
| CF₃ | Ph | 3-methylphenyl-NHSO₂Me | Me |
| CF₃ | Ph | 4-methyl-N-methyl-3,4-dihydro-2H-benzo[b][1,4]oxazine | Me |
| CF₃ | Ph | 3-methylbenzyl-NHSO₂Me | Me |
| CF₃ | Ph | 4-methylphenyl-OMe | Me |
| CF₃ | Ph | 5-methyl-2-fluorophenyl-CONHMe | Me |
| CF₃ | Ph | 3-methylphenyl-NMe₂ | Me |
| CF₃ | Ph | 4-methylphenyl-(3,5-dimethyl-1H-pyrazol-1-yl) | Me |
| CF₃ | Ph | 3-methylbenzyl-morpholine | Me |
| CF₃ | Ph | 5-methyl-3-cyanopyridine | Me |
| CF₃ | Ph | 4-methylbenzoic acid (COOH) | Me |
| CF₃ | Ph | 4-methylphenyl-CONMe₂ | Me |

-continued

| R₂ | R₃ | R₁ | R₄ |
|---|---|---|---|
| CF₃ | Ph | 4-(CONMe₂)-phenyl | Me |
| CF₃ | Ph | 5-methyl-2-morpholinopyridine | Me |
| CF₃ | Ph | 5-methyl-2-methoxypyridine | Me |
| CF₃ | Ph | 5-methyl-2-(pyrrolidin-1-yl)pyridine | Me |
| CF₃ | Ph | 1,5-dimethyl-3-(trifluoromethyl)-1H-pyrazole | Me |
| CF₃ | Ph | 6-methylbenzo[d]thiazole | Me |
| CF₃ | Ph | 4-(CONMe₂)-phenyl | H |
| CF₃ | Ph | 4-morpholinophenyl | H |
| CF₃ | Ph | 5-methyl-2-morpholinopyridine | H |
| CF₃ | Ph | 5-methyl-2-methoxypyridine | H |
| CF₃ | Ph | 3-morpholino-5-methylphenyl | H |
| CF₃ | Ph | 4-(CONHMe)-phenyl | H |

-continued
| R₂ | R₃ | R₁ | R₄ |
|---|---|---|---|
| CF₃ | Ph | 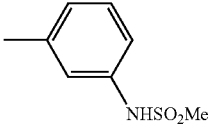 | H |
| CF₃ | Ph | 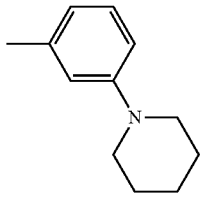 | H |
| CF₃ | Ph | 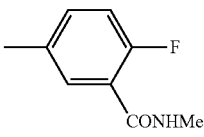 | H |
| CF₃ | Ph | 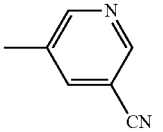 | H |
| CHF₂ | Ph | 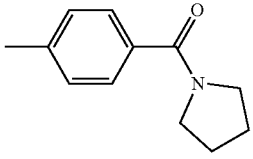 | H |
| CHF₂ | Ph | 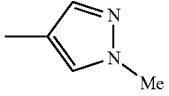 | H |
| CHF₂ | Ph | 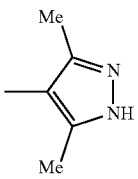 | H |
| CHF₂ | Ph | 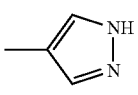 | H |
| CHF₂ | Ph | 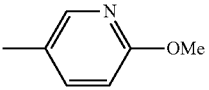 | H |
| CHF₂ | Ph | 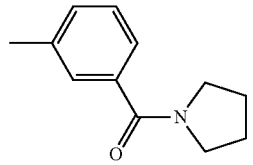 | H |

-continued
| R₂ | R₃ | R₁ | R₄ |
|---|---|---|---|
| CHF₂ | Ph | 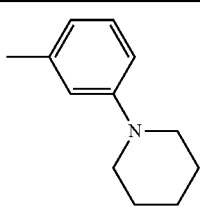 | H |
| COOH | H | 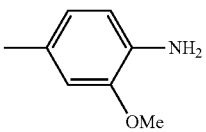 | H |
| CONHMe | Ph | 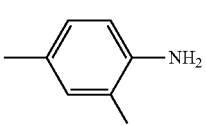 | H |
| CONH₂ | Ph | 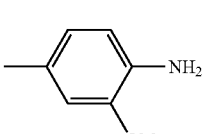 | H |
| CONHMe | H | 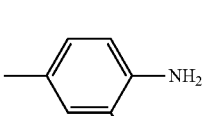 | H |
| CONH₂ | H | 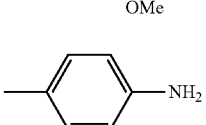 | H |
| COOH | Ph | 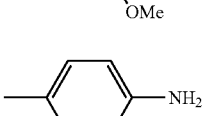 | H |
| COOH | Ph | 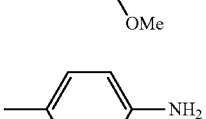 | Me |
| COOH | H | 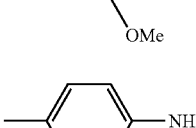 | Me |
| CONH₂ | Ph | 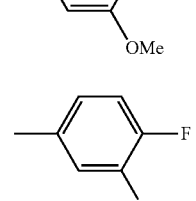 | H |

-continued

| R₂ | R₃ | R₁ | R₄ |
|---|---|---|---|
| CONH₂ | Ph | 2-amino-5-methylbenzoic acid | H |
| CONH₂ | Ph | 2-amino-4-methylbenzonitrile | 2H |
| CONH₂ | 2-thienyl | 2-amino-4-methylbenzonitrile | 2H |
| COOH | cPr | 2-amino-4-methylbenzonitrile | H |
| CONH₂ | H | 2-fluoro-5-methylbenzoic acid | H |
| CONH₂ | Ph | 2-fluoro-4-methylbenzonitrile | H |
| CHF₂ | Ph | 2-fluoro-5-methylbenzoic acid | H |
| CF₃ | Ph | 2-fluoro-4-methylbenzonitrile | H |
| CHF₂ | Ph | 2-amino-4-methylbenzonitrile | H |
| CF₃ | Ph | 2-fluoro-5-methylbenzoic acid | H |
| CF₃ | Ph | 2-amino-4-methylbenzonitrile | Me |

-continued
| R₂ | R₃ | R₁ | R₄ |
|---|---|---|---|
| CF₃ | Ph | 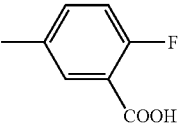 | Me |
| CF₃ | Ph | 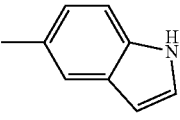 | H |
| CF₃ | Ph | 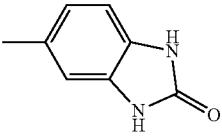 | H |
| CF₃ | Ph | 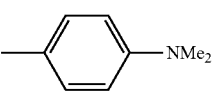 | H |
| CONHPh | H | 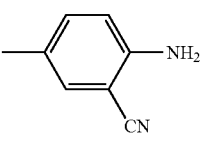 | H |
| 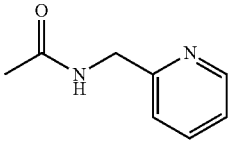 | H | 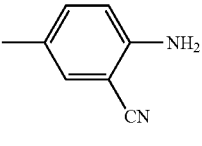 | H |
| 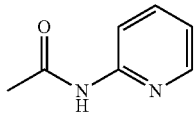 | H | 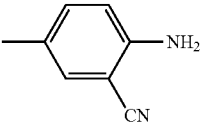 | H |
| 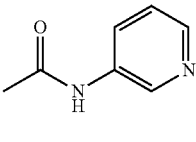 | H | 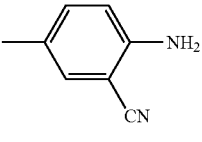 | H |
| 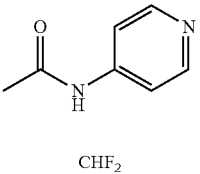 | H | 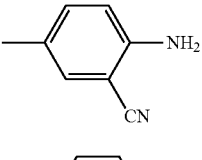 | H |
| CHF₂ | 4-Py | 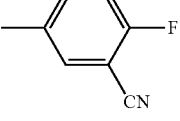 | Me |
| CONHPh | H | 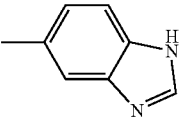 | H |

-continued

| R₂ | R₃ | R₁ | R₄ |
|---|---|---|---|
| *N-(pyridin-2-yl)acetamide* | H | *5-methyl-1H-benzimidazole* | H |
| *N-(pyridin-3-ylmethyl)acetamide* | H | *5-methyl-1H-benzimidazole* | H |
| CONHPh | H | *5-methyl-1,3-dihydro-2H-benzimidazol-2-one* | H |
| CHF₂ | H | *2-amino-5-methylbenzonitrile* | Me |
| CHF₂ | H | *3-methylbenzonitrile* | Me |
| CHF₂ | H | *4-methylaniline* | Me |
| CHF₂ | H | *2-amino-5-methylbenzonitrile* | H |
| CF₃ | Ph | *2-amino-5-methylbenzonitrile* | *N,N-dimethylpropan-1-amine* |
| CF₃ | Ph | *5-methyl-2-methoxypyridine-3-carbonitrile* | Me |
| CHF₂ | Ph | *2-amino-5-methylbenzonitrile* | Me |
| CHF₂ | Ph | *4-methylaniline* | Me |

-continued

| R₂ | R₃ | R₁ | R₄ |
|---|---|---|---|
| CHF₂ | Ph | 3-(NMe₂)-phenyl | Me |
| CF₃ | Ph | 2-amino-3-cyano-phenyl | 1-propylpiperidine |
| CF₃ | Ph | 3-(NMe₂)-phenyl | 1-propylpiperidine |
| CHF₂ | Ph | 2-amino-3-cyano-phenyl | propyl-NMe₂ |
| CF₃ | H | 3-(NMe₂)-phenyl | 4-propylmorpholine |
| CF₃ | H | 5-cyano-pyridin-3-yl | 4-propylmorpholine |
| CF₃ | H | 5-carbamoyl-pyridin-3-yl | 4-propylmorpholine |
| CF₃ | H | 3-(morpholinomethyl)phenyl | Me |
| CF₃ | H | 2-amino-3-cyano-phenyl | Me |
| CF₃ | Ph | 4-OMe-phenyl | Me |
| CF₃ | H | 3-(NMe₂)-phenyl | Me |

-continued
| R₂ | R₃ | R₁ | R₄ |
|---|---|---|---|
| CHF₂ | 3-Py | 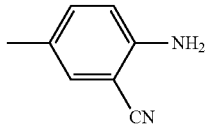 | H |
| CHF₂ | 4-Py | 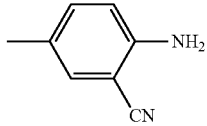 | H |
| CF₃ | 3-Py | 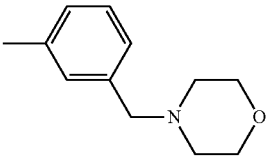 | Me |
| CHF₂ | 3MeO—Ph | 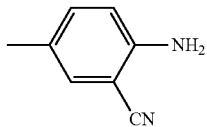 | Me |
| CF₃ | H | 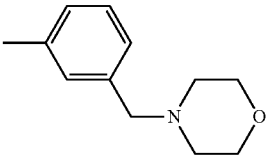 | Pr |
| CF₃ | H | 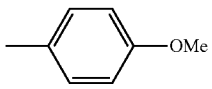 | Pr |
| CF₃ | 3MeO—Ph | 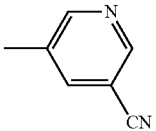 | Me |
| CF₃ | 3MeO—Ph | 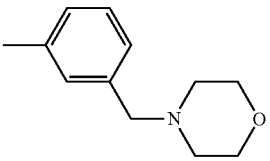 | Me |
| CF₃ | 3MeO—Ph | 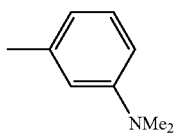 | Me |
| CF₃ | 3MeO—Ph | 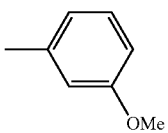 | Me |

-continued
| R$_2$ | R$_3$ | R$_1$ | R$_4$ |
|---|---|---|---|
| CONH$_2$ | 3-Py | 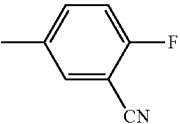 | H |
in the form of the base or of an acid-addition or base-addition salt or of formula (I″):
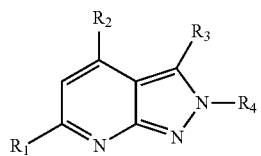
(I″)
wherein R$_1$, R$_2$, R$_3$ and R$_4$ are defined as follows:
| R$_2$ | R$_3$ | R$_1$ | R$_4$ |
|---|---|---|---|
| COOH | H | 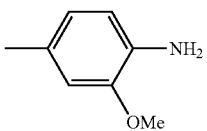 | Me |
| CONH$_2$ | H | 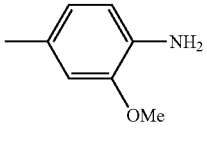 | Me |
| COOH | H | 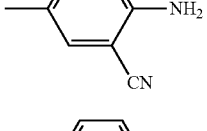 | Me |
| CHF$_2$ | H | 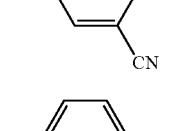 | Me |
| CHF$_2$ | H | 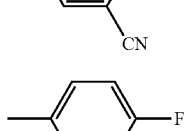 | Me |
| CHF$_2$ | H | 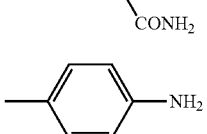 | Me |
| CF$_3$ | Ph |  | Me |
-continued
| R$_2$ | R$_3$ | R$_1$ | R$_4$ |
|---|---|---|---|
| CF$_3$ | Ph | 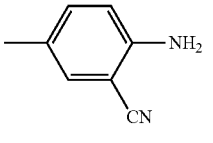 | 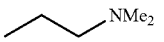 |
| CF$_3$ | Ph | 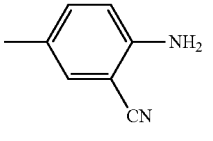 | 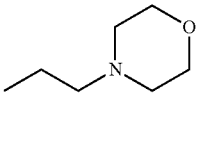 |
| CHF$_2$ | H | 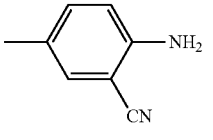 | 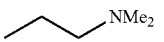 |
| CHF$_2$ | H | 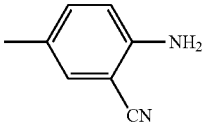 | 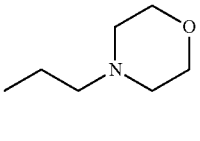 |
| CF$_3$ | H | 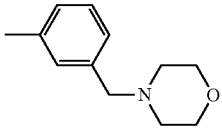 | 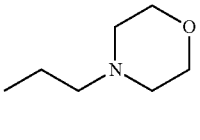 |
| CF$_3$ | H | 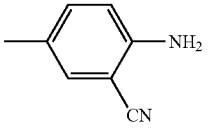 | Me |
| CF$_3$ | H | 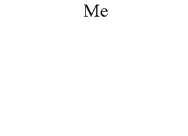 | Pr |
| CHF$_2$ | H | 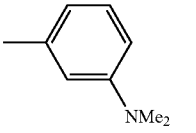 | 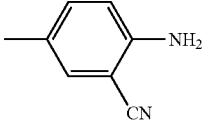 |
| CHF$_2$ | H | 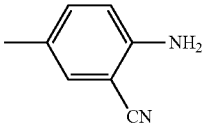 | Pr |

-continued

| R$_2$ | R$_3$ | R$_1$ | R$_4$ |
|---|---|---|---|
| CF$_3$ | H | 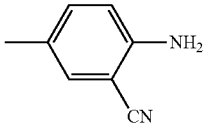 | Pr |
| CF$_3$ | H | 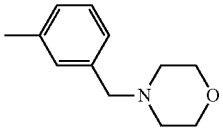 | Pr |
| CF$_3$ | H | 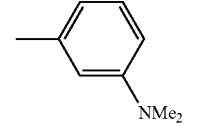 | Pr | in the form of the base or of an acid-addition or base-addition salt.

11. The pharmaceutical composition according to claim 9, wherein the compound is
N-[3-(3-Phenyl-4-trifluoromethyl-1H-pyrazolo[3,4-b]pyridin-6-yl)-phenyl]-methanesulfonamide;
N-Methyl-3-(3-phenyl-4-trifluoromethyl-1H-pyrazolo[3,4-b]pyridin-6-yl)-benzamide;
6-(4-Methoxy-phenyl)-3-phenyl-4-trifluoromethyl-1H-pyrazolo[3,4-b]pyridine;
Dimethyl-[4-(3-phenyl-4-trifluoromethyl-1H-pyrazolo[3,4-b]pyridin-6-yl)-phenyl]-amine;
N-[3-(1-Methyl-3-phenyl-4-trifluoromethyl-1H-pyrazolo[3,4-b]pyridin-6-yl)-phenyl]-methanesulfonamide;
4-(1-Methyl-3-phenyl-4-trifluoromethyl-1H-pyrazolo[3,4-b]pyridin-6-yl)-benzoic acid; or
6-(4-Morpholin-4-yl-phenyl)-3-phenyl-4-trifluoromethyl-1H-pyrazolo[3,4-b]pyridine;
in the form of the base or of an acid-addition or base-addition salt.

* * * * *